US011952353B2

(12) United States Patent
Reigan et al.

(10) Patent No.: US 11,952,353 B2
(45) Date of Patent: Apr. 9, 2024

(54) STAT3 TRANSCRIPTION FACTOR INHIBITORS AND METHODS OF USING THE SAME

(71) Applicant: The Regents of the University of Colorado, A Body Corporate, Denver, CO (US)

(72) Inventors: Philip Reigan, Denver, CO (US); Donald S. Backos, Aurora, CO (US); Christopher J. Matheson, Denver, CO (US); Steffanie L. Furtek, Aurora, CO (US); Craig T. Jordan, Aurora, CO (US); Maria L. Amaya, Aurora, CO (US)

(73) Assignee: The Regents of the University of Colorado, Denver, CO (US)

(*) Notice: Subject to any disclaimer, the term of this patent is extended or adjusted under 35 U.S.C. 154(b) by 0 days.

(21) Appl. No.: 17/311,021

(22) PCT Filed: Dec. 6, 2019

(86) PCT No.: PCT/US2019/065085
§ 371 (c)(1),
(2) Date: Jun. 4, 2021

(87) PCT Pub. No.: WO2020/118265
PCT Pub. Date: Jun. 11, 2020

(65) Prior Publication Data
US 2022/0017476 A1    Jan. 20, 2022

Related U.S. Application Data

(60) Provisional application No. 62/878,655, filed on Jul. 25, 2019, provisional application No. 62/776,696, filed on Dec. 7, 2018.

(51) Int. Cl.
| | | |
|---|---|---|
| C07D 263/57 | (2006.01) | |
| C07C 205/43 | (2006.01) | |
| C07C 233/66 | (2006.01) | |
| C07C 235/64 | (2006.01) | |
| C07D 233/26 | (2006.01) | |
| C07D 263/32 | (2006.01) | |
| C07D 307/16 | (2006.01) | |
| C07D 307/54 | (2006.01) | |
| C07D 307/56 | (2006.01) | |
| C07D 307/58 | (2006.01) | |
| C07D 307/66 | (2006.01) | |
| C07D 307/68 | (2006.01) | |
| C07D 307/80 | (2006.01) | |

(52) U.S. Cl.
CPC .......... C07D 263/57 (2013.01); C07C 205/43 (2013.01); C07C 235/64 (2013.01); C07D 233/26 (2013.01); C07D 263/32 (2013.01); C07D 307/16 (2013.01); C07D 307/54 (2013.01); C07D 307/56 (2013.01)

(58) Field of Classification Search
CPC .. C07D 263/57; C07D 263/32; C07D 205/43; C07D 235/64; C07D 233/26; C07D 307/16; C07D 307/54; C07D 307/56; C07D 307/58; C07D 307/66; C07D 307/68; C07D 307/80; C07C 233/66
See application file for complete search history.

(56) References Cited

U.S. PATENT DOCUMENTS 8,148,328 B2 *   4/2012   Fogelman .............. A61K 38/16
424/9.1

FOREIGN PATENT DOCUMENTS

CN    109 053 480 A    12/2018

OTHER PUBLICATIONS

Niclosamide, 2022, https://pubchem.ncbi.nlm.nih.gov/compound/Niclosamide.*
RN312755-59-2, 2001, registry database compound.*
RN50-65-7, 1984, registry database compound.*
CancerPrevention, 2022, https://www.cancer.gov/about-cancer/causes-prevention#:~:text=Cancer%20prevention%20is%20action%20taken,can%20prevent%20cancer%20from%20developing.*
PubChem CID 817996, Jul. 8, 2005, 10 pages.
Fukai et al. "Design and Synthesis of Novel Cyclooxygenase-1 Inhibitors as Analgesics: 5-Amino-2-ethoxy-N-(substituted-phenyl)benzamides", CHEMMEDCHEM, vol. 6, No. 3, 2011, pp. 550-560.
Furtek et al. "Evaluation of quantitative assays for the identification of direct signal transducer and activator of transcription 3 (STAT3) inhibitors", Oncotarget, vol. 7, No. 47, 2016, pp. 77998-78008.
Lemaire H et al. "Synthesis and germicidal activity of halogenated salicylanilides and related compounds", Journal of Pharmaceutical Sciences, vol. 50, No. 10, 1961, pp. 831-837.
Mook R et al. "Structure-activity studies of Wnt/beta-catenin inhibition in the Niclosamide chemotype: identification of derivatives with improved drug exposure", Bioorganic & Medicinal Chemistry, vol. 23, 2015, pp. 5829-5838.
Yang et al. "Copper-Catalyzed Domino Synthesis of Benzimidazo[2,1-b]quin-azolin-12(6H)-ones Using Cyanamide as a Building Block", Advanced Synthesis & Catalysis, vol. 354, No. 2-3, 2012, pp. 477-482.

(Continued)

*Primary Examiner* — Sun Jae Yoo
(74) *Attorney, Agent, or Firm* — Snell & Wilmer L.L.P.

(57) ABSTRACT

Compounds that inhibit the activity of Signal transducer and activator of transcription 3 (STAT3), or pharmaceutically acceptable salts or prodrugs thereof, and methods of using these compounds to treat cancer and other diseases.

16 Claims, 28 Drawing Sheets

(56) References Cited

OTHER PUBLICATIONS

Zhu et al. "Synthesis and antiproliferative activities against Hep-G2 of salicylanide derivatives: potent inhibitors of the epidermal growth factor receptor (EGFR)tyrosine kinase", Journal of Enzyme Inhibition and Medicinal Chemistry, vol. 26, No. 1, 2010, pp. 37-45.

* cited by examiner

Conditions: POCl₃, anhyd. Toluene, 180 °C, microwave irradiation, 1h

STAT3 TRANSCRIPTION FACTOR INHIBITORS AND METHODS OF USING THE SAME

RELATED APPLICATIONS

This application is a U.S. national phase application, filed under U.S.C. § 371, of International Application No. PCT/US2019/065085, filed Dec. 6, 2019, which claims priority to, and benefit of U.S. Provisional Application No. 62/878,655, filed Jul. 25, 2019, and U.S. Provisional Application No. 62/776,696, filed Dec. 7, 2018, filed. The contents of each of the aforementioned patent applications are incorporated herein by reference in their entireties.

TECHNICAL FIELD

The invention relates to improvements in anti-inflammatory and cancer chemotherapy treatments.

BACKGROUND OF DISCLOSURE

Signal transducer and activator of transcription 3 (STAT3) is a transcription factor that regulates the expression of genes related to cell cycle, cell survival, and immune response associated with cancer progression and malignancy in a number of cancer types.

STAT3 is activated through the binding of cytokines or growth factors to cell surface receptors. Cytokines such as the interleukins IL-6, IL-10, and IL-11, as well as growth factors such as EGF, fibroblast growth factor (FGF), and vascular endothelial growth factor (VEGF) can activate the tyrosine phosphorylation cascade. Once ligands bind to their corresponding receptors, the receptors form a dimer complex. Activation of glycoprotein 130 (gp130) is also initiated, inducing dimerization of gp130 and the α-receptor subunit of the receptor. Together the ligand receptor and gp130 complex recruit Janus kinases (JAKs). The aggregation of JAKs leads to their activation via phosphorylation, which in turn phosphorylates the cytoplasmic tyrosine residues on the receptors that serve as a dock for the Src homology 2 (SH2) domain of STAT3. STAT3 becomes activated (p-STAT3) through the phosphorylation of its Tyr705 residue located within its SH2 domain. Activation of STAT3 triggers p-STAT3 to form a homodimer via the interaction of the p-Tyr705 of one monomer and the SH2 domain of another.

Once activated, STAT3 forms a homodimer and translocates to the nucleus where it binds DNA, promoting the translation of target genes associated with anti-apoptosis, angiogenesis, and invasion/migration. In normal cells, levels of activated STAT3 remain transient; however, STAT3 remains constitutively active in approximately 70% of human hematological and solid tumors. The pivotal role of STAT3 in tumor progression has prompted the design of small molecules that disrupt the function of STAT3. A range of approaches have been used to identify novel small molecule inhibitors of STAT3, including high-throughput screening of chemical libraries, computational-based virtual screening, and fragment-based design strategies. The most common approaches in targeting STAT3 activity are either via the inhibition of tyrosine kinases capable of phosphorylating and thereby activating STAT3, or by preventing the formation of functional STAT3 dimers through disruption of the SH2 domains. However, the targeting of the STAT3 DNA binding domain and disruption of binding of STAT3 to its DNA promoter have not been thoroughly examined, mainly due to the lack of adequate assay systems.

It is therefore desirable to find direct inhibitors of the DNA binding domain(s) of STAT3 to more directly inhibit the transcription induced by this transcription factor and its carcinogenic and anti-apoptotic activities.

SUMMARY

In some aspects, the present disclosure provides a compound of Formula (I) or (II):

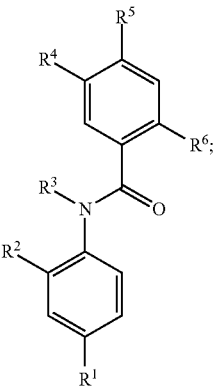

(I)

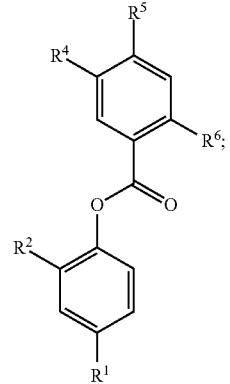

(II)

or a pharmaceutically acceptable salt thereof, wherein:

$R^1$ is H, $C_{1-6}$ alkyl, substituted $C_{1-6}$ alkyl, $C_{1-6}$ alkoxy, aryl, substituted aryl, heteroaryl, substituted heteroaryl, nitro, CN, $SO_3H$, $OR^{1S}$ where $R^{1S}$ is H, $C_{1-6}$ alkyl, substituted $C_{1-6}$ alkyl, $C_{3-8}$ cycloalkyl, aryl, substituted aryl, heteroaryl, substituted heteroaryl, or $NR^{1Sa}R^{1Sb}$ where $R^{1Sa}$ and $R^{1Sb}$ are independently H, $C_{1-8}$ alkyl, substituted $C_{1-8}$ alkyl, $C_{3-8}$ cycloalkyl, $C_{2-4}$ alkenyl, aryl such as a phenyl, substituted aryl, heteroaryl or substituted heteroaryl;

$R^2$ is H, $C_{1-6}$ alkyl, substituted $C_{1-6}$ alkyl, $C_{1-6}$ alkoxy, aryl, substituted aryl, heteroaryl, substituted heteroaryl, halogen, $OR^{2S}$ where $R^{2S}$ is H, $C_{1-6}$ alkyl, substituted $C_{1-6}$ alkyl, $C_{3-8}$ cycloalkyl, aryl, substituted aryl, heteroaryl, substituted heteroaryl, or $NR^{2Sa}R^{2Sb}$ where $R^{2Sa}$ and $R^{2Sb}$ are independently H, $C_{1-8}$ alkyl, substituted $C_{1-8}$ alkyl, $C_{3-8}$ cycloalkyl, $C_{2-4}$ alkenyl, aryl such as a phenyl, substituted aryl, heteroaryl or substituted heteroaryl;

$R^3$ is H, $C_{1-6}$ alkyl, substituted $C_{1-6}$ alkyl, aryl, substituted aryl, heteroaryl, or substituted heteroaryl;

$R^4$ is H, $C_{1-6}$ alkyl, substituted $C_{1-6}$ alkyl, $C_{1-6}$ alkoxy, aryl, substituted aryl, heteroaryl, substituted heteroaryl, halogen, nitro, $OR^{4S}$ where $R^{4S}$ is H, $C_{1-6}$ alkyl, substituted $C_{1-6}$ alkyl, $C_{3-8}$ cycloalkyl, aryl, substituted aryl, heteroaryl, substituted heteroaryl, or $NR^{4Sa}R^{4Sb}$ where $R^{4Sa}$ and $R^{4Sb}$ are independently H, $C_{1-8}$ alkyl, substituted $C_{1-8}$ alkyl, $C_{3-8}$ cycloalkyl, $C_{2-4}$ alkenyl, aryl such as a phenyl, substituted aryl, heteroaryl or substituted heteroaryl;

$R^5$ is H, $C_{1-6}$ alkyl, substituted $C_{1-6}$ alkyl, $C_{1-6}$ alkoxy, aryl, substituted aryl, heteroaryl, substituted heteroaryl, Or where $R^{5S}$ is H, $C_{1-6}$ alkyl, substituted $C_{1-6}$ alkyl, $C_{3-8}$ cycloalkyl, aryl, substituted aryl, heteroaryl, substituted heteroaryl, or $NR^{5Sa}R^{5Sb}$ where $R^{5Sa}$ and $R^{5Sb}$ are independently H, $C_{1-8}$ alkyl, substituted $C_{1-8}$ alkyl, $C_{3-8}$ cycloalkyl, $C_{2-4}$ alkenyl, aryl such as a phenyl, substituted aryl, heteroaryl or substituted heteroaryl; and $R^6$ is H, $C_{1-6}$ alkyl, substituted $C_{1-6}$ alkyl, $C_{1-6}$ alkoxy, aryl, substituted aryl, heteroaryl, substituted heteroaryl, halogen, $OR^{6S}$, or $—C(=O)—OR^{6S}$ where $R^{6S}$ is H, $C_{1-6}$ alkyl, $—C(=O)—C_{1-6}$ alkyl, substituted $C_{1-6}$ alkyl, $C_{3-8}$ cycloalkyl, aryl, substituted aryl, heteroaryl, substituted heteroaryl, or $NR^{6Sa}R^{6Sb}$ where $R^{6Sa}$ and $R^{6Sb}$ are independently H, $C_{1-8}$ alkyl, substituted $C_{1-8}$ alkyl, $C_{3-8}$ cycloalkyl, $C_{2-4}$ alkenyl, aryl such as a phenyl, substituted aryl, heteroaryl or substituted heteroaryl.

Another aspect of this disclosure provides pharmaceutical compositions comprising at least one STAT3 inhibitor compound of this disclosure and at least one pharmaceutically acceptable additive.

Another aspect of this disclosure provides pharmaceutical kits containing a pharmaceutical composition of this disclosure, prescribing information for the composition, and a container.

Another aspect of this disclosure provides methods for inhibiting STAT3 activity in a subject, including administering to the subject a therapeutically effective amount of a STAT3 inhibitor compound of this disclosure, or a pharmaceutically acceptable salt thereof.

This disclosure also provides methods of preventing, treating, or ameliorating cancer, or preventing metastasis of a cancer in a subject, including administering a therapeutically-effective amount of a compound of this disclosure that inhibits STAT3 transcription factor to a subject in need thereof.

In these methods, the cancer may be a solid tumor, a blood cancer (including, for example, acute myeloid leukemia). Specific cancers that may be particularly well suited to treatment with a compound of this disclosure that inhibits STAT3 transcription factor include colorectal cancer, hepatocellular carcinoma, non-small cell lung cancer, ovarian cancer, prostate cancer, breast cancer (including triple negative breast cancer), T-cell lymphoma, Hodgkin's lymphoma, gastric cancer, skin cancer (esp. melanoma), leukemia, squamous cell carcinoma, nasopharyngeal carcinoma, glioblastoma, pancreatic ductal adenocarcinoma, and obesity-induced hepatocellular carcinoma.

These methods may also be used to prevent, treat, or ameliorate inflammation induced carcinogenesis, including for example liver and gastric cancers arising from infections that cause chronic hepatitis, and colon cancer associated with Crohn's colitis and ulcerative colitis.

In these methods, the STAT3 inhibitor compound may be administered to the subject within a pharmaceutical composition. The pharmaceutical composition may be a monophasic pharmaceutical composition suitable for parenteral or oral administration consisting essentially of a therapeutically-effective amount of the STAT3 inhibitor compound, and a pharmaceutically acceptable additive.

In these methods, the compounds and/or pharmaceutical compositions of the present disclosure may be administered in combination with one or more additional therapeutic agents. Additional therapeutic agents can include, but are not limited to, chemotherapeutic agents, anti-cancer agents, DNA alkylating agents, DNA damage response (DDR) inhibitors, cell-cycle checkpoint inhibitors, PARP inhibitors, HDAC inhibitors, kinase inhibitors, Bcl-2 inhibitors, Mcl-1 inhibitors, PD-L1 targeted agents, immunotherapy agents and bioenergetics modulators. Additional therapeutic agents can include, but are not limited to, cisplatin, cytarabine, doxorubicin, paclitaxel, temozolomide, dasatinib, nilotinib, fluvestrant, venetoclax, metformin, or combinations thereof.

In some aspects, anti-cancer agents can include, but are not limited to, 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abemaciclib, Abiraterone acetate, Abraxane, Accutane, Actinomycin-D, Adcetris, Ado-Trastuzumab Emtansine, Adriamycin, Adrucil, Afatinib, Afinitor, Agrylin, Ala-Cort, Aldesleukin, Alemtuzumab, Alecensa, Alectinib, Alimta, Alitretinoin, Alkaban-AQ, Alkeran, All-transretinoic Acid, Alpha Interferon, Altretamine, Alunbrig, Amethopterin, Amifostine, Aminoglutethimide, Anagrelide, Anandron, Anastrozole, Apalutamide, Arabinosylcytosine, Ara-C, Aranesp, Aredia, Arimidex, Aromasin, Arranon, Arsenic Trioxide, Arzerra, Asparaginase, Atezolizumab, Atra, Avastin, Avelumab, Axicabtagene Ciloleucel, Axitinib, Azacitidine, Bavencio, Bcg, Beleodaq, Belinostat, Bendamustine, Bendeka, Besponsa, Bevacizumab, Bexarotene, Bexxar, Bicalutamide, Bicnu, Blenoxane, Bleomycin, Blinatumomab, Blincyto, Bortezomib, Bosulif, Bosutinib, Brentuximab Vedotin, Brigatinib, Busulfan, Busulfex, C225, Cabazitaxel, Cabozantinib, Calcium Leucovorin, Campath, Camptosar, Camptothecin-11, Capecitabine, Caprelsa, Carac, Carboplatin, Carfilzomib, Carmustine, Carmustine Wafer, Casodex, CCI-779, Ccnu, Cddp, Ceenu, Ceritinib, Cerubidine, Cetuximab, Chlorambucil, Cisplatin, Citrovorum Factor, Cladribine, Clofarabine, Clolar, Cobimetinib, Cometriq, Cortisone, Cosmegen, Cotellic, Cpt-11, Crizotinib, Cyclophosphamide, Cyramza, Cytadren, Cytarabine, Cytarabine Liposomal, Cytosar-U, Cytoxan, Dabrafenib, Dacarbazine, Dacogen, Dactinomycin, Daratumumab, Darbepoetin Alfa, Darzalex, Dasatinib, Daunomycin, Daunorubicin, Daunorubicin Cytarabine (Liposomal), daunorubicin-hydrochloride, Daunorubicin Liposomal, DaunoXome, Decadron, Decitabine, Degarelix, Delta-Cortef, Deltasone, Denileukin Diftitox, Denosumab, DepoCyt, Dexamethasone, Dexamethasone Acetate, Dexamethasone Sodium Phosphate, Dexasone, Dexrazoxane, Dhad, Dic, Diodex, Docetaxel, Doxil, Doxorubicin, Doxorubicin Liposomal, Droxia, DTIC, Dtic-Dome, Duralone, Durvalumab, Eculizumab, Efudex, Ellence, Elotuzumab, Eloxatin, Elspar, Eltrombopag, Emcyt, Empliciti, Enasidenib, Enzalutamide, Epirubicin, Epoetin Alfa, Erbitux, Eribulin, Erivedge, Erleada, Erlotinib, *Erwinia* L-asparaginase, Estramustine, Ethyol, Etopophos, Etoposide, Etoposide Phosphate, Eulexin, Everolimus, Evista, Exemestane, Fareston, Farydak, Faslodex, Femara, Filgrastim, Firmagon, Floxuridine, Fludara, Fludarabine, Fluoroplex, Fluorouracil, Fluorouracil (cream), Fluoxymesterone, Flutamide, Folinic Acid, Folotyn, Fudr, Fulvestrant, G-Csf, Gazyva, Gefitinib, Gemcitabine, Gemtuzumab ozogamicin, Gemzar, Gilotrif, Gleevec, Gleostine, Gliadel Wafer, Gm-Csf, Goserelin, Granix, Granulocyte-Colony Stimulating Factor, Granulocyte Macrophage Colony Stimulating Factor, Halaven, Halotestin, Herceptin, Hexadrol, Hexalen, Hexamethylmelamine, Hmm, Hycamtin, Hydrea, Hydrocort Acetate, Hydrocortisone, Hydrocortisone Sodium Phosphate, Hydrocortisone Sodium Succinate, Hydrocortone Phosphate, Hydroxyurea, Ibrance, Ibritumomab, Ibritumomab Tiuxetan, Ibrutinib, Iclusig, Idamycin, Idarubicin, Idelalisib, Idhifa, Ifex, IFN-alpha, Ifosfamide, IL-11, IL-2, Imbruvica, Imatinib Mesylate, Imfinzi, Imidazole Carboxamide, Imlygic, Inlyta, Inotuzumab Ozogamicin, Interferon-Alfa, Interferon Alfa-2b (PEG Conjugate), Interleukin-2, Interleukin-11, Intron A (interferon alfa-2b), Ipilimumab, Iressa, Irinotecan, Irinotecan (Liposomal), Isotretinoin, Istodax, Ixabepilone, Ixazomib, Ixempra, Jakafi, Jevtana, Kadcyla, Keytruda, Kidrolase, Kisqali, Kymriah, Kyprolis, Lanacort, Lanreotide, Lapatinib, Lartruvo, L-Asparaginase, Lbrance, Lcr, Lenalidomide, Lenvatinib, Lenvima, Letrozole, Leucovorin, Leukeran, Leukine, Leuprolide, Leurocristine, Leustatin, Liposomal Ara-C, Liquid Pred, Lomustine, Lonsurf, L-PAM, L-Sarcolysin, Lupron, Lupron Depot, Lynparza, Marqibo, Matulane, Maxidex, Mechlorethamine, Mechlorethamine Hydrochloride, Medralone, Medrol, Megace, Megestrol, Megestrol Acetate, Mekinist, Mercaptopurine, Mesna, Mesnex, Methotrexate, Methotrexate Sodium, Methylprednisolone, Meticorten, Midostaurin, Mitomycin, Mitomycin-C, Mitoxantrone, M-Prednisol, MTC, MTX, Mustargen, Mustine, Mutamycin, Myleran, Mylocel, Mylotarg, Navelbine, Necitumumab, Nelarabine, Neosar, Neratinib, Nerlynx, Neulasta, Neumega, Neupogen, Nexavar, Nilandron, Nilotinib, Nilutamide, Ninlaro, Nipent, Niraparib, Nitrogen Mustard, Nivolumab, Nolvadex, Novantrone, Nplate, Obinutuzumab, Octreotide, Octreotide Acetate, Odomzo, Ofatumumab, Olaparib, Olaratumab, Omacetaxine, Oncospar, Oncovin, Onivyde, Ontak, Onxal, Opdivo, Oprelvekin, Orapred, Orasone, Osimertinib, Otrexup, Oxaliplatin, Paclitaxel, Paclitaxel Protein-bound, Palbociclib, Pamidronate, Panitumumab, Panobinostat, Panretin, Paraplatin, Pazopanib, Pediapred, Peg Interferon, Pegaspargase, Pegfilgrastim, Peg-Intron, PEG-L-asparaginase, Pembrolizumab, Pemetrexed, Pentostatin, Perjeta, Pertuzumab, Phenylalanine Mustard, Platinol, Platinol-AQ, Pomalidomide, Pomalyst, Ponatinib, Portrazza, Pralatrexate, Prednisolone, Prednisone, Prelone, Procarbazine, Procrit, Proleukin, Prolia, Prolifeprospan 20 with Carmustine Implant, Promacta, Provenge, Purinethol, Radium 223 Dichloride, Raloxifene, Ramucirumab, Rasuvo, Regorafenib, Revlimid, Rheumatrex, Ribociclib, Rituxan, Rituxan Hycela, Rituximab, Rituximab Hyalurodinase, Roferon-A (Interferon Alfa-2a), Romidepsin, Romiplostim, Rubex, Rubidomycin Hydrochloride, Rubraca, Rucaparib, Ruxolitinib, Rydapt, Sandostatin, Sandostatin LAR, Sargramostim, Siltuximab, Sipuleucel-T, Soliris, Solu-Cortef, Solu-Medrol, Somatuline, Sonidegib, Sorafenib, Sprycel, Sti-571, Stivarga, Streptozocin, SU11248, Sunitinib, Sutent, Sylvant, Synribo, Tafinlar, Tagrisso, Talimogene Laherparepvec, Tamoxifen, Tarceva, Targretin, Tasigna, Taxol, Taxotere, Tecentriq, Temodar, Temozolomide, Temsirolimus, Teniposide, Tespa, Thalidomide, Thalomid, TheraCys, Thioguanine, Thioguanine Tabloid, Thiophosphoamide, Thioplex, Thiotepa, Tice, Tisagenlecleucel, Toposar, Topotecan, Toremifene, Torisel, Tositumomab, Trabectedin, Trametinib, Trastuzumab, Treanda, Trelstar, Tretinoin, Trexall, Trifluridine/Tipiricil, Triptorelin pamoate, Trisenox, Tspa, T-VEC, Tykerb, Valrubicin, Valstar, Vandetanib, VCR, Vectibix, Velban, Velcade, Vemurafenib, Venclexta, Venetoclax, VePesid, Verzenio, Vesanoid, Viadur, Vidaza, Vinblastine, Vinblastine Sulfate, Vincasar Pfs, Vincristine, Vincristine Liposomal, Vinorelbine, Vinorelbine Tartrate, Vismodegib, Vlb, VM-26, Vorinostat, Votrient, VP-16, Vumon, Vyxeos, Xalkori Capsules, Xeloda, Xgeva, Xofigo, Xtandi, Yervoy, Yescarta, Yondelis, Zaltrap, Zanosar, Zarxio, Zejula, Zelboraf, Zevalin, Zinecard, Ziv-aflibercept, Zoladex, Zoledronic Acid, Zolinza, Zometa, Zydelig, Zykadia, Zytiga, or any combination thereof.

In related aspects, this disclosure also provides the use of a STAT3 inhibitor compound of this disclosure, or a pharmaceutically acceptable salt thereof, in the manufacture of a medicament for the treatment of cancer. Similarly, this disclosure provides a STAT3 inhibitor compound of this disclosure, or a pharmaceutically acceptable salt thereof, for use in the treatment of cancer.

The present disclosure provides a STAT3 inhibitor compound for use in a method for modulating STAT3 transcription factor activity in a subject, wherein the STAT3 inhibitor compound is for administration to the subject in at least one therapeutically effective amount. Modulating STAT3 activity can comprise inhibiting STAT3 activity. Modulating STAT3 activity can comprise inhibiting STAT3 DNA-binding activity.

The present disclosure provides a STAT3 inhibitor compound for use in the prevention, treatment, amelioration of cancer or prevention of metastasis of a cancer in a subject, wherein the STAT3 inhibitor compound is for administration to the subject in at least one therapeutically effective amount. A cancer can be a solid tumor or a blood cancer. A cancer can be colorectal cancer, hepatocellular carcinoma, non-small cell lung cancer, ovarian cancer, prostate cancer, breast cancer, triple negative breast cancer, T-cell lymphoma, Hodgkin's lymphoma, gastric cancer, skin cancer, melanoma, leukemia, squamous cell carcinoma, nasopharyngeal carcinoma, glioblastoma, pancreatic ductal adenocarcinoma, acute myeloid leukemia or obesity-induced hepatocellular carcinoma. A cancer can be acute myeloid leukemia.

A STAT3 inhibitor compound of the present disclosure can be for administration to the subject within a pharmaceutical composition. pharmaceutical composition is a mono-phasic pharmaceutical composition suitable for parenteral or oral administration consisting essentially of a therapeutically-effective amount of the compound, and a pharmaceutically acceptable additive.

In these methods, the compounds and/or pharmaceutical composition may be administered in combination with one or more additional therapeutic agents. Additional therapeutic agents can include, but are not limited to, chemotherapeutic agents, anti-cancer agents, DNA alkylating agents, DNA damage response (DDR) inhibitors, cell-cycle checkpoint inhibitors, PARP inhibitors, HDAC inhibitors, kinase inhibitors, Bcl-2 inhibitors, Mcl-1 inhibitors, PD-L1 targeted agents, immunotherapy agents and bioenergetics modulators. Additional therapeutic agents can include, but are not limited to cisplatin, cytarabine, doxorubicin, paclitaxel, temozolomide, dasatinib, nilotinib, fluvestrant, venetoclax, metformin, or combinations thereof.

This Summary is neither intended nor should it be construed as being representative of the full extent and scope of the present disclosure. Moreover, references made herein to "the present disclosure," or aspects thereof, should be understood to mean certain embodiments of the present disclosure and should not necessarily be construed as limiting all embodiments to a particular description. The present disclosure is set forth in various levels of detail in this Summary as well as in the attached drawings and the Description of Embodiments and no limitation as to the scope of the present disclosure is intended by either the inclusion or non-inclusion of elements, components, etc. in this Summary. Additional aspects of the present disclosure will become readily apparent from the Description of Embodiments, particularly when taken together with the drawings.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Other features and advantages of the disclosure will be apparent from the following detailed description and claims.

DESCRIPTION OF EMBODIMENTS

Figure 1A:
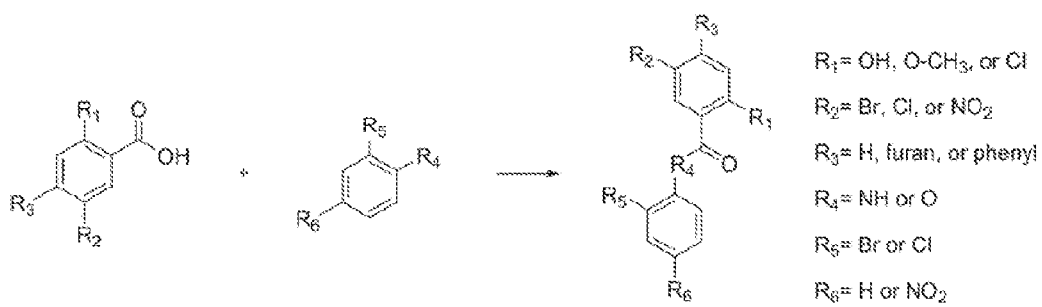
FIG. 1A shows structures of synthesized niclosamide analogs and a general synthesis method under microwave irradiation conditions.

The present disclosure is drawn to STAT3 transcription factor inhibitors that demonstrate efficacy in the treatment of solid tumors and blood cancers.

Definitions

To facilitate an understanding of the embodiments presented, the following definitions are provided.

The singular terms "a," "an," and "the" include plural referents unless context clearly indicates otherwise. Similarly, the word "or" is intended to include "and" unless the context clearly indicates otherwise. The term "comprises" means "includes." Also, "comprising A or B" means including A or B, or A and B, unless the context clearly indicates otherwise. It is to be further understood that all molecular weight or molecular mass values given for compounds are approximate, and are provided for description. Although methods and materials similar or equivalent to those described herein can be used in the practice or testing of this disclosure, suitable methods and materials are described below. In addition, the materials, methods, and examples are illustrative only and not intended to be limiting.

"Administration of" and "administering a" compound or agent should be understood to mean providing a compound or agent, a prodrug of a compound or agent, or a pharmaceutical composition as described herein. The compound, agent or composition can be administered by another person to the subject (e.g., intravenously) or it can be self-administered by the subject (e.g., tablets or capsules).

The term "subject" refers to mammals (for example, humans and veterinary animals such as dogs, cats, pigs, horses, sheep, and cattle).

An "R-group" or "substituent" refers to a single atom (for example, a halogen atom) or a group of two or more atoms that are covalently bonded to each other, which are covalently bonded to an atom or atoms in a molecule to satisfy the valency requirements of the atom or atoms of the molecule, typically in place of a hydrogen atom. Examples of R-groups/substituents include alkyl groups, hydroxyl groups, alkoxy groups, acyloxy groups, mercapto groups, and aryl groups.

"Substituted" or "substitution" refer to replacement of a hydrogen atom of a molecule or an R-group with one or more additional R-groups such as halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, nitro, sulfato, or other R-groups.

"Acyl" refers to a group having the structure RCO—, where R may be alkyl, or substituted alkyl. "Lower acyl" groups are those that contain one to six carbon atoms.

"Acyloxy refers to a group having the structure RCOO—, where R may be alkyl or substituted alkyl. "Lower acyloxy" groups contain one to six carbon atoms.

"Alkenyl" refers to a cyclic, branched or straight chain group containing only carbon and hydrogen, and unless otherwise mentioned typically contains one to twelve carbon atoms, and contains one or more double bonds that may or may not be conjugated. Alkenyl groups may be unsubstituted or substituted. "Lower alkenyl" groups contain one to six carbon atoms.

The term "alkoxy" refers to a straight, branched or cyclic hydrocarbon configuration and combinations thereof, including from 1 to 20 carbon atoms, preferably from 1 to 8 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or $(C_1-C_6)$alkyl can be methyl, ethyl, propyl, isopropyl, butyl, isobutyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, isobutoxy, sec-butoxy, pentoxy, 3-pentoxy, or hexyloxy; $(C_2-C_6)$alkenyl can be vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl; $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; $(C_1-C_6)$ alkanoyl can be acetyl, propanoyl or butanoyl; halo$(C_1-C_6)$ alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$ alkanoyloxy can be acetoxy, propanoyloxy, butanoyloxy, isobutanoyloxy, pentanoyloxy, or hexanoyloxy.

"Alkynyl" refers to a cyclic, branched or straight chain group containing only carbon and hydrogen, and unless otherwise mentioned typically contains one to twelve carbon atoms, and contains one or more triple bonds. Alkynyl groups may be unsubstituted or substituted. "Lower alkynyl" groups are those that contain one to six carbon atoms.

The term "halogen" refers to fluoro, bromo, chloro, and iodo substituents.

"Aryl" refers to a monovalent unsaturated aromatic carbocyclic group having a single ring (e.g., phenyl) or multiple condensed rings (e.g., naphthyl or anthryl), which can optionally be unsubstituted or substituted.

The term "amino" refers to an R-group having the structure $—NH_2$, which can be optionally substituted with, for example, lower alkyl groups, to yield an amino group having the general structure —NHR or $—NR_2$.

"Nitro" refers to an R-group having the structure $—NO_2$.

The term "aliphatic" as applied to cyclic groups refers to ring structures in which any double bonds that are present in the ring are not conjugated around the entire ring structure.

The term "aromatic" as applied to cyclic groups refers to ring structures which contain double bonds that are conjugated around the entire ring structure, possibly through a heteroatom such as an oxygen atom or a nitrogen atom. Aryl groups, pyridyl groups and furan groups are examples of aromatic groups. The conjugated system of an aromatic group contains a characteristic number of electrons, for example, 6 or 10 electrons that occupy the electronic orbitals making up the conjugated system, which are typically un-hybridized p-orbitals.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's Pharmaceutical Sciences, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid, and the like.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned above are meant to comprise the therapeutically active non-toxic acid and base addition salt forms which the compounds can form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic, and like acids. Conversely, these salt forms can be converted into the free base form by treatment with an appropriate base.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine, and the like.

Some of the compounds described herein may also exist in their tautomeric form.

A "therapeutically effective amount" of the disclosed compounds is a dosage of the compound that is sufficient to achieve a desired therapeutic effect, such as inhibition of inflammation, angiogenesis, or an anti-tumor or anti-metastatic effect. In some examples, a therapeutically effective amount is an amount sufficient to achieve tissue concentrations at the site of action that are similar to those that are shown to modulate angiogenesis, NF-kappaB activity, or immune cytokines, in tissue culture, in vitro, or in vivo. For example, a therapeutically effective amount of a compound may be such that the subject receives a dosage of about 0.1 μg/kg body weight/day to about 1000 mg/kg body weight/day, for example, a dosage of about 1 μg/kg body weight/day to about 1000 μg/kg body weight/day, such as a dosage of about 5 μg/kg body weight/day to about 500 μg/kg body weight/day.

The term "stereoisomer" refers to a molecule that is an enantiomer, diastereomer or geometric isomer of a molecule. Stereoisomers, unlike structural isomers, do not differ with respect to the number and types of atoms in the molecule's structure but with respect to the spatial arrangement of the molecule's atoms. Examples of stereoisomers include the (+) and (−) forms of optically active molecules.

The term "modulate" refers to the ability of a disclosed compound to alter the amount, degree, or rate of a biological function, the progression of a disease, or amelioration of a condition. For example, modulating can refer to the ability of a compound to elicit an increase or decrease in angiogenesis, to inhibit TNF-alpha activity, or to inhibit tumor metastasis or tumorigenesis.

The term "angiogenic activity" refers to the ability of a disclosed compound or a particular concentration of a disclosed compound to stimulate angiogenesis. Angiogenic activity may be detected in vivo or in vitro. Angiogenic compounds or angiogenic concentrations of disclosed compounds stimulate angiogenesis, and such compounds and/or concentrations may be readily identified by those of ordinary skill in the art, using, for example, the methods described in the Examples that follow.

The term "anti-angiogenic activity" refers to the ability of a compound or a particular concentration of a disclosed compound to inhibit angiogenesis. Anti-angiogenic activity may be detected in vivo or in vitro. Anti-angiogenic or anti-angiogenic concentrations of disclosed compounds inhibit angiogenesis, and such compounds and/or concentrations may be readily identified by those of ordinary skill in the art, using, for example, the methods described in the Examples that follow.

"Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" is inclusive of inhibiting the full development of a disease or condition, for example, in a subject who is at risk for a disease, or who has a disease, such as cancer or a disease associated with a compromised immune system. "Preventing" a disease or condition refers to prophylactically administering a composition to a subject who does not exhibit signs of a disease or exhibits only early signs of the disease, for the purpose of decreasing the risk of developing a pathology or condition, or diminishing the severity of a pathology or condition.

As used herein, a "prodrug" is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability, and are readily metabolized into the active STAT3 inhibitors in vivo. Prodrugs of compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. For a general discussion of prodrugs involving esters see Svensson and Tunek, *Drug Metabolism Reviews* 165 (1988) and Bundgaard, *Design of Prodrugs*, Elsevier (1985).

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999. In general, protecting groups are removed under conditions which will not affect the remaining portion of the molecule. These methods are well known in the art and include acid hydrolysis, hydrogenolysis, and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Particular examples of the presently disclosed compounds include one or more asymmetric centers. Thus, these compounds can exist in different stereoisomeric forms. Accordingly, compounds and compositions may be provided as individual pure enantiomers or as stereoisomeric mixtures, including racemic mixtures. The compounds disclosed herein may be synthesized in, or are purified to be in, substantially enantiopure form, such as in a 90% enantiomeric excess, a 95% enantiomeric excess, a 97% enantiomeric excess or even in greater than a 99% enantiomeric excess, such as in enantiopure form.

Groups which are substituted (e.g. substituted alkyl), may in some embodiments be substituted with a group which is itself substituted (e.g. substituted aryl). In some embodiments, the number of substituted groups linked together is limited to two (e.g. substituted alkyl is substituted with substituted aryl, wherein the substituent present on the aryl is not further substituted). In exemplary embodiments, a substituted group is not substituted with another substituted group (e.g. substituted alkyl is substituted with unsubstituted aryl).

Compounds of the Present Disclosure

One aspect of this disclosure are compounds that inhibit STAT3 transcription factor with specificity for STAT3 over other STAT family (i.e., STAT1, STAT2, STAT4, STAT5A, STAT5B, and STAT6) transcription factors and can therefore be used to treat a wide variety of tumors and blood cancers. Pharmaceutically acceptable salts, prodrugs, stereoisomers, and metabolites of all the STAT3 inhibitor compounds of this disclosure also are contemplated.

In some aspects, the present disclosure provides a compound of Formula (I) or (II):

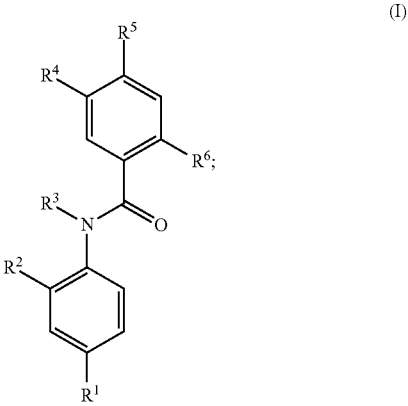

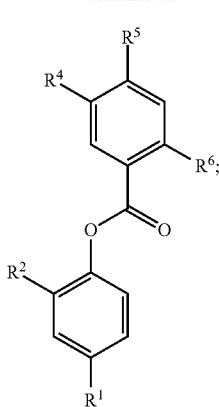

(II)

or a pharmaceutically acceptable salt thereof, wherein:
- $R^1$ is H, $C_{1-6}$ alkyl, substituted $C_{1-6}$ alkyl, $C_{1-6}$ alkoxy, aryl, substituted aryl, heteroaryl, substituted heteroaryl, nitro, CN, $SO_3H$, OR where $R^{1S}$ is H, $C_{1-6}$ alkyl, substituted $C_{1-6}$ alkyl, $C_{3-8}$ cycloalkyl, aryl, substituted aryl, heteroaryl, substituted heteroaryl, or $NR^{1Sa}R^{1Sb}$ where $R^{1Sa}$ and $R^{1Sb}$ are independently H, $C_{1-8}$ alkyl, substituted $C_{1-8}$ alkyl, $C_{3-8}$ cycloalkyl, $C_{2-4}$ alkenyl, aryl such as a phenyl, substituted aryl, heteroaryl or substituted heteroaryl;
- $R^2$ is H, C1-6 alkyl, substituted $C_{1-6}$ alkyl, $C_{1-6}$ alkoxy, aryl, substituted aryl, heteroaryl, substituted heteroaryl, halogen, $OR^{2S}$ where $R^{2S}$ is H, $C_{1-6}$ alkyl, substituted $C_{1-6}$ alkyl, $C_{3-8}$ cycloalkyl, aryl, substituted aryl, heteroaryl, substituted heteroaryl, or $NR^{2Sa}R^{2Sb}$ where $R^{2Sa}$ and $R^{2Sb}$ are independently H, $C_{1-8}$ alkyl, substituted $C_{1-8}$ alkyl, $C_{3-8}$ cycloalkyl, $C_{2-4}$ alkenyl, aryl such as a phenyl, substituted aryl, heteroaryl or substituted heteroaryl;
- $R^3$ is H, $C_{1-6}$ alkyl, substituted $C_{1-6}$ alkyl, aryl, substituted aryl, heteroaryl, or substituted heteroaryl;
- $R^4$ is H, $C_{1-6}$ alkyl, substituted $C_{1-6}$ alkyl, $C_{1-6}$ alkoxy, aryl, substituted aryl, heteroaryl, substituted heteroaryl, halogen, nitro, $OR^{4S}$ where $R^{4S}$ is H, $C_{1-6}$ alkyl, substituted $C_{1-6}$ alkyl, $C_{3-8}$ cycloalkyl, aryl, substituted aryl, heteroaryl, substituted heteroaryl, or $NR^{4Sa}R^{4Sb}$ where $R^{4Sa}$ and $R^{4Sb}$ are independently H, $C_{1-8}$ alkyl, substituted $C_{1-8}$ alkyl, $C_{3-8}$ cycloalkyl, $C_{2-4}$ alkenyl, aryl such as a phenyl, substituted aryl, heteroaryl or substituted heteroaryl;
- $R^5$ is H, $C_{1-6}$ alkyl, substituted $C_{1-6}$ alkyl, $C_{1-6}$ alkoxy, aryl, substituted aryl, heteroaryl, substituted heteroaryl, $OR^{5S}$ where $R^{5S}$ is H, $C_{1-6}$ alkyl, substituted $C_{1-6}$ alkyl, $C_{3-8}$ cycloalkyl, aryl, substituted aryl, heteroaryl, substituted heteroaryl, or $NR^{5Sa}R^{5Sb}$ where $R^{5Sa}$ and $R^{5Sb}$ are independently H, $C_{1-8}$ alkyl, substituted $C_{1-8}$ alkyl, $C_{3-8}$ cycloalkyl, $C_{2-4}$ alkenyl, aryl such as a phenyl, substituted aryl, heteroaryl or substituted heteroaryl; and
- $R^6$ is H, $C_{1-6}$ alkyl, substituted $C_{1-6}$ alkyl, $C_{1-6}$ alkoxy, aryl, substituted aryl, heteroaryl, substituted heteroaryl, halogen, $OR^{6S}$, or —C(=O)—$OR^{6S}$ where $R^{6S}$ is H, $C_{1-6}$ alkyl, —C(=O)—$C_{1-6}$ alkyl, substituted $C_{1-6}$ alkyl, $C_{3-8}$ cycloalkyl, aryl, substituted aryl, heteroaryl, substituted heteroaryl, or $NR^{6Sa}R^{6Sb}$ where $R^{6Sb}$ are independently H, $C_{1-8}$ alkyl, substituted $C_{1-8}$ alkyl, $C_{3-8}$ cycloalkyl, $C_{2-4}$ alkenyl, aryl such as a phenyl, substituted aryl, heteroaryl or substituted heteroaryl.

In some aspects, the present disclosure provides a compound of Formula (I) or (II):

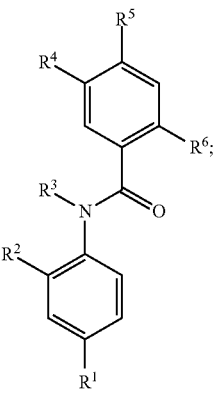

(I)

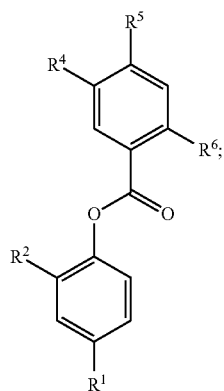

(II)

or a pharmaceutically acceptable salt thereof, wherein:
- $R^1$ is H, nitro, or $NH_2$;
- $R^2$ is halogen;
- $R^3$ is H or $C_{1-6}$ alkyl;
- $R^4$ is halogen, nitro, or $NH_2$;
- $R^5$ is H, $C_6$-$C_{12}$ aryl, or 5- to 12-membered heteroaryl, wherein the $C_6$-$C_{12}$ aryl or 5- to 12-membered is optionally substituted with one or more $R^{5S}$;
- each $R^{5S}$ independently is halogen, $C_{1-6}$ alkyl, —$OR^{5SS}$, —$N(R^{5SS})_2$, ($C_{1-6}$ alkyl)-$OR^{5SS}$, —($C_{1-6}$ alkyl)-N($R^{5SS}$)$_2$, —C(=O)—$R^{5SS}$, or —C(=O)—$OR^{5SS}$;
- each $R^{5SS}$ independently is H or $C_{1-6}$ alkyl;
- $R^6$ is halogen, Or, or —C(=O)—$OR^{6S}$; and
- $R^{6S}$ is H, $C_{1-6}$ alkyl, or —C(=O)—$C_{1-6}$ alkyl.

In some aspects, the present disclosure provides a compound of Formula (I) or (II):

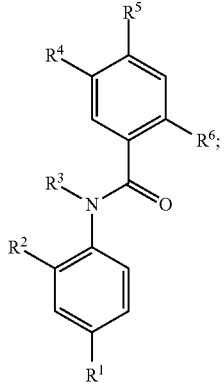
(I)

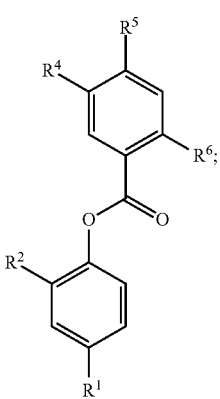
(II)

or a pharmaceutically acceptable salt thereof, wherein:
R$^1$ is H, nitro, CN, SO$_3$H, —C(=O)—OR$^{1S}$, —(C=O)—N(R$^{1S}$)$_2$, or N(R$^{1S}$)$_2$;
each R$^{1S}$ independently is H or C$_{1-6}$ alkyl;
R$^2$ is halogen;
R$^3$ is H or C$_{1-6}$ alkyl;
R$^4$ is halogen, nitro, or NH$_2$;
R$^5$ is H, C$_6$-C$_{12}$ aryl, or 5- to 12-membered heteroaryl, wherein the C$_6$-C$_{12}$ aryl or 5- to 12-membered is optionally substituted with one or more R$^{5S}$;
each R$^{5S}$ independently is halogen, C$_{1-6}$ alkyl, —OR$^{5SS}$, —N(R$^{5SS}$)$_2$, —(C$_{1-6}$ alkyl)-OR$^{5SS}$, —(C$_{1-6}$ alkyl)-N(R$^{5SS}$)$_2$, —C(=O)—R$^{5SS}$, or —C(=O)—OR$^{5SS}$;
each R$^{5SS}$ independently is H or C$_{1-6}$ alkyl;
R$^6$ is halogen, OR$^{6S}$, or —C(=O)—OR$^{6S}$; and
R$^{6S}$ is H, C$_{1-6}$ alkyl, or —C(=O)—C$_{1-6}$ alkyl.

In some embodiments, the compound is of Formula (I):

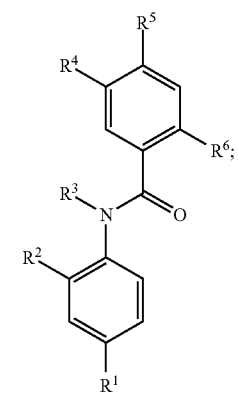
(I)

or a pharmaceutically acceptable salt thereof, wherein:
R$^1$ is nitro, CN, SO$_3$H, —C(=O)—OR$^{1S}$, —(C=O)—N(R$^{1S}$)$_2$, or N(R$^{1S}$)$_2$;
each R$^{1S}$ independently is H or C$_{1-6}$ alkyl;
R$^2$ is halogen;
R$^3$ is H or C$_{1-6}$ alkyl;
R$^4$ is halogen;
R$^5$ is 5- to 12-membered heteroaryl optionally substituted with one or more R$^{5S}$;
each R$^{5S}$ independently is halogen, C$_{1-6}$ alkyl, —OR$^{5SS}$, —N(R$^{5SS}$)$_2$, —(C$_{1-6}$ alkyl)-OR$^{5SS}$, —(C$_{1-6}$ alkyl)-N(R$^{5SS}$)$_2$, —C(=O)—R$^{5SS}$, or —C(=O)—OR$^{5SS}$;
each R$^{5SS}$ independently is H or C$_{1-6}$ alkyl;
R$^6$ is OR$^{6S}$ or —C(=O)—OR$^{6S}$; and
R$^{6S}$ is H or —C(=O)—C$_{1-6}$ alkyl.

In some embodiments, the compound is of Formula (I-a):

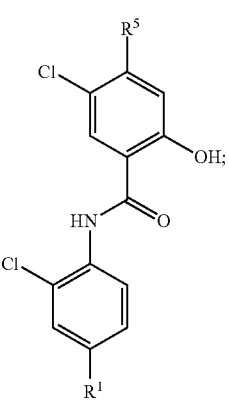
(I)

or a pharmaceutically acceptable salt thereof, wherein:
R$^1$ is nitro, CN, SO$_3$H, —C(=O)—OR$^{1S}$, —(C=O)—N(R$^{1S}$)$_2$, or N(R$^{1S}$)$_2$;
each R$^{1S}$ independently is H or C$_{1-6}$ alkyl;
R$^5$ is 5- to 12-membered heteroaryl optionally substituted with one or more R$^{5S}$;
each R$^{5S}$ independently is halogen, C$_{1-6}$ alkyl, —OR$^{5SS}$, —N(R$^{5SS}$)$_2$, —(C$_{1-6}$ alkyl)-OR$^{5SS}$, —(C$_{1-6}$ alkyl)-N(R$^{5SS}$)$_2$, —C(=O)—R$^{5SS}$, or —C(=O)—OR$^{5SS}$; and
each R$^{5SS}$ independently is H or C$_{1-6}$ alkyl.

In some embodiments, the compound is not niclosamide.
In some embodiments, the compound is not niclosamide or a pharmaceutically acceptable salt thereof.

In some embodiments, $R^1$ is nitro, CN, $SO_3H$, —C(=O)—$OR^{1S}$, —(C=O)—$N(R^{1S})_2$, or $N(R^{1S})_2$. In some embodiments, $R^1$ is nitro. In some embodiments, $R^1$ is CN. In some embodiments, $R^1$ is $SO_3H$. In some embodiments, $R^1$ is —C(=O)—$OR^{1S}$. In some embodiments, $R^1$ is —C(=O)—OH. In some embodiments, $R^1$ is —(C=O)—$N(R^{1S})_2$. In some embodiments, $R^1$ is —(C=O)—$NH_2$. In some embodiments, $R^1$ is $N(R^{1S})_2$. In some embodiments, $R^1$ is $N(CH_3)_2$.

In some embodiments, each $R^{1S}$ is H. In some embodiments, each $R^{1S}$ is $C_{1-6}$ alkyl. In some embodiments, each $R^{1S}$ is $CH_3$.

In some embodiments, $R^2$ is halogen (e.g., F, Cl, or Br). In some embodiments, $R^2$ is F. In some embodiments, $R^2$ is Cl. In some embodiments, $R^2$ is Br.

In some embodiments, $R^3$ is H or $C_{1-6}$ alkyl. In some embodiments, $R^3$ is H. In some embodiments, $R^3$ is $C_{1-6}$ alkyl. In some embodiments, $R^3$ is $CH_3$.

In some embodiments, $R^4$ is halogen, nitro, or $NH_2$. In some embodiments, $R^4$ is halogen (e.g., F, Cl, or Br). In some embodiments, $R^4$ is F. In some embodiments, $R^4$ is Cl. In some embodiments, $R^4$ is Br. In some embodiments, $R^4$ is nitro. In some embodiments, $R^4$ is $NH_2$.

In some embodiments, $R^5$ is 5- to 12-membered heteroaryl optionally substituted with one or more $R^{5S}$.

In some embodiments, $R^5$ is 5-membered heteroaryl optionally substituted with one or more $R^{5S}$. In some embodiments, $R^5$ is furanyl, imidazolyl, or oxazolyl, wherein the furanyl, imidazolyl, or oxazolyl is optionally substituted with one or more $R^{5S}$. In some embodiments, $R^5$ is furanyl, imidazolyl, or oxazolyl. In some embodiments, $R^5$ is furanyl optionally substituted with one or more $R^{5S}$. In some embodiments, $R^5$ is imidazolyl optionally substituted with one or more $R^{5S}$. In some embodiments, $R^5$ is oxazolyl optionally substituted with one or more $R^{5S}$.

In some embodiments $R^5$ is 9-membered heteroaryl optionally substituted with one or more $R^{5S}$. In some embodiments $R^5$ is benzofuranyl optionally substituted with one or more $R^{5S}$.

In some embodiments, at least one $R^{5S}$ is halogen (e.g., F, Cl, Br).

In some embodiments, at least one $R^{5S}$ is $C_{1-6}$ alkyl. In some embodiments, at least one $R^{5S}$ is —$OR^{5SS}$ (e.g., —OH or —$OCH_3$). In some embodiments, at least one $R^{5S}$ is —$N(R^{5SS})_2$ (e.g., —$NH_2$ or —$NCH_3)_2$). In some embodiments, at least one $R^{5S}$ is —($C_{1-6}$ alkyl)-$OR^{5SS}$. In some embodiments, at least one $R^{5S}$ is —($C_{1-6}$ alkyl)-$N(R^{5SS})_2$. In some embodiments, at least one $R^{5S}$ is —C(=O)—$R^{5SS}$. In some embodiments, at least one $R^{5S}$ is C(=O)—$OR^{5SS}$.

In some embodiments, each $R^{5SS}$ is H. In some embodiments, each $R^{5SS}$ is $C_{1-6}$ alkyl. In some embodiments, each $R^{5SS}$ is $CH_3$.

In some embodiments, $R^6$ is $OR^{6S}$. In some embodiments, In some embodiments, $R^6$ is —OH. In some embodiments, $R^6$ is —O—C(=O)—$C_{1-6}$ alkyl.

In some embodiments, $R^6$ is —C(=O)—$OR^{6S}$. In some embodiments, $R^6$ is —C(=O)—OH. In some embodiments, $R^6$ is —C(=O)—O—$C_{1-6}$ alkyl.

In some embodiments, $R^{6S}$ is H. In some embodiments, $R^{6S}$ is —C(=O)—$C_{1-6}$ alkyl.

It is understood that, for a compound of any one of the formulae described herein, $R^1$, $R^2$, $R^3$, $R^4$, $R^5$, and $R^6$ can each be, where applicable, selected from the groups described herein, and any group described herein for any of $R^1$, $R^2$, $R^3$, $R^4$, $R^5$, and $R^6$ can be combined, where applicable, with any group described herein for one or more of the remainder of $R^1$, $R^2$, $R^3$, $R^4$, $R^5$, and $R^6$.

In some embodiments, the compound is selected from:

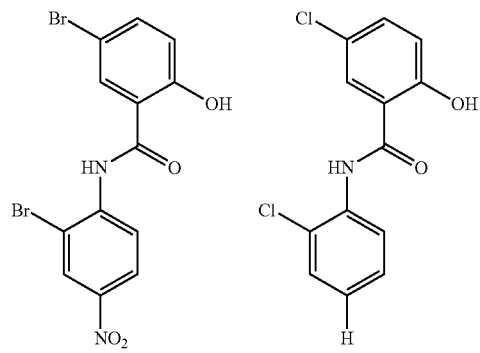

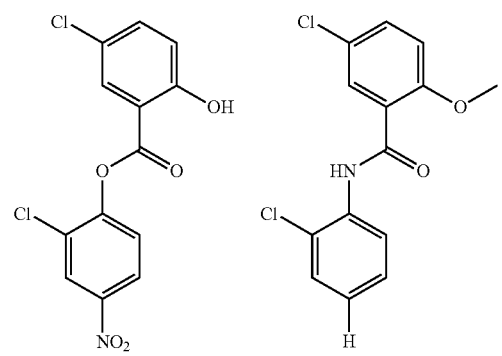

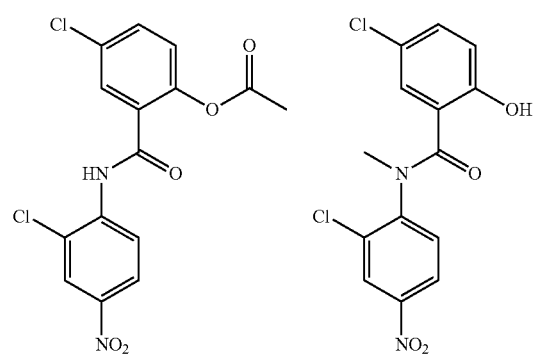

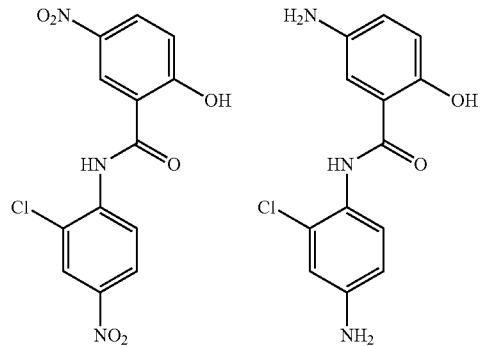

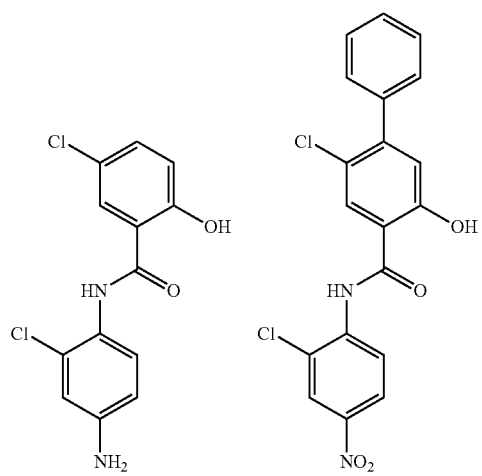
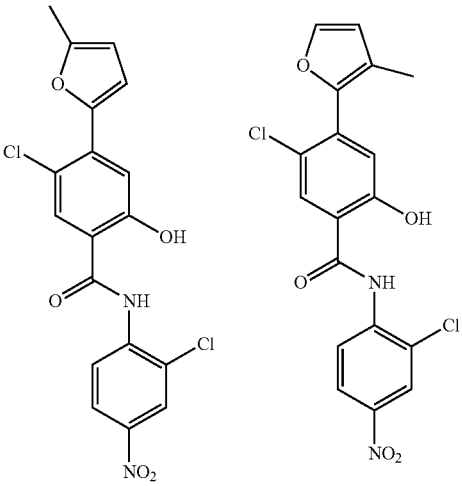
prodrugs thereof, and pharmaceutically acceptable salts thereof.
In some embodiments, the compound is selected from:
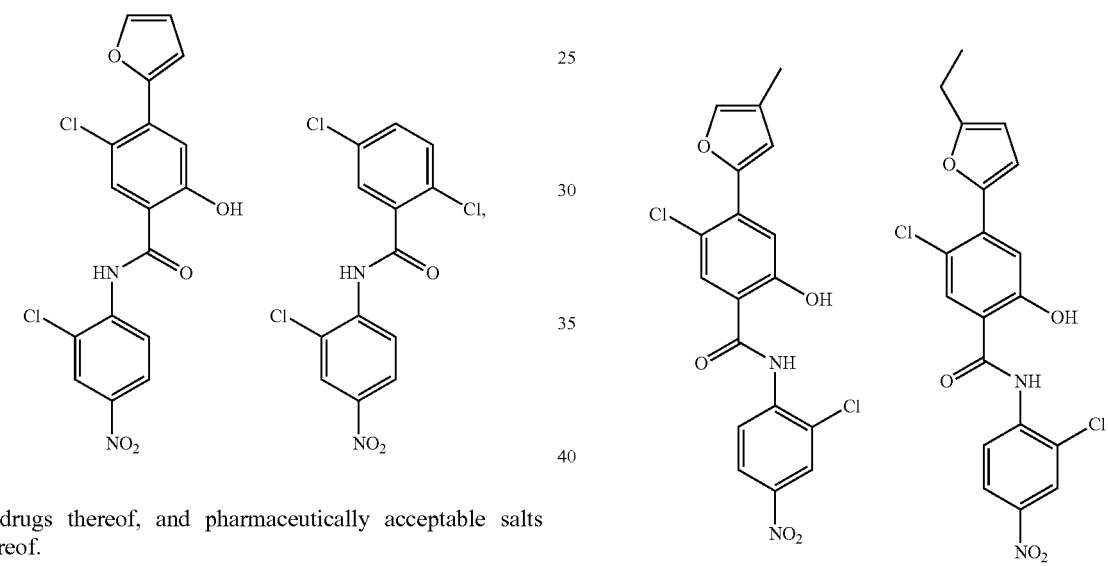
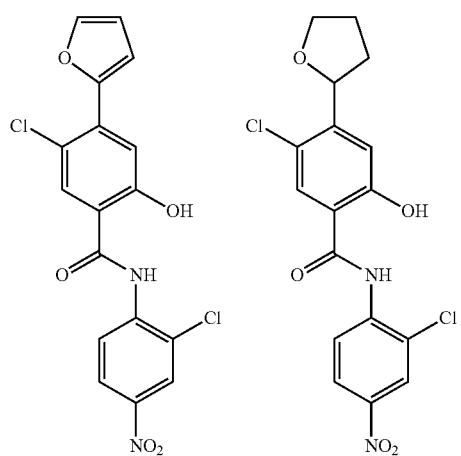
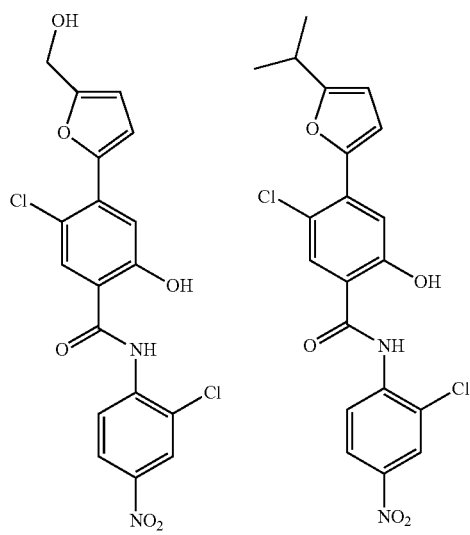

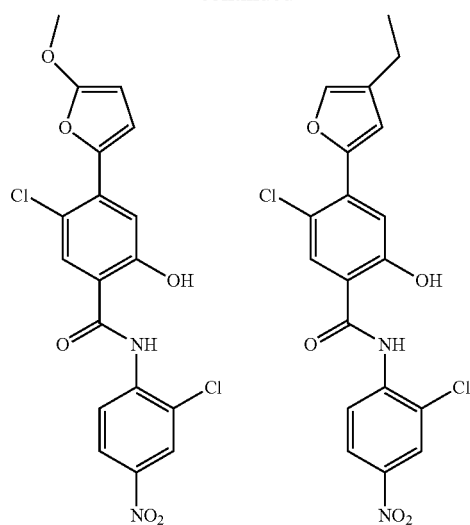
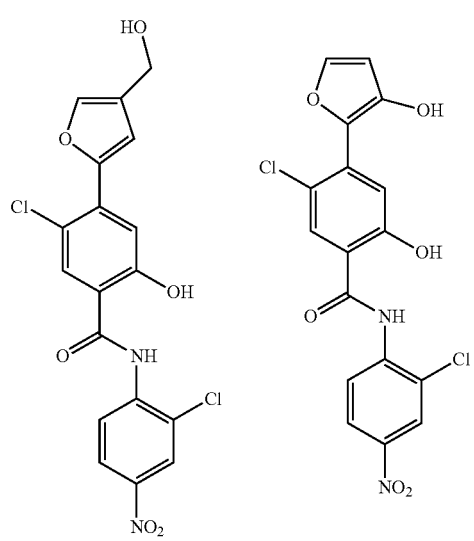
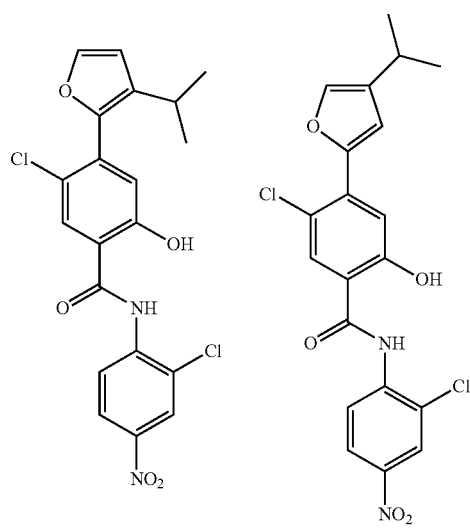
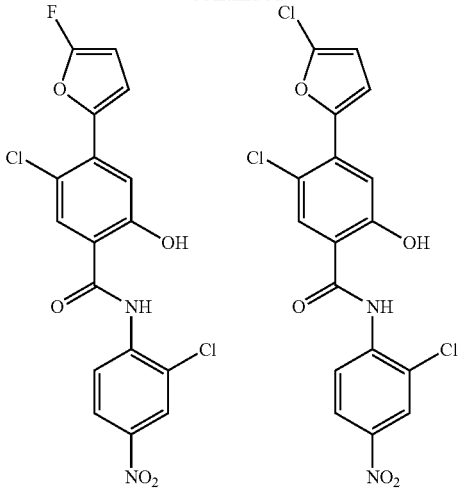
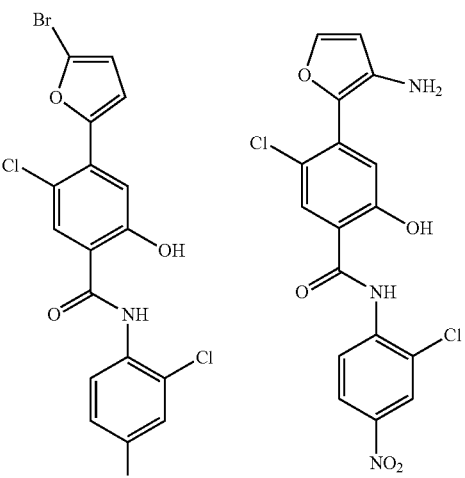
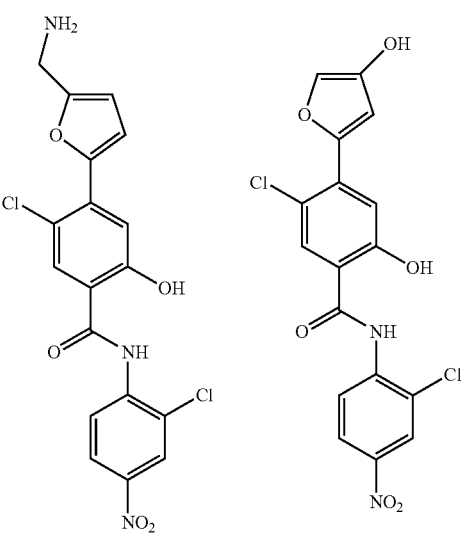

-continued
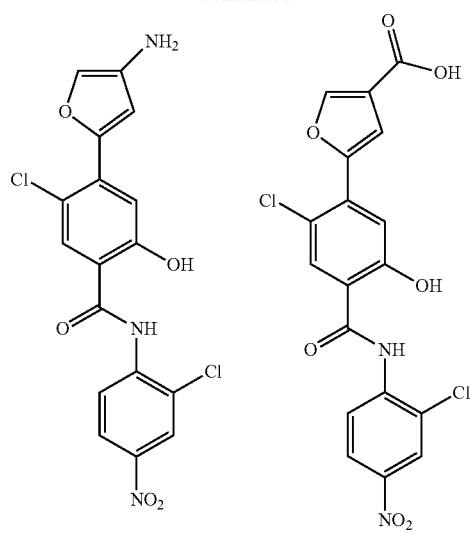 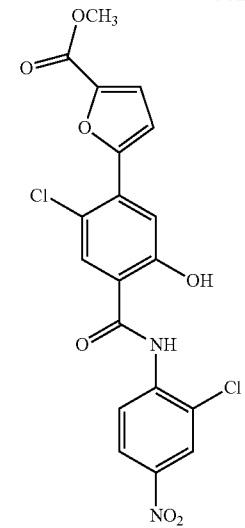 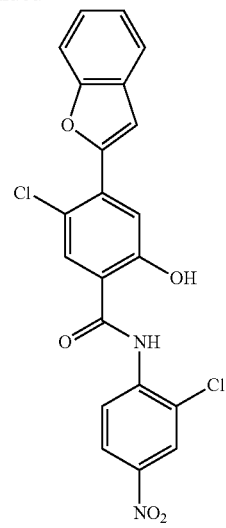
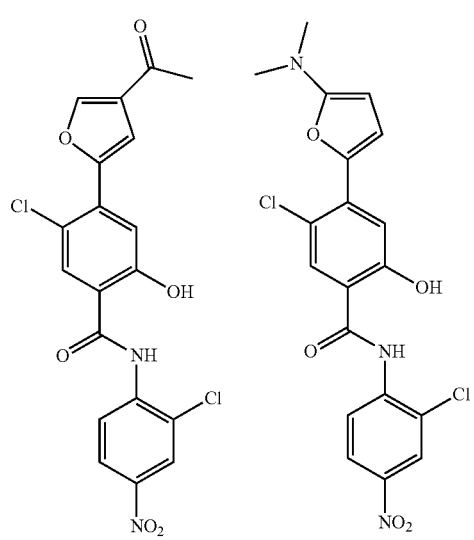 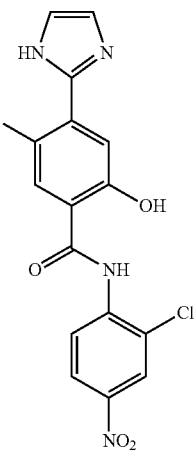
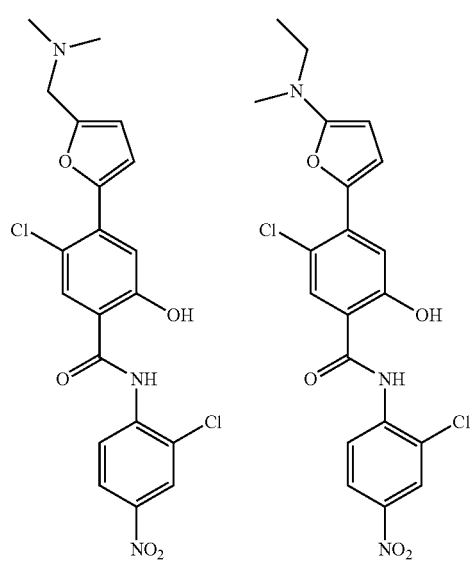 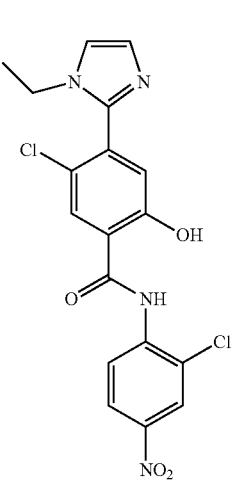

-continued

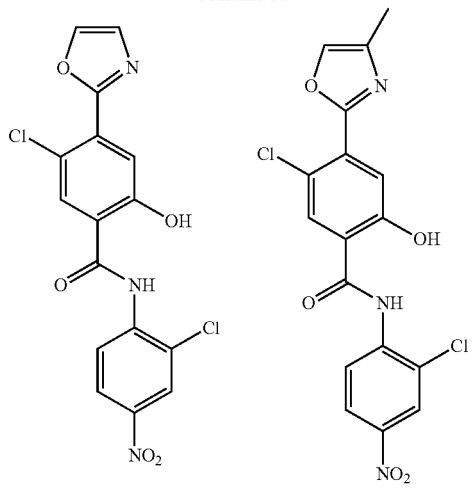

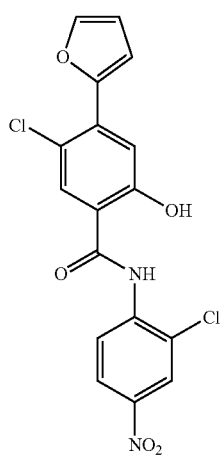 [SMILES: O=C(Nc1ccc([N+](=O)[O-])cc1Cl)c1cc(Cl)c(-c2ccco2)cc1O]

prodrugs thereof, and pharmaceutically acceptable salts thereof.

In some embodiments, the compound is

In some embodiments, the compound is

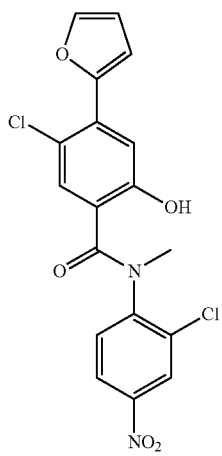 [SMILES: CN(C(=O)c1cc(Cl)c(-c2ccco2)cc1O)c1ccc([N+](=O)[O-])cc1Cl]

or a pharmaceutically acceptable salt thereof.

In some embodiments, the compound is

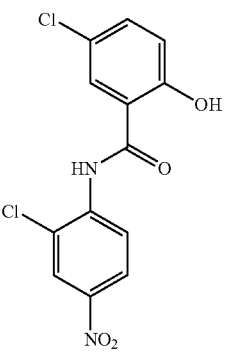 [SMILES: O=C(Nc1ccc([N+](=O)[O-])cc1Cl)c1cc(Cl)ccc1O]

or a pharmaceutically acceptable salt thereof.

In some embodiments, the compound is an isotopic derivative of any one of the compounds described herein and pharmaceutically acceptable salts thereof.

In some embodiments, the compound is an isotopic derivative of any one of the compounds described herein.

It is understood that the isotopic derivative can be prepared using any of a variety of art-recognized techniques. For example, the isotopic derivative can generally be prepared by carrying out the procedures disclosed in the Schemes and/or in the Examples described herein, by substituting an isotopically labeled reagent for a non-isotopically labeled reagent.

In some embodiments, the isotopic derivative is a deuterium labeled compound.

In some embodiments, the isotopic derivative is a deuterium labeled compound of any one of the compounds described herein and pharmaceutically acceptable salts thereof.

In some embodiments, the isotopic derivative is a deuterium labeled compound of any one of the compounds described herein.

The term "isotopic derivative", as used herein, refers to a derivative of a compound in which one or more atoms are isotopically enriched or labelled. In some embodiments, the isotopic derivative is enriched with regard to, or labelled with, one or more atoms selected from $^2H$, $^{13}C$, $^{14}C$, $^{15}N$, and $^{18}O$. In some embodiments, the isotopic derivative is a deuterium labeled compound (i.e., being enriched with $^2$H with regard to one or more atoms thereof).

It is understood that the deuterium labeled compound can be prepared using any of a variety of art-recognized techniques. For example, the deuterium labeled compound can generally be prepared by carrying out the procedures disclosed in the Schemes and/or in the Examples described herein, by substituting a deuterium labeled reagent for a non-deuterium labeled reagent.

Methods of Synthesis

In some aspects, the present disclosure provides a method of preparing a compound of the present disclosure.

In some aspects, the present disclosure provides a method of a compound, comprising one or more steps as described herein.

In some aspects, the present disclosure provides a compound obtainable by, or obtained by, or directly obtained by a method for preparing a compound as described herein.

In some aspects, the present disclosure provides an intermediate as described herein, being suitable for use in a method for preparing a compound as described herein.

The compounds of the present disclosure can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

As will be understood by the person skilled in the art of organic synthesis, compounds of the present disclosure are readily accessible by various synthetic routes, some of which are exemplified in the accompanying examples. The skilled person will easily recognise which kind of reagents and reactions conditions are to be used and how they are to be applied and adapted in any particular instance—wherever necessary or useful—in order to obtain the compounds of the present disclosure. Furthermore, some of the compounds of the present disclosure can readily be synthesised by reacting other compounds of the present disclosure under suitable conditions, for instance, by converting one particular functional group being present in a compound of the present disclosure, or a suitable precursor molecule thereof, into another one by applying standard synthetic methods, like reduction, oxidation, addition or substitution reactions; those methods are well known to the skilled person. Likewise, the skilled person will apply—whenever necessary or useful—synthetic protecting (or protective) groups; suitable protecting groups as well as methods for introducing and removing them are well-known to the person skilled in the art of chemical synthesis and are described, in more detail, in, e.g., P. G. M. Wuts, T. W. Greene, "Greene's Protective Groups in Organic Synthesis", 4th edition (2006) (John Wiley & Sons).

Biological Assays

Compounds designed, selected and/or optimised by methods described above, once produced, can be characterised using a variety of assays known to those skilled in the art to determine whether the compounds have biological activity. For example, the molecules can be characterised by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

Various in vitro or in vivo biological assays are may be suitable for detecting the effect of the compounds of the present disclosure. These in vitro or in vivo biological assays can include, but are not limited to, enzymatic activity assays, electrophoretic mobility shift assays, reporter gene assays, in vitro cell viability assays, and the assays described herein.

Methods of Use

The STAT3 inhibitor compounds, disclosed herein may be used to prevent, treat, or ameliorate cancer, or prevent metastasis of cancer, in a subject by administering a therapeutically-effective amount of a compound of this disclosure that inhibits STAT3 transcription factor, in particular, the DNA binding activity of STAT3. For example, the disclosed compounds may be used to treat colorectal cancer, hepatocellular carcinoma, non-small cell lung cancer, ovarian cancer, prostate cancer, breast cancer (including triple negative breast cancer), T-cell lymphoma, Hodgkin's lymphoma, gastric cancer, skin cancer (esp. melanoma), leukemia, squamous cell carcinoma, nasopharyngeal carcinoma, glioblastoma, pancreatic ductal adenocarcinoma, and obesity-induced hepatocellular carcinoma.

These methods may also be used to prevent, treat, or ameliorate inflammation-induced carcinogenesis, including for example liver and gastric cancers arising from infections that cause chronic hepatitis, and colon cancer associated with Crohn's colitis and ulcerative colitis.

Therapeutically effective amounts of the disclosed compounds can be administered to a subject with a tumor to achieve an anti-tumor effect, such as inhibition of tumorigenesis or tumor metastasis. The disclosed compounds are also useful in the treatment of both primary and metastatic solid tumors. The disclosed compounds are also useful in treating hematopoietic malignancies such as leukemias (i.e. chloromas, plasmacytomas and the plaques and tumors of mycosis fungoides and cutaneous T-cell lymphoma/leukemia) as well as in the treatment of lymphomas (both Hodgkin's and non-Hodgkin's lymphomas). In addition, these compounds may be useful in the treatment of solid tumors arising from hematopoietic malignancies. In addition, these compounds may be useful in the prevention of metastases from the tumors described above either when used alone or in combination with radiotherapy and/or other chemotherapeutic agents. The compounds are also useful in treating multiple myeloma.

Further, a method for inhibiting the activity of the STAT3 transcription factor in a subject using the disclosed compounds is provided. The method includes administering a therapeutically effective amount of a disclosed compound to a subject to achieve a STAT3 inhibitory effect. The compounds of this disclosure having STAT3-inhibitory effects are useful for treating many inflammatory, infectious, immunological, and malignant diseases. These include, but are not limited to, cancer, tumor growth, undesirable angiogenesis, obesity, and autoimmune diseases such as rheumatoid arthritis.

STAT3 has been implicated in the maintenance and survival of cancer stem cells, and inducing and maintaining a pro-carcinogenic inflammatory microenvironment. Thus, further methods for inhibiting the activity of the STAT3 transcription factor in cancer stem cells and in cancer immunotherapy using the disclosed STAT3 inhibitor compounds is provided. These methods may be particularly effective in preventing metastases of a tumor in a patient and/or treating drug-resistant cancers in a patient, which may include sensitizing cancer cells to other anticancer drugs that may be administered in combination with the STAT3 inhibitors of this disclosure.

The disclosed compounds can be used in combination with other compositions and procedures for the treatment of diseases. For example, a cancer may be treated conventionally with surgery, radiation or chemotherapy in combination with one or more of the STAT3 transcription factor inhibitor compounds disclosed herein. Additionally, a cancer may be treated conventionally with a chemotherapeutic and one or more of the STAT3 transcription factor inhibitor compounds disclosed herein may be administered to reduce chemotherapeutic drug resistance of the cancer cells to the conventional chemotherapeutic.

The disclosed compounds exhibiting STAT3-inhibitory activity may be combined with other anti-cancer and/or anti-inflammatory agents. The disclosed compounds exhibiting STAT3-inhibitory activity may be combined with other conventional anticancer therapies, for example, steroids such as dexamethasone and prednisolone.

Examples of other chemotherapeutic agents that can be used in combination with the disclosed STAT3 inhibitory compounds include, but are not limited to, DNA alkylating agents and HDAC inhibitors. Specific examples include, but are not limited to, cisplatin, doxorubicin, paclitaxel, fluvestrant, metformin, or combinations thereof. Examples of additional therapeutic agents that can be used in combination with the disclosed STAT3 inhibitor compounds include, but are not limited to, chemotherapeutic agents, anti-cancer agents, DNA alkylating agents, DNA damage response (DDR) inhibitors, cell-cycle checkpoint inhibitors, PARP inhibitors, HDAC inhibitors, kinase inhibitors, Bcl-2 inhibitors, Mcl-1 inhibitors, PD-L1 targeted agents, immunotherapy agents and bioenergetics modulators. Additional therapeutic agents can include, but are not limited to cisplatin, cytarabine, doxorubicin, paclitaxel, temozolomide, dasatinib, nilotinib, fluvestrant, venetoclax, metformin, or combinations thereof.

The disclosed compounds also may be combined with radiotherapy employing radioisotopes (such as $^{32}$P, $^{90}$Y, $^{125}$I, $^{131}$I and $^{177}$Lu), particle beams (such as proton, neutron and electron beams) and electromagnetic radiation (such as gamma rays, x-rays and photodynamic therapy using photosensitizers and visible or ultraviolet rays).

The present disclosure provides a method of treating cancer in a subject comprising administering to the subject at least one therapeutically effective amount of at least one compound of the present disclosure. The present disclosure provides at least one compound of the present disclosure for use in the treatment of cancer in the subject, wherein the at least one compound is for the administration to the subject in at least one therapeutically effective amount. The present disclosure provides at least one compound of the present disclosure for the manufacture of a medicament for the treatment of cancer in a subject, wherein the at least one compound is for the administration to the subject in at least one therapeutically effective amount.

The present disclosure provides a method of preventing, treating and/or ameliorating cancer in a subject, the method comprising administering to the subject at least one therapeutically effective amount of at least one compound of the present disclosure. The present disclosure provides at least one compound for use in the prevention, treatment and/or amelioration of cancer in a subject, wherein the at least one compound is for the administration to the subject in at least one therapeutically effective amount. The present disclosure provides at least one compound of the present disclosure for use in the manufacture of a medicament for the prevention, treatment and/or amelioration of cancer in a subject, wherein the at least one compound is for administration to the subject in at least on therapeutically effective amount. Examples of cancer include but are not limited to, carcinoma, lymphoma, blastoma, sarcoma, leukemia and germ cell tumors. More particular examples of such cancers include adrenocortical carcinoma, bladder urothelial carcinoma, breast invasive carcinoma, cervical squamous cell carcinoma, endocervical adenocarcinoma, cholangiocarcinoma, colon adenocarcinoma, lymphoid neoplasm diffuse large B-cell lymphoma, esophageal carcinoma, glioblastoma multiforme, head and neck squamous cell carcinoma, kidney chromophobe, kidney renal clear cell carcinoma, kidney renal papillary cell carcinoma, acute myeloid leukemia, brain lower grade glioma, liver hepatocellular carcinoma, lung adenocarcinoma, lung squamous cell carcinoma, mesothelioma, ovarian serous cystadenocarcinoma, pancreatic adenocarcinoma, pheochromocytoma, paraganglioma, prostate adenocarcinoma, rectum adenocarcinoma, sarcoma, skin cutaneous melanoma, stomach adenocarcinoma, testicular germ cell tumors, thyroid carcinoma, thymoma, uterine carcinosarcoma, uveal melanoma. Other examples include breast cancer, lung cancer, lymphoma, melanoma, liver cancer, colorectal cancer, ovarian cancer, bladder cancer, renal cancer or gastric cancer. Further examples of cancer include neuroendocrine cancer, non-small cell lung cancer (NSCLC), small cell lung cancer, thyroid cancer, endometrial cancer, biliary cancer, esophageal cancer, anal cancer, salivary, cancer, vulvar cancer, cervical cancer, Acute lymphoblastic leukemia (ALL), Acute myeloid leukemia (AML), Adrenal gland tumors, Anal cancer, Bile duct cancer, Bladder cancer, Bone cancer, Bowel cancer, Brain tumors, Breast cancer, Cancer of unknown primary (CUP), Cancer spread to bone, Cancer spread to brain, Cancer spread to liver, Cancer spread to lung, Carcinoid, Cervical cancer, Children's cancers, Chronic lymphocytic leukemia (CLL), Chronic myeloid leukemia (CML), Colorectal cancer, Ear cancer, Endometrial cancer, Eye cancer, Follicular dendritic cell sarcoma, Gallbladder cancer, Gastric cancer, Gastro esophageal junction cancers, Germ cell tumors, Gestational trophoblastic disease (GTD), Hairy cell leukemia, Head and neck cancer, Hodgkin lymphoma, Kaposi's sarcoma, Kidney cancer, Laryngeal cancer, Leukemia, Linitis plastica of the stomach, Liver cancer, Lung cancer, Lymphoma, Malignant schwannoma, Mediastinal germ cell tumors, Melanoma skin cancer, Men's cancer, Merkel cell skin cancer, Mesothelioma, Molar pregnancy, Mouth and oropharyngeal cancer, Myeloma, Nasal and paranasal sinus cancer, Nasopharyngeal cancer, Neuroblastoma, Neuroendocrine tumors, Non-Hodgkin lymphoma (NHL), Esophageal cancer, Ovarian cancer, Pancreatic cancer, Penile cancer, Persistent trophoblastic disease and choriocarcinoma, Pheochromocytoma, Prostate cancer, Pseudomyxoma peritonei, Rectal cancer, Retinoblastoma, Salivary gland cancer, Secondary cancer, Signet cell cancer, Skin cancer, Small bowel cancer, Soft tissue sarcoma, Stomach cancer, T cell childhood non Hodgkin lymphoma (NHL), Testicular cancer, Thymus gland cancer, Thyroid cancer, Tongue cancer, Tonsil cancer, Tumors of the adrenal gland, Uterine cancer, Vaginal cancer, Vulval cancer, Wilms' tumor, Womb cancer and gynaecological cancer. Examples of cancer also include, but are not limited to, Hematologic malignancies, Lymphoma, Cutaneous T-cell lymphoma, Peripheral T-cell lymphoma, Hodgkin's lymphoma, Non-Hodgkin's lymphoma, Multiple myeloma, Chronic lymphocytic leukemia, chronic myeloid leukaemia, acute myeloid leukaemia, Myelodysplastic syndromes, Myelofibrosis, Biliary tract cancer, Hepatocellular cancer, Colorectal cancer, Breast cancer, Lung cancer, Non-small cell lung cancer, Ovarian cancer, Thyroid Carcinoma, Renal Cell Carcinoma, Pancreatic cancer, Bladder cancer, skin cancer, malignant melanoma, merkel cell carcinoma, Uveal Melanoma or Glioblastoma multiforme.

The present disclosure provides a method of treating leukemia in a subject comprising administering to the subject at least one therapeutically effective amount of at least one compound of the present disclosure. The present disclosure provides at least one compound of the present disclosure for use in the treatment of leukemia in the subject, wherein the at least one compound is for the administration to the subject in at least one therapeutically effective amount. The present disclosure provides at least one compound for the manufacture of a medicament for the treatment of leukemia in a subject, wherein the at least one compound is for the administration to the subject in at least one therapeutically effective amount.

The present disclosure provides a method of treating Acute myeloid leukemia (AML) in a subject comprising administering to the subject at least one therapeutically effective amount of at least one compound of the present disclosure. The present disclosure provides at least one compound of the present disclosure for use in the treatment of AML in the subject, wherein the at least one compound is for the administration to the subject in at least one therapeutically effective amount. The present disclosure provides at least one compound for the manufacture of a medicament for the treatment of AML in a subject, wherein the at least one compound is for the administration to the subject in at least one therapeutically effective amount.

The present disclosure provides a method of treating a disease in a subject comprising administering to the subject at least one therapeutically effective amount of at least one compound of the present disclosure. The present disclosure provides at least one compound of the present disclosure for use in the treatment of a disease in the subject, wherein the at least one compound is for the administration to the subject in at least one therapeutically effective amount. The present disclosure provides at least one compound of the present disclosure for the manufacture of a medicament for the treatment of a disease in a subject, wherein the at least one compound is for the administration to the subject in at least one therapeutically effective amount.

In some aspects, a disease can include, but is not limited to an inflammatory disease, an infectious disease, an immunological disease, a malignant disease, cancer, tumor growth, undesirable angiogenesis, obesity and rheumatoid arthritis.

The present disclosure provides a method of treating cancer in a subject comprising administering to the subject at least one therapeutically effective amount of compound 17. The present disclosure provides compound 17 for use in the treatment of cancer in the subject, wherein the at least one compound is for the administration to the subject in at least one therapeutically effective amount. The present disclosure provides compound 17 for the manufacture of a medicament for the treatment of cancer in a subject, wherein the at least one compound is for the administration to the subject in at least one therapeutically effective amount.

The present disclosure provides a method of preventing, treating and/or ameliorating cancer in a subject, the method comprising administering to the subject at least one therapeutically effective amount of compound 17. The present disclosure provides compound 17 for use in the prevention, treatment and/or amelioration of cancer in a subject, wherein the at least one compound is for the administration to the subject in at least one therapeutically effective amount. The present disclosure provides compound 17 for use in the manufacture of a medicament for the prevention, treatment and/or amelioration of cancer in a subject, wherein the at least one compound is for administration to the subject in at least on therapeutically effective amount.

The present disclosure provides a method of treating leukemia in a subject comprising administering to the subject at least one therapeutically effective amount of compound 17. The present disclosure provides compound 17 for use in the treatment of leukemia in the subject, wherein the at least one compound is for the administration to the subject in at least one therapeutically effective amount. The present disclosure provides compound 17 for the manufacture of a medicament for the treatment of leukemia in a subject, wherein the at least one compound is for the administration to the subject in at least one therapeutically effective amount.

The present disclosure provides a method of treating AML in a subject comprising administering to the subject at least one therapeutically effective amount of compound 17. The present disclosure provides compound 17 for use in the treatment of AML in the subject, wherein the at least one compound is for the administration to the subject in at least one therapeutically effective amount. The present disclosure provides compound 17 for the manufacture of a medicament for the treatment of AML in a subject, wherein the at least one compound is for the administration to the subject in at least one therapeutically effective amount.

The present disclosure provides a method of treating a disease in a subject comprising administering to the subject at least one therapeutically effective amount of compound 17. The present disclosure provides compound 17 for use in the treatment of a disease in the subject, wherein the at least one compound is for the administration to the subject in at least one therapeutically effective amount. The present disclosure provides compound 17 for the manufacture of a medicament for the treatment of a disease in a subject, wherein the at least one compound is for the administration to the subject in at least one therapeutically effective amount.

The present disclosure provides a method of treating cancer in a subject comprising administering to the subject at least one therapeutically effective amount of compound 8. The present disclosure provides compound 8 for use in the treatment of cancer in the subject, wherein the at least one compound is for the administration to the subject in at least one therapeutically effective amount. The present disclosure provides compound 8 for the manufacture of a medicament for the treatment of cancer in a subject, wherein the at least one compound is for the administration to the subject in at least one therapeutically effective amount.

The present disclosure provides a method of preventing, treating and/or ameliorating cancer in a subject, the method comprising administering to the subject at least one therapeutically effective amount of compound 8. The present disclosure provides compound 8 for use in the prevention, treatment and/or amelioration of cancer in a subject, wherein the at least one compound is for the administration to the subject in at least one therapeutically effective amount. The present disclosure provides compound 8 for use in the manufacture of a medicament for the prevention, treatment and/or amelioration of cancer in a subject, wherein the at least one compound is for administration to the subject in at least on therapeutically effective amount.

The present disclosure provides a method of treating leukemia in a subject comprising administering to the subject at least one therapeutically effective amount of compound 8. The present disclosure provides compound 8 for use in the treatment of leukemia in the subject, wherein the at least one compound is for the administration to the subject in at least one therapeutically effective amount. The present disclosure provides compound 8 for the manufacture of a medicament for the treatment of leukemia in a subject, wherein the at least one compound is for the administration to the subject in at least one therapeutically effective amount.

The present disclosure provides a method of treating AML in a subject comprising administering to the subject at least one therapeutically effective amount of compound 8. The present disclosure provides compound 8 for use in the treatment of AML in the subject, wherein the at least one compound is for the administration to the subject in at least one therapeutically effective amount. The present disclosure provides compound 8 for the manufacture of a medicament for the treatment of AML in a subject, wherein the at least one compound is for the administration to the subject in at least one therapeutically effective amount.

The present disclosure provides a method of treating a disease in a subject comprising administering to the subject at least one therapeutically effective amount of compound 8. The present disclosure provides compound 8 for use in the treatment of a disease in the subject, wherein the at least one compound is for the administration to the subject in at least one therapeutically effective amount. The present disclosure provides compound 8 for the manufacture of a medicament for the treatment of a disease in a subject, wherein the at least one compound is for the administration to the subject in at least one therapeutically effective amount.

The present disclosure provides a method of treating cancer in a subject comprising administering to the subject at least one therapeutically effective amount of at least one compound of the present disclosure in combination with at least one therapeutically effective amount of at least one additional therapeutic agent. The present disclosure provides a combination of at least one compound of the present disclosure and at least one additional therapeutic agent for use in the treatment of cancer in the subject, wherein the at least one compound is for the administration to the subject in at least one therapeutically effective amount and the at least one additional therapeutic agent is for the administration to the subject in at least one therapeutically effective amount. The present disclosure provides a combination of least one compound of the present disclosure and at least one additional therapeutic agent for the manufacture of a medicament for the treatment of cancer in a subject, wherein the at least one compound is for the administration to the subject in at least one therapeutically effective amount and the at least one additional therapeutic agent is for administration to the subject in at least on therapeutically effective amount.

The present disclosure provides at least one compound of the present disclosure for use in the treatment of cancer in the subject, wherein the at least one compound is for the administration to the subject in at least one therapeutically effective amount, and wherein the treatment further comprises the administration of at least one additional therapeutic agent to the subject. The present disclosure provides at least one compound of the present disclosure for the manufacture of a medicament for the treatment of cancer in a subject, wherein the at least one compound is for the administration to the subject in at least one therapeutically effective amount, and wherein the treatment further comprises the administration of at least one additional therapeutic agent to the subject.

The present disclosure provides a method of treating a disease in a subject comprising administering to the subject at least one therapeutically effective amount of at least one compound of the present disclosure in combination with at least one therapeutically effective amount of at least one additional therapeutic agent. The present disclosure provides a combination of at least one compound of the present disclosure and at least one additional therapeutic agent for use in the treatment of a disease in the subject, wherein the at least one compound is for the administration to the subject in at least one therapeutically effective amount and the at least one additional therapeutic agent is for the administration to the subject in at least one therapeutically effective amount. The present disclosure provides a combination of least one compound of the present disclosure and at least one additional therapeutic agent for the manufacture of a medicament for the treatment of a disease in a subject, wherein the at least one compound is for the administration to the subject in at least one therapeutically effective amount and the at least one additional therapeutic agent is for administration to the subject in at least on therapeutically effective amount.

The present disclosure provides at least one compound of the present disclosure for use in the treatment of a disease in the subject, wherein the at least one compound is for the administration to the subject in at least one therapeutically effective amount, and wherein the treatment further comprises the administration of at least one additional therapeutic agent to the subject. The present disclosure provides at least one compound of the present disclosure for the manufacture of a medicament for the treatment of a disease in a subject, wherein the at least one compound is for the administration to the subject in at least one therapeutically effective amount, and wherein the treatment further comprises the administration of at least one additional therapeutic agent to the subject.

Additional therapeutic agents can include, but are not limited to, chemotherapeutic agents, anti-cancer agents, DNA alkylating agents, DNA damage response (DDR) inhibitors, cell-cycle checkpoint inhibitors, PARP inhibitors, HDAC inhibitors, kinase inhibitors, Bcl-2 inhibitors, Mcl-1 inhibitors, PD-L1 targeted agents, immunotherapy agents and bioenergetics modulators. Additional therapeutic agents can include, but are not limited to cisplatin, cytarabine, doxorubicin, paclitaxel, temozolomide, dasatinib, nilotinib, fluvestrant, venetoclax, metformin, or combinations thereof.

In some aspects, anti-cancer agents can include, but are not limited to, 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abemaciclib, Abiraterone acetate, Abraxane, Accutane, Actinomycin-D, Adcetris, Ado-Trastuzumab Emtansine, Adriamycin, Adrucil, Afatinib, Afinitor, Agrylin, Ala-Cort, Aldesleukin, Alemtuzumab, Alecensa, Alectinib, Alimta, Alitretinoin, Alkaban-AQ, Alkeran, All-transretinoic Acid, Alpha Interferon, Altretamine, Alunbrig, Amethopterin, Amifostine, Aminoglutethimide, Anagrelide, Anandron, Anastrozole, Apalutamide, Arabinosylcytosine, Ara-C, Aranesp, Aredia, Arimidex, Aromasin, Arranon, Arsenic Trioxide, Arzerra, Asparaginase, Atezolizumab, Atra, Avastin, Avelumab, Axicabtagene Ciloleucel, Axitinib, Azacitidine, Bavencio, Bcg, Beleodaq, Belinostat, Bendamustine, Bendeka, Besponsa, Bevacizumab, Bexarotene, Bexxar, Bicalutamide, Bicnu, Blenoxane, Bleomycin, Blinatumomab, Blincyto, Bortezomib, Bosulif, Bosutinib, Brentuximab Vedotin, Brigatinib, Busulfan, Busulfex, C225, Cabazitaxel, Cabozantinib, Calcium Leucovorin, Campath, Camptosar, Camptothecin-11, Capecitabine, Caprelsa, Carac, Carboplatin, Carfilzomib, Carmustine, Carmustine Wafer, Casodex, CCI-779, Ccnu, Cddp, Ceenu, Ceritinib, Cerubidine, Cetuximab, Chlorambucil, Cisplatin, Citrovorum Factor, Cladribine, Clofarabine, Clolar, Cobimetinib, Cometriq, Cortisone, Cosmegen, Cotellic, Cpt-11, Crizotinib, Cyclophosphamide, Cyramza, Cytadren, Cytarabine, Cytarabine Liposomal, Cytosar-U, Cytoxan, Dabrafenib, Dacarbazine, Dacogen, Dactinomycin, Daratumumab, Darbepoetin Alfa, Darzalex, Dasatinib, Daunomycin, Daunorubicin, Daunorubicin Cytarabine (Liposomal), daunorubicin-hydrochloride, Daunorubicin Liposomal, DaunoXome, Decadron, Decitabine, Degarelix, Delta-Cortef, Deltasone, Denileukin Diftitox, Denosumab, DepoCyt, Dexamethasone, Dexamethasone Acetate, Dexamethasone Sodium Phosphate, Dexasone, Dexrazoxane, Dhad, Dic, Diodex, Docetaxel, Doxil, Doxorubicin, Doxorubicin Liposomal, Droxia, DTIC, Dtic-Dome, Duralone, Durvalumab, Eculizumab, Efudex, Ellence, Elotuzumab, Eloxatin, Elspar, Eltrombopag, Emcyt, Empliciti, Enasidenib, Enzalutamide, Epirubicin, Epoetin Alfa, Erbitux, Eribulin, Erivedge, Erleada, Erlotinib, *Erwinia* L-asparaginase, Estramustine, Ethyol, Etopophos, Etoposide, Etoposide Phosphate, Eulexin, Everolimus, Evista, Exemestane, Fareston, Farydak, Faslodex, Femara, Filgrastim, Firmagon, Floxuridine, Fludara, Fludarabine, Fluoroplex, Fluorouracil, Fluorouracil (cream), Fluoxymesterone, Flutamide, Folinic Acid, Folotyn, Fudr, Fulvestrant, G-Csf, Gazyva, Gefitinib, Gemcitabine, Gemtuzumab ozogamicin, Gemzar, Gilotrif, Gleevec, Gleostine, Gliadel Wafer, Gm-Csf, Goserelin, Granix, Granulocyte-Colony Stimulating Factor, Granulocyte Macrophage Colony Stimulating Factor, Halaven, Halotestin, Herceptin, Hexadrol, Hexalen, Hexamethylmelamine, Hmm, Hycamtin, Hydrea, Hydrocort Acetate, Hydrocortisone, Hydrocortisone Sodium Phosphate, Hydrocortisone Sodium Succinate, Hydrocortone Phosphate, Hydroxyurea, Ibrance, Ibritumomab, Ibritumomab Tiuxetan, Ibrutinib, Iclusig, Idamycin, Idarubicin, Idelalisib, Idhifa, Ifex, IFN-alpha, Ifosfamide, IL-11, IL-2, Imbruvica, Imatinib Mesylate, Imfinzi, Imidazole Carboxamide, Imlygic, Inlyta, Inotuzumab Ozogamicin, Interferon-Alfa, Interferon Alfa-2b (PEG Conjugate), Interleukin-2, Interleukin-11, Intron A (interferon alfa-2b), Ipilimumab, Iressa, Irinotecan, Irinotecan (Liposomal), Isotretinoin, Istodax, Ixabepilone, Ixazomib, Ixempra, Jakafi, Jevtana, Kadcyla, Keytruda, Kidrolase, Kisqali, Kymriah, Kyprolis, Lanacort, Lanreotide, Lapatinib, Lartruvo, L-Asparaginase, Lbrance, Lcr, Lenalidomide, Lenvatinib, Lenvima, Letrozole, Leucovorin, Leukeran, Leukine, Leuprolide, Leurocristine, Leustatin, Liposomal Ara-C, Liquid Pred, Lomustine, Lonsurf, L-PAM, L-Sarcolysin, Lupron, Lupron Depot, Lynparza, Marqibo, Matulane, Maxidex, Mechlorethamine, Mechlorethamine Hydrochloride, Medralone, Medrol, Megace, Megestrol, Megestrol Acetate, Mekinist, Mercaptopurine, Mesna, Mesnex, Methotrexate, Methotrexate Sodium, Methylprednisolone, Meticorten, Midostaurin, Mitomycin, Mitomycin-C, Mitoxantrone, M-Prednisol, MTC, MTX, Mustargen, Mustine, Mutamycin, Myleran, Mylocel, Mylotarg, Navelbine, Necitumumab, Nelarabine, Neosar, Neratinib, Nerlynx, Neulasta, Neumega, Neupogen, Nexavar, Nilandron, Nilotinib, Nilutamide, Ninlaro, Nipent, Niraparib, Nitrogen Mustard, Nivolumab, Nolvadex, Novantrone, Nplate, Obinutuzumab, Octreotide, Octreotide Acetate, Odomzo, Ofatumumab, Olaparib, Olaratumab, Omacetaxine, Oncospar, Oncovin, Onivyde, Ontak, Onxal, Opdivo, Oprelvekin, Oxapred, Orasone, Osimertinib, Otrexup, Oxaliplatin, Paclitaxel, Paclitaxel Protein-bound, Palbociclib, Pamidronate, Panitumumab, Panobinostat, Panretin, Paraplatin, Pazopanib, Pediapred, Peg Interferon, Pegaspargase, Pegfilgrastim, Peg-Intron, PEG-L-asparaginase, Pembrolizumab, Pemetrexed, Pentostatin, Perjeta, Pertuzumab, Phenylalanine Mustard, Platinol, Platinol-AQ, Pomalidomide, Pomalyst, Ponatinib, Portrazza, Pralatrexate, Prednisolone, Prednisone, Prelone, Procarbazine, Procrit, Proleukin, Prolia, Prolifeprospan 20 with Carmustine Implant, Promacta, Provenge, Purinethol, Radium 223 Dichloride, Raloxifene, Ramucirumab, Rasuvo, Regorafenib, Revlimid, Rheumatrex, Ribociclib, Rituxan, Rituxan Hycela, Rituximab, Rituximab Hyalurodinase, Roferon-A (Interferon Alfa-2a), Romidepsin, Romiplostim, Rubex, Rubidomycin Hydrochloride, Rubraca, Rucaparib, Ruxolitinib, Rydapt, Sandostatin, Sandostatin LAR, Sargramostim, Siltuximab, Sipuleucel-T, Soliris, Solu-Cortef, Solu-Medrol, Somatuline, Sonidegib, Sorafenib, Sprycel, Sti-571, Stivarga, Streptozocin, SU11248, Sunitinib, Sutent, Sylvant, Synribo, Tafinlar, Tagrisso, Talimogene Laherparepvec, Tamoxifen, Tarceva, Targretin, Tasigna, Taxol, Taxotere, Tecentriq, Temodar, Temozolomide, Temsirolimus, Teniposide, Tespa, Thalidomide, Thalomid, TheraCys, Thioguanine, Thioguanine Tabloid, Thiophosphoamide, Thioplex, Thiotepa, Tice, Tisagenlecleucel, Toposar, Topotecan, Toremifene, Torisel, Tositumomab, Trabectedin, Trametinib, Trastuzumab, Treanda, Trelstar, Tretinoin, Trexall, Trifluridine/Tipiricil, Triptorelin pamoate, Trisenox, Tspa, T-VEC, Tykerb, Valrubicin, Valstar, Vandetanib, VCR, Vectibix, Velban, Velcade, Vemurafenib, Venclexta, Venetoclax, VePesid, Verzenio, Vesanoid, Viadur, Vidaza, Vinblastine, Vinblastine Sulfate, Vincasar Pfs, Vincristine, Vincristine Liposomal, Vinorelbine, Vinorelbine Tartrate, Vismodegib, Vlb, VM-26, Vorinostat, Votrient, VP-16, Vumon, Vyxeos, Xalkori Capsules, Xeloda, Xgeva, Xofigo, Xtandi, Yervoy, Yescarta, Yondelis, Zaltrap, Zanosar, Zarxio, Zejula, Zelboraf, Zevalin, Zinecard, Ziv-aflibercept, Zoladex, Zoledronic Acid, Zolinza, Zometa, Zydelig, Zykadia, Zytiga, or any combination thereof.

Immunotherapy can comprise administering checkpoint inhibitors. Checkpoint inhibitors can comprise antibodies. Checkpoint inhibitors include, but are not limited to, anti-CTLA4 antibodies, anti-PD-1 antibodies, anti-PD-L1 antibodies, anti-AZAR antibodies, anti-B7-H3 antibodies, anti-B7-H4 antibodies, anti-BTLA antibodies, anti-IDO antibodies, anti-KIR antibodies, anti-LAG3 antibodies, anti-TIM3 antibodies and anti-VISTA (V-domain Ig suppressor of T cell activation) antibodies.

Anti-CTLA4 antibodies can include, but are not limited to, ipilimumab, tremelimumab and AGEN-1884. Anti-PD-1 antibodies include, but are not limited to, pembrolizumab, nivolumab pidilizumab, cemiplimab, REGN2810, AMP-224, MED10680, PDR001 and CT-001. Anti-PD-L1 antibodies include, but are not limited to atezolizumab, avelumab and durvalumab. Anti-CD137 antibodies include, but are not limited to, urelumab. Anti-B7-H3 antibodies include, but are not limited to, MGA271. Anti-KIR antibodies include, but are not limited to, Lirilumab. Anti-LAG3 antibodies include, but are not limited to, BMS-986016.

The term "immunotherapy" can refer to activating immunotherapy or suppressing immunotherapy. As will be appreciated by those in the art, activating immunotherapy refers to the use of a therapeutic agent that induces, enhances, or promotes an immune response, including, e.g., a T cell response while suppressing immunotherapy refers to the use of a therapeutic agent that interferes with, suppresses, or inhibits an immune response, including, e.g., a T cell response. Activating immunotherapy may comprise the use of checkpoint inhibitors. Activating immunotherapy may comprise administering to a subject a therapeutic agent that activates a stimulatory checkpoint molecule. Stimulatory checkpoint molecules include, but are not limited to, CD27, CD28, CD40, CD122, CD137, OX40, GITR and ICOS. Therapeutic agents that activate a stimulatory checkpoint molecule include, but are not limited to, MED10562, TGN1412, CDX-1127, lipocalin.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. An antibody that binds to a target refers to an antibody that is capable of binding the target with sufficient affinity such that the antibody is useful as a diagnostic and/or therapeutic agent in targeting the target. In one embodiment, the extent of binding of an anti-target antibody to an unrelated, non-target protein is less than about 10% of the binding of the antibody to target as measured, e.g., by a radioimmunoassay (RIA) or biacore assay. In certain embodiments, an antibody that binds to a target has a dissociation constant (Kd) of <1 μM, <100 nM, <10 nM, <1 nM, <0.1 nM, <0.01 nM, or <0.001 nM (e.g. $10^8$ M or less, e.g. from $10^8$ M to $10^{13}$ M, e.g., from $10^9$ M to $10^{13}$ M). In certain embodiments, an anti-target antibody binds to an epitope of a target that is conserved among different species.

A "blocking antibody" or an "antagonist antibody" is one that partially or fully blocks, inhibits, interferes, or neutralizes a normal biological activity of the antigen it binds. For example, an antagonist antibody may block signaling through an immune cell receptor (e.g., a T cell receptor) so as to restore a functional response by T cells (e.g., proliferation, cytokine production, target cell killing) from a dysfunctional state to antigen stimulation.

An "agonist antibody" or "activating antibody" is one that mimics, promotes, stimulates, or enhances a normal biological activity of the antigen it binds. Agonist antibodies can also enhance or initiate signaling by the antigen to which it binds. In some embodiments, agonist antibodies cause or activate signaling without the presence of the natural ligand. For example, an agonist antibody may increase memory T cell proliferation, increase cytokine production by memory T cells, inhibit regulatory T cell function, and/or inhibit regulatory T cell suppression of effector T cell function, such as effector T cell proliferation and/or cytokine production.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

As used herein, the term additional therapeutic agents can also comprise the administration of radiation therapy, surgery or any combination thereof.

Pharmaceutical Compositions

The disclosed compounds may be combined with pharmaceutically acceptable excipients, and optionally sustained-release matrices, such as biodegradable polymers, to form therapeutic compositions. Therefore, also disclosed are pharmaceutical compositions including one or more of any of the compounds disclosed above and a pharmaceutically acceptable carrier. The composition may comprise a unit dosage form of the composition, and may further comprise instructions for administering the composition to a subject to inhibit cancer progression or metastasis, for example, instructions for administering the composition to achieve an anti-tumor effects or to inhibit a pathological cellular proliferation. Such pharmaceutical compositions may be used in methods for treating or preventing cancer growth in a subject by administering to the subject a therapeutically effective amount of the composition.

These pharmaceutical compositions can be in the form of tablets, capsules, powders, granules, lozenges, liquid or gel preparations, such as oral, topical, or sterile parenteral solutions or suspensions (e.g., eye or ear drops, throat or nasal sprays, etc.), transdermal patches, and other forms known in the art.

Pharmaceutical compositions can be administered systemically or locally in any manner appropriate to the treatment of a given condition, including orally, parenterally, intrathecally, rectally, nasally, buccally, vaginally, topically, optically, by inhalation spray, or via an implanted reservoir. The term "parenterally" as used herein includes, but is not limited to subcutaneous, intravenous, intramuscular, intrasternal, intrasynovial, intrathecal, intrahepatic, intralesional, and intracranial administration, for example, by injection or infusion. For treatment of the central nervous system, the pharmaceutical compositions may readily penetrate the blood-brain barrier when peripherally or intraventricularly administered.

Pharmaceutically acceptable carriers include, but are not limited to, ion exchangers, alumina, aluminum stearate, lecithin, serum proteins (such as human serum albumin), buffers (such as phosphates), glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Tablets and capsules for oral administration can be in a form suitable for unit dose presentation and can contain conventional pharmaceutically acceptable excipients. Examples of these include binding agents such as syrup, acacia, gelatin, sorbitol, tragacanth, and polyvinylpyrrolidone; fillers such as lactose, sugar, corn starch, calcium phosphate, sorbitol, or glycine; tableting lubricants, such as magnesium stearate, talc, polyethylene glycol, or silica; disintegrants, such as potato starch; and dispersing or wetting agents, such as sodium lauryl sulfate. Oral liquid preparations can be in the form of, for example, aqueous or oily suspensions, solutions, emulsions, syrups or elixirs, or can be presented as a dry product for reconstitution with water or other suitable vehicle before use.

The pharmaceutical compositions can also be administered parenterally in a sterile aqueous or oleaginous medium. The composition can be dissolved or suspended in a non-toxic, parenterally-acceptable diluent or solvent, e.g., as a solution in 1,3-butanediol. Commonly used vehicles and solvents include water, physiological saline, Hank's solution, Ringer's solution, and sterile, fixed oils, including synthetic mono- or di-glycerides, etc. For topical application, the drug may be made up into a solution, suspension, cream, lotion, or ointment in a suitable aqueous or non-aqueous vehicle. Additives may also be included, for example buffers such as sodium metabisulphite or disodium edeate; preservatives such as bactericidal and fungicidal agents, including phenyl mercuric acetate or nitrate, benzalkonium chloride or chlorhexidine, and thickening agents, such as hypromellose.

The dosage unit involved depends, for example, on the condition treated, nature of the formulation, nature of the condition, embodiment of the claimed pharmaceutical compositions, mode of administration, and condition and weight of the patient. Dosage levels are typically sufficient to achieve a tissue concentration at the site of action that is at least the same as a concentration that has been shown to be active in vitro, in vivo, or in tissue culture. For example, a dosage of about 0.1 µg/kg body weight/day to about 1000 mg/kg body weight/day, for example, a dosage of about 1 µg/kg body weight/day to about 1000 µg/kg body weight/day, such as a dosage of about 5 µg/kg body weight/day to about 500 µg/kg body weight/day can be useful for treatment of a particular condition.

The compounds can be used in the form of pharmaceutically acceptable salts derived from inorganic or organic acids and bases, including, but not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Base salts include, but are not limited to, ammonium salts, alkali metal salts (such as sodium and potassium salts), alkaline earth metal salts (such as calcium and magnesium salts), salts with organic bases (such as dicyclohexylamine salts), N-methyl-D-glucamine, and salts with amino acids (such as arginine, lysine, etc.). Basic nitrogen-containing groups can be quaternized, for example, with such agents as C1-8 alkyl halides (such as methyl, ethyl, propyl, and butyl chlorides, bromides, and iodides), dialkyl sulfates (such as dimethyl, diethyl, dibutyl, an diamyl sulfates), long-chain halides (such as decyl, lauryl, myristyl, and stearyl chlorides, bromides, and iodides), aralkyl halides (such as benzyl and phenethyl bromides), etc. Water or oil-soluble or dispersible products are produced thereby.

Pharmaceutically acceptable salts of the presently disclosed STAT3 inhibitor compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function, such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66: 1 (1977).

Each publication or patent cited herein is incorporated herein by reference in its entirety. The disclosure now being generally described will be more readily understood by reference to the following examples, which are included merely for the purposes of illustration of certain aspects of the embodiments of the present disclosure. The examples are not intended to limit the disclosure, as one of skill in the art would recognize from the above teachings and the following examples that other techniques and methods can satisfy the claims and can be employed without departing from the scope of the claimed disclosure.

EXAMPLES

These materials and methods were used in the preparation and execution of the following Examples:
Cells and Reagents HeLa were obtained from ATCC and were verified by the vendor. Cells were grown in EMEM supplemented with 10% heat inactivated FBS. Niclosamide was purchased from Cayman Chemical Company. Small molecules evaluated from the NCI diversity library screen were provided by the Developmental Therapeutics Program's chemical repository. All chemical reagents were purchased from the Aldrich Chemical Company, Fisher Chemicals or Alfa Aesar Chemicals and were of the highest available purity. Chemicals were used as supplied with no further treatment. If chemicals used were stated as dry/anhydrous, they were stored in septum-sealed bottles and removed under an inert nitrogen environment, with the reaction being carried out under the relevant inert atmosphere. Palladium catalysts were stored and measured out under an inert atmosphere.
Library Preparation and Compound Docking Computational-based molecular docking simulations were performed using Discovery Studio (BIOVIA, Inc.) and Maestro 9.4 (Schrödinger, Inc.). The crystal structure of STAT3 was downloaded from the protein data bank (PDB ID: 4E68). Using Discovery Studio, water molecules and DNA was removed and the remaining protein structure was saved as a SDF file which was then imported into Maestro for protein preparation. The STAT3 protein was prepared by assigning bond orders, adding hydrogens, creating di-sulfide bridges, and repairing any broken or missing amino acid sequences. To complete protein preparation, restrained minimization of the protein structure was performed using the default constraint of 0.30 Å RMSD and the OPLS_2005 force field. While the protein was being prepared, the LigPrep wizard was used to prepare the compound libraries by generating possible states at target pH 7.0 using Epik, desaulting and generating tautomers, while retaining specified chiralities, and finishing with minimization by applying the OPLS_2005 force field. The prepared STAT3 protein was subjected to SiteMap generation that identified the top-ranked potential receptor binding sites, with the top five sites reported as output. From this output, the receptor sites identified within the DBD and LD were selected and docking grids were generated using Receptor Grid Generation.

Prepared ligand libraries were then docked into the grid generated on STAT3 using Ligand Docking in XP (extra precision) mode and included post-docking minimization.

The OTAVA fragment library was prepared and docked into the two identified binding sites within the DNA-binding domain of STAT3. Output from this docking was used to identify potential modifications to niclosamide and identify structures that may favor interaction with one binding site over the other. Niclosamide and the suggested analogs were prepared using ChemDraw and imported into Maestro 10.2 as a compound library where they were prepared as ligands and docked into each binding site. Compounds were ranked by XP Gscore from most negative to least negative.

Diversity Library Screen with Cresset Forge

Small molecule alignments and similarity analysis was conducted using Forge 10.4 software (Cresset). The NIH/NCI Diversity III library was aligned to the predicted binding orientation of niclosamide in either the DBD or LD and similarity calculated by both molecule shape and field characteristics (weighted equally in final scoring). Top compounds showing a high degree of similarity to one or both references were then tested in vitro to confirm STAT3 inhibitory activity.

Fluorescence Polarization (FP) Assay

FP assay was conducted as previously reported (Steffanie L. Furtek, S. L., et al., Evaluation of quantitative assays for the identification of direct signal transducer and activator of transcription 3 (STAT3) inhibitors (November 2016) Oncotarget 7(47): 77998-78008). Briefly, assay buffer (10 mM HEPES, pH 7.5, 50 mM NaCl, 1 mM EDTA, 2 mM DTT, and 0.01% Triton-X100), 100 nM of full length GST-tagged human STAT3 protein (Abcam), and varying concentrations of compounds were incubated for 1 hour at room temperature with mild agitation in 96-well half area black plates (Corning). Fluorescent peptide 5-FAM-G(pTyr)LPQTV-CONH$_2$ (Genscript) was added to each assay well at a concentration of 10 nM. Final well volumes were 30 µL. Following incubation with fluorescent peptide for 30 minutes at room temperature with mild agitation, plates were examined using FP Fluorescein Dual module with excitation filter FITC FP 480 and emission filter FITC FP P-pol535 and S-pol535. Data was expressed as percent control using the equation % $C=(mP_{drug}-mP_{free})/(mP_{STAT3}-mP_{free})*100$ where mP is the value for FP measurement.

Recombinant STAT3 ELISA

Measurement of STAT3 binding to DNA was performed using a TransAM STAT3 ELISA kit (Active Motif) and according to the previously used protocol. Briefly, full-length, GST-tagged human STAT3 protein and various concentrations of compounds to be evaluated or niclosamide were incubated in Complete Lysis Buffer at a final volume of 20 µL containing 0.1 µg recombinant protein for 1 hour with mild agitation. Following incubation with STAT3 inhibitors, samples were added to corresponding ELISA wells with 30 µL of Complete Binding Buffer and inhibition of STAT3 protein binding to the DNA consensus sequence was determined. Data was reported as percent of control.

MTT Assay

HeLa cells were plated in 96-well plates at a density of 5,000 cells/well in 100 µL of media and were incubated for 24 hours. Media was then aspirated and replaced with 100 µL of media containing various concentrations of compounds ranging from 500 µM-0.0019 µM. Cells were exposed to compounds for 24 hours, following which the media was aspirated and 50 µL MTT solution diluted in media was added to each well at a final concentration of 1 mg/mL. MTT was exposed to cells for 4 hours, aspirated, and then 100 µL of DMSO was added to each well. Plates were agitated for 10 minutes prior to reading absorbance at 540 nm in a microplate reader. Data was normalized and reported as percent of control.

Nuclear Extract Preparation

Nuclear extracts were prepared using a nuclear extraction kit (Signosis) according to product directions. Briefly, 100 mm dishes of cells were washed with 1×PBS and then 1 mL of 1× Buffer I was added and dishes were rocked on ice for 10 minutes. Cells were released from the dish using a sterile scraper and centrifuged at 1200 rpm for 5 minutes at 4° C. The supernatant was discarded and the pellets were resuspended in 1× Buffer II and shaken on ice for 2 hours. Samples were centrifuged at 1200 rpm for 5 minutes at 4° C. and the resulting supernatants containing the nuclear extracts were placed in new microcentrifuge tubes. Protein concentrations of samples were determined via Bradford assay.

Cell-Based STAT3 DNA-Binding ELISA

HeLa cells were plated at 1 million cells per 100 mm dish and incubated for approximately 72 hours, resulting in serum-starved confluent plates. Plates were then washed with PBS and fresh media was added containing concentrations of compounds to be evaluated or niclosamide for 24 hours. For single concentrations of compounds, cells were treated with 1 µM of compounds, as derived from 24 hour MTT assay $EC_{50}$ value for niclosamide. Dose-responses of niclosamide, compound 8, and compound 17 were similarly prepared at concentrations ranging from 2-0.0156 µM. Following incubation with compounds, cellular nuclear extracts were prepared.

Measurement of STAT3 binding to DNA was performed using the TransAM STAT3 ELISA kit. Sample wells contained 20 µg of nuclear extracts from treated HeLa cells diluted in 20 µL of Complete Lysis Buffer. The ELISA was then performed as described in the recombinant ELISA section. Data was normalized and reported as percent of control.

Caspase 3/7 Assay

The effect of STAT3 inhibitor on caspase activity was evaluated using a Caspase-Glo 3/7 kit (Promega) according to product directions. Briefly, HeLa cells were plated in white-walled, clear bottom 96-well plates at a density of 5,000 cells/well in 100 µL of media and were incubated for 24 hours. Media was then aspirated and replaced with 100 µL of media containing 1 µM or 10 µM of STAT3 inhibitor. Cells were exposed to compounds for 24 and 48 hours, following which plates were allowed to equilibrate to room temperature. Reconstituted caspase reagent was added to sample wells in a 1:1 ratio, mixed, and incubated in the dark for 1 hour. Luminescence was read using a microplate reader.

Statistical Analysis

Statistical analysis was performed using GraphPad Prism 5.0. Data for $IC_{50}$ and $EC_{50}$ curves was normalized. Error bars represent the standard error of the mean (SEM). Analysis by one-way analysis of variance (ANOVA) was conducted with Tukey's multiple comparison post hoc test. Statistical significance was set at $P<0.05$. Experiments were repeated in triplicate.

Example 1

Chemical Synthesis of STAT3 Inhibitors

Niclosamide analogs were prepared as outlined in FIG. 1A. Briefly, starting materials were reacted in anhydrous toluene in the presence of phosphoryl chloride under microwave irradiation for 1 hour at 180° C. (compounds 2-5, 9, 14, 17-18). Required acids for amide formation to produce final compounds 14 and 17 were synthesized via Suzuki coupling using 5-chloro-4-iodo-2-methoxybenzoic acid, corresponding boronic acid, and Pd(PPh$_3$)$_4$, followed by deprotection of the phenol using boron tribromide. Compound 6 was prepared by reacting niclosamide in acetic anhydride in the presence of phosphoric acid for 1 hour resulting in the final product as a precipitate. Reaction of compound 6 with dimethylsulfate yielded compound 7, and deacetylation of compound 7 produced compound 8. Compounds 10 and 11 were prepared using general synthesis method B, described below. Briefly, Tin(II) chloride was added to a mixture of the nitro aromatic in absolute ethanol and the reaction mixture was heated at reflux for 1.5 hours prior to isolation of the final compound.

Chromatography. Reaction monitoring and compounds identification was aided using Thin Layer Chromatography (TLC) and Retardation factor ($R_f$) values. TLC was conducted with Merck aluminum backed Si F$_{254}$ plates. UV absorbent compounds were visualized under short wave (254 nm) UV irradiation. Compound purification was achieved using medium pressure 'Flash' column chromatography, with the use of Davisil silica 40-60 µm as the stationary phase, or Biotage automated chromatography using pre-packed silica cartridges. A Biotage Isolera automated flash purification system was used with UV monitoring at 298 nm and compound collection at 254 nm.

Analytical Techniques. All melting points were determined using a Stuart Scientific SMP40 melting point apparatus and are uncorrected. $^1$H and $^{13}$C nuclear magnetic resonance (NMR) spectra were obtained as solutions in deuterated solvents DMSO-d$_6$ or CDCl$_3$ using a Bruker Avance III 400 spectrometer recording at 400 MHz. Chemical shifts (δ) are reported in parts per million (ppm) and the spin-multiplicity abbreviated as: s (singlet), d (doublet), t (triplet), q (quartet), quin (quintet), sept (septet), m (multiplet), or br (broad), with coupling constants (I) given in Hertz (Hz). Mass Spectrometry (MS) was carried out on an API 4000. Fourier Transform Infrared (FTIR) spectra were obtained using a Bruker Alpha Platinum-ATR as a neat sample.

Microwave Assisted Synthesis. When stated, reactions were carried out under microwave irradiation, in sealed vessels, using the Biotage Initiator Sixty with robotic sample bed. Samples were irradiated at 2.45 GHz, able to reach temperatures of 60-250° C. with a rate of heating at 2-5° C./sec, and pressures of up to 20 bar.

General Procedure A: Microwave Assisted Amide Formation.

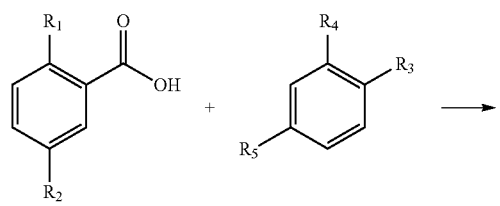

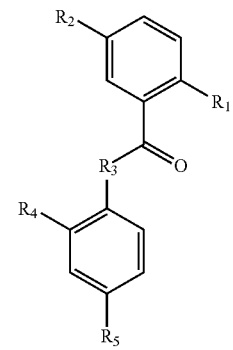

$R_1$ = OH, O—CH$_3$, or Cl
$R_2$ = Br, Cl, or NO$_2$
$R_3$ = NH or O
$R_4$ = Br or Cl
$R_5$ = H or NO$_2$

In an oven dried microwave vial, the required carboxylic acid (1.5 equiv), aniline (R$_3$ =NH$_2$) or phenol (R$_3$=OH) (1 equiv), and POCl$_3$ (1.5 equiv) were combined in anhydrous toluene (6 mL/mmol) and heated under microwave irradiation conditions at 180° C. for 1 hr. The solvent was removed in vacuo and the crude residue was subsequently purified via silica gel chromatography to give the desired product.

General Procedure B. Tin(II) Chloride Mediated Reduction of Aromatic Nitro Groups.

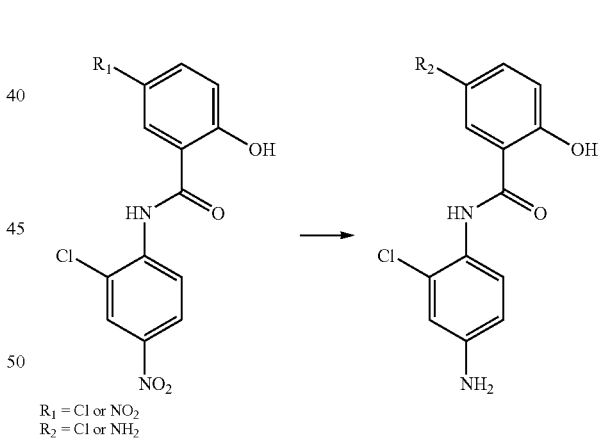

$R_1$ = Cl or NO$_2$
$R_2$ = Cl or NH$_2$

Tin(II) chloride (4.0 equiv) was added to a mixture of the nitro aromatic (1.0 equiv) in absolute ethanol (10 mL/mmol). The reaction mixture was heated at reflux for 1.5 hrs, after which the solvent was removed in vacuo. The resulting residue was dissolved in EtOAc (20 mL/mmol) and a saturated aqueous solution of NaHCO$_3$ was added until the aqueous phase was at pH 9-10. The resulting precipitate was removed by filtration through Celite® and the organic phase was collected, washed with brine (5 mL/mmol), dried (MgSO$_4$) and evaporated to dryness. The crude residue was subsequently purified by silica gel chromatography to give the desired compound.

General Procedure C: Suzuki Coupling of Boronic Acids.

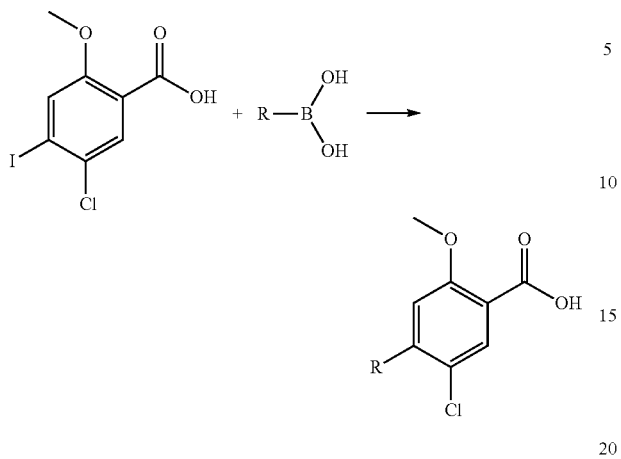

To a stirred solution of 5-chloro-4-iodo-2-methoxybenzoic acid (1 equiv) in anhydrous toluene (10 mL/mmol) was added the required boronic acid (1.2 equiv) and K$_2$CO$_3$ (5 equiv). This mixture was treated with Pd(PPh$_3$)$_4$ (0.05 equiv) and degassed with N$_2$. The reaction was heated to 110° C. and monitored by TLC for completion (approx. 2 hrs). The reaction was cooled, acidified (pH=3) with 2 M HCl, filtered through Celite®, which was subsequently washed with EtOAc (10 mL/mmol). The filtrate was extracted with EtOAc (15 mL/mmol) and the organic phase was washed with brine (5 mL/mmol), dried (MgSO$_4$), and concentrated in vacuo. The crude residue was purified via chromatography on silica to give the desired product.

5-Bromo-N-(2-bromo-4-nitrophenyl)-2-hydroxybenzamide (2)

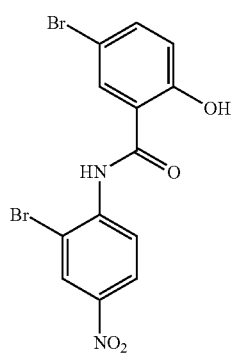

5-Bromo-2-hydroxybenzoic acid (53 mg, 0.24 mmol) and 2-bromo-4-nitroaniline (50 mg, 0.23 mmol) were reacted according to general procedure A, yielding the desired product as a yellow solid (47 mg, 0.11 mmol, 49%). R$_f$ 0.39 (3:2 Hexanes/EtOAc); M.p. 237-240° C.; IR (cm$^{-1}$) 3090, 1643, 1607, 1540, 1509; $^1$H NMR (400 MHz, DMSO-d$_6$) 7.06 (1H, d, J=8.7 Hz, H$^3$'), 7.66 (1H, dd, J=2.7 and 8.7 Hz, H$^4$'), 8.11 (1H, d, J=2.7 Hz, H$^6$'), 8.34 (1H, dd, J=2.6 and 9.2 Hz, H$^5$), 8.56 (1H, d, J=2.6 Hz, H$^3$), 8.77 (1H, d, J=9.2 Hz, H$^6$), 11.22 (1H, s, OH), 12.53 (1H, s, NH); $^{13}$C NMR (100 MHz, DMSO-d$_6$) 111.6 (C—Ar), 113.0 (C—Ar), 120.0 (C—Ar), 120.3 (C—Ar), 121.5 (C—Ar), 124.6 (C—Ar), 128.4 (C—Ar), 133.5 (C—Ar), 137.2 (C—Ar), 142.9 (C—Ar), 143.2 (C—Ar), 156.1 (C—Ar), 163.0 (C=O); MS (ES-) m/z 413.2 [M$^{79}$Br$^{79}$Br—H]$^-$, 415.0 [M$^{79}$Br$^{81}$Br—H]$^-$, 417.0 [M$^{81}$Br$^{81}$Br—H]$^-$ 5-Chloro-N-(2-chlorophenyl)-2-hydroxybenzamide (3)

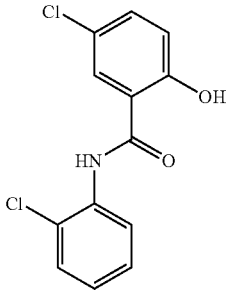 [SMILES: O=C(Nc1ccccc1Cl)c1cc(Cl)ccc1O]

2-Chloroaniline (82 µL, 0.78 mmol) and 5-chlorosalicylic acid (203 mg, 1.17 mmol) were reacted according to general procedure A, resulting in the desired product a white solid (45 mg, 0.17 mmol, 21%). R$_f$ 0.31 (4:1 Hexanes/EtOAc); M.p. 187-190° C.; IR (cm$^{-1}$) 3214, 2359, 1652, 1596, 1544; $^1$H NMR (400 MHz, DMSO-d$_6$) 7.08 (1H, d, J=8.8 Hz, H$^3$'), 7.21 (1H, ddd, J=2.9, 8.8 and 8.8 Hz, H$^5$), 7.41 (1H, ddd, J=1.4, 8.4 and 8.4 Hz, H$^4$), 7.52 (1H, dd, J=2.9 and 8.8 Hz, H$^4$'), 7.57 (1H, dd, J=1.4 and 8.4 Hz, H$^6$), 8.0 (1H, d, J=2.9, H$^6$'), 8.40 (1H, dd, J=1.4 and 8.4, H$^3$), 10.89 (1H, s, OH), 12.26 (1H, s, NH); $^{13}$C NMR (100 MHz, DMSO-d$_6$) 119.6 (C—Ar), 120.1 (C—Ar), 123.4 (C—Ar), 124.0 (C—Ar), 124.1 (C—Ar), 126.0 (C—Ar), 128.4 (C—Ar), 129.8 (C—Ar), 130.2 (C—Ar), 133.9 (C—Ar), 135.5 (C—Ar), 155.9 (C—Ar), 163.2 (C=O); MS (ES-) m/z 280.2 [M$^{35}$Cl$^{35}$Cl-H]$^-$, 282.2 [M$^{35}$Cl$^{37}$Cl-H]$^-$, 284.2 [M$^{37}$Cl$^{37}$Cl-H]$^-$.

2-Chloro-4-nitrophenyl 5-chloro-2-hydroxybenzoate (4)

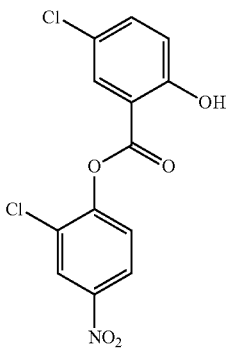 [SMILES: O=C(Oc1ccc([N+](=O)[O-])cc1Cl)c1cc(Cl)ccc1O]

2-Chloro-4-nitrophenol (50 mg, 0.29 mmol) and 5-chlorosalicylic acid (65 mg, 0.38 mmol) were reacted as per general procedure A, yielding the desired product as a white solid which was determined to be a mixture of atropisomers (26 mg, 0.077 mmol, 27%). R$_f$ 0.32 (9:1 Hexanes/EtOAc); M.p. 165-168° C.; IR (cm$^{-1}$) 3329, 3105, 1732, 1575, 1540; $^1$H NMR (400 MHz, DMSO-d$_6$) 6.89 (1.2H, d, J=9.2 Hz, H$^3$'$_{major}$) 7.12 (1H, d, J=9.2 Hz, H$^3$'$_{minor}$), 7.39 (1.2H, d, J=8.7 Hz, H$^6_{major}$) 7.64 (1H, dd, J=2.8 and 9.2 Hz, H$^4_{minor}$), 7.79-7.84 (2.2H, m, H$^6_{minor}$ and H$^5_{major}$) 7.97 (2.2H, d, J=2.8 Hz, H$^6_{major\ and\ minor}$), 8.12 (1.2H, dd, J=2.8 and 9.2 Hz, H$^{4'}_{major}$), 8.35 (1H, dd J=2.8 and 9.0 Hz, H$^5_{minor}$), 8.46 (1.2H, d, J=2.7 Hz, H$^3_{major}$), 8.54 (1H, d, J=2.7 Hz, H$^3_{minor}$), 10.66 (1H, OH$_{minor}$), 13.46 (1.2H, s, OH$_{major}$); $^{13}$C NMR (100 MHz, DMSO-d$_6$) 115.2 (C—Ar), 116.6 (C—Ar), 120.4 (C—Ar), 123.1 (C—Ar), 124.5 (C—Ar), 124.9 (C—Ar), 125.5 (C—Ar), 126.0 (C—Ar), 126.1 (C—Ar), 126.4 (C—Ar), 126.7 (C—Ar), 127.8 (C—Ar), 130.9 (C—Ar), 132.0 (C—Ar), 134.7 (C—Ar), 136.1 (C—Ar), 142.7 (C—Ar), 146.3 (C—Ar), 151.7 (C—Ar), 151.7 (C—Ar), 159.0 (C—Ar), 159.3 (C—Ar), 162.4 (C=O), 164.7 (C=O); MS (ES-) m/z 326.2 [M$^{35}$Cl$^{35}$Cl-H]$^-$, 328.2 [M$^{35}$Cl$^{37}$Cl-H]$^-$, 330.0 [M$^{37}$Cl$^{37}$Cl-H]$^-$.

5-Chloro-N-(2-chlorophenyl)-2-methoxybenzamide (5)

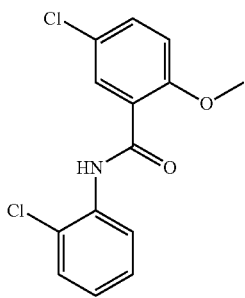 [SMILES: COc1ccc(Cl)cc1C(=O)Nc1ccccc1Cl]

2-Chloroaniline (41 µL, 0.39 mmol) and 5-chloro-2-methoxybenzoic acid (110 mg, 0.59 mmol) were reacted according to general procedure A, resulting in a white solid (91 mg, 0.31 mmol, 79%). R$_f$ 0.52 (4:1 Hexanes/EtOAc); M.p. 148-151° C.; IR (cm$^{-1}$) 3311, 3107, 1699, 1587, 1522, 1541; $^1$H NMR (400 MHz, DMSO-d$_6$) 4.08 (3H, s, OCH$_3$) 7.20 (1H, ddd, J=1.6, 7.7 and 8.0 Hz, H$^5$) 7.35 (1H, d, J=8.8 Hz, H$^{3'}$), 7.40 (1H, ddd, J=1.1, 8.4, and 8.6 Hz, H$^4$), 7.58 (1H, dd, J=1.3 and 8.0 Hz, H$^6$), 7.67 (1H, dd, J=2.9 and 8.8 Hz, H$^{4'}$), 7.98 (1H, d, J=2.9 Hz, H$^{6'}$), 8.41 (1H, dd, J=1.1 and 8.3 Hz, H$^3$), 10.51 (1H, s, NH); $^{13}$C NMR (100 MHz, DMSO-d$_6$) 57.6 (OCH$_3$), 115.4 (C—Ar), 122.9 (C—Ar), 123.0 (C—Ar), 123.7 (C—Ar), 125.6 (C—Ar), 125.8 (C—Ar), 128.4 (C—Ar), 129.8 (C—Ar), 130.9 (C—Ar), 133.7 (C—Ar), 135.4 (C—Ar), 156.5 (C—Ar), 161.9 (C=O); MS (ES+) m/z 296.2 [M$^{35}$Cl$^{35}$Cl+H]$^+$, 298.0 [M$^{35}$Cl$^{37}$Cl+H]$^+$, 300.0 [M$^{37}$Cl$^{37}$C+H]$^+$.

4-Chloro-2-((2-chloro-4-nitrophenyl)carbamoyl) phenyl acetate (6)

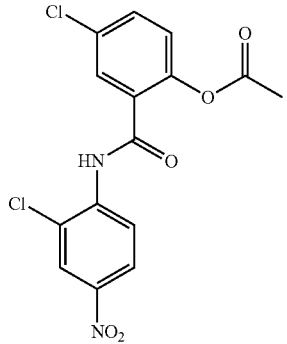 [SMILES: CC(=O)Oc1ccc(Cl)cc1C(=O)Nc1ccc([N+](=O)[O-])cc1Cl]

To a round bottom flask containing niclosamide (200 mg, 0.61 mmol), acetic anhydride (6 mL) and a phosphoric acid (2 drops) were added. The reaction was stirred at 70° C. for approximately 1 hr. Addition of ice and water (8 mL) under cooling resulted in formation of a precipitate. The precipitate was filtered and dried in a vacuum oven, giving the desired product as a white solid (190 mg, 0.51 mmol, 83%). R$_f$ 0.59 (3:2 Hexanes/EtOAc); M.p. 175-178° C. (lit. (11) 170° C.); IR (cm$^{-1}$) 3349, 3079, 1770, 1655, 1541, 1505; $^1$H NMR (400 MHz, DMSO-d$_6$) 2.25 (3H, s, AcCH$_3$), 7.36 (1H, d, J=8.0 Hz, H$^{3'}$), 7.71 (1H, d, J=8.6 Hz, H$^{4'}$), 7.85 (1H, s, H$^{6'}$), 8.09 (1H, d, J=10.0 Hz, H$^6$), 8.27 (1H, d, J=9.4 Hz, H$^5$), 8.42 (1H, s, H$^3$), 10.47 (1H, s, NH); $^{13}$C NMR (100 MHz, DMSO-d$_6$) 21.2 (C—Ac), 123.5 (C—Ar), 125.5 (C—Ar), 126.0 (C—Ar), 126.5 (C—Ar), 127.7 (C—Ar), 129.6 (C—Ar), 130.2 (C—Ar), 130.5 (C—Ar), 132.5 (C—Ar), 141.2 (C—Ar), 145.0 (C—Ar), 147.4 (C—Ar), 163.6 (C—Ar), 169.2 (C=O); MS (ES+) m/z 386.2 [M$^{35}$Cl$^{35}$Cl+H+H$_2$O]$^+$, 388.2 [M$^{35}$Cl$^{37}$Cl+H+H$_2$O]$^+$, 390.4 [M$^{37}$Cl$^{37}$Cl+H+H$_2$O]$^+$.

4-Chloro-2-((2-chloro-4-nitrophenyl)(methyl)carbamoyl)phenyl acetate (7)

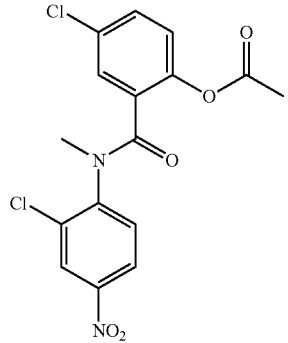 [SMILES: CC(=O)Oc1ccc(Cl)cc1C(=O)N(C)c1ccc([N+](=O)[O-])cc1Cl]

To an oven dried microwave vial K$_2$CO$_3$ (73 mg, 0.53 mmol), compound 6 (97 mg, 0.26 mmol), and dimethylsulfate (13 µL, 0.13 mmol) were dissolved in dry acetone (6 mL) and heated at 60° C. for 3.5 hrs. The resulting mixture was partitioned between EtOAc (15 mL) and water (10 mL) and the organic phase was washed with brine (10 mL) and dried (MgSO$_4$) before being evaporated to dryness. The crude residue was purified via flash chromatography (7:3 Hexanes/EtOAc) to produce a viscous oil (52 mg, 0.13 mmol, 51%). R$_f$ 0.29 (7:3 Hexanes/EtOAc); $^1$H NMR (400 MHz, DMSO-d$_6$) 2.23 (3H, s, AcCH$_3$), 2.29 (3H, s, NCH$_3$), 7.30 (1H, d, J=8.0 Hz, H$^{3'}$), 7.59 (1H, d, J=9.0 Hz, H$^{4'}$), 7.78 (1H, s, H$^{6'}$), 7.97 (1H, d, J=8.7 Hz, H$^6$), 8.33 (1H, d, J=8.6 Hz, H$^5$), 8.50 (1H, s, H$^3$); $^{13}$C NMR (100 MHz, DMSO-d$_6$) 21.2 (C—Ac), 25.8 (NCH$_3$), 124.0 (C—Ar), 125.7 (C—Ar), 125.9 (C—Ar), 128.2 (C—Ar), 130.2 (C—Ar), 132.0 (C—Ar), 133.1 (C—Ar), 134.06 (C—Ar), 141.8 (C—Ar), 146.2 (C—Ar), 148.6 (C—Ar), 166.5 (C—Ar), 167.0 (C—Ar), 171.6 (C=O); MS (ES+) m/z 428.2 [M$^{35}$Cl$^{35}$Cl+H+H$_2$O]$^+$, 430.2 [M$^{35}$Cl$^{37}$Cl+H+H$_2$O]$^+$, 432.2 [M$^{37}$Cl$^{37}$Cl+H+H$_2$O]$^+$.

5-Chloro-N-(2-chloro-4-nitrophenyl)-2-hydroxy-N-methylbenzamide (8)

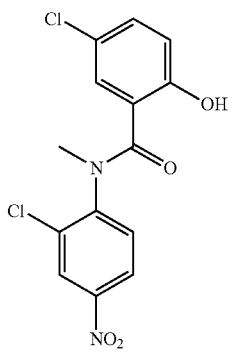 [SMILES: CN(C(=O)c1cc(Cl)ccc1O)c1ccc([N+](=O)[O-])cc1Cl]

Compound 7 (36 mg, 0.095 mmol) was dissolved in MeOH (0.5 mL) and dioxane (1 mL) in a microwave vial. 2 M NaOH (280 µL) was added and the reaction was stirred at room temperature for 2 hrs. Following completion, the reaction was brought to pH 2 using 2 M HCl and extracted in EtOAc (15 mL). The organic layer was dried over $MgSO_4$ and concentrated in vacuo to give a yellow solid (30 mg, 0.086 mmol, 91%). $R_f$ 0.21 (7:3 Hexanes/EtOAc); M.p. 218-222° C.; IR $(cm^{-1})$ 3249, 3099, 2921, 2852, 1771, 1675, 1604, 1575, 1541; $^1$H NMR (400 MHz, DMSO-$d_6$) 3.57 (3H, s, $NCH_3$), 7.10 (1H, d, J=8.8 Hz, $H^{3'}$), 7.55 (1H, dd, J=2.8 and 8.8 Hz, $H^{4'}$), 7.98 (1H, d, J=2.8 Hz, $H^{6'}$), 8.31 (1H, dd, J=2.8 and 9.2 Hz, $H^5$), 8.45 (1H, d, J=2.8 Hz, $H^6$), 8.83 (1H, d, J=9.2 Hz, $H^3$), 11.46 (1H, s, OH); $^{13}$C NMR (100 MHz, DMSO-$d_6$) 66.8 ($NCH_3$), 119.7 (C—Ar), 119.9 (C—Ar), 121.2 (C—Ar), 122.8 (C—Ar), 124.1 (C—Ar), 124.3 (C—Ar), 125.2 (C—Ar), 130.5 (C—Ar), 134.4 (C—Ar), 141.7 (C—Ar), 143.0 (C—Ar), 155.8 (C—Ar), 163.1 (C=O); MS (ES–) m/z 325.0 $[M^{35}Cl^{35}Cl-H+H_2O]^-$, 327.2 $[M^{35}Cl^{37}Cl-H+H_2O]^-$, 329.2 $[M^{37}Cl^{37}Cl-H+H_2O]^-$.

N-(2-Chloro-4-nitrophenyl)-2-hydroxy-5-nitrobenzamide (9)

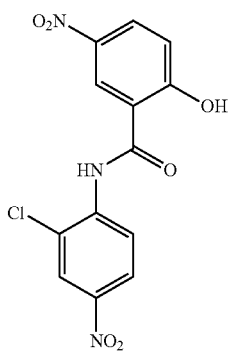 [SMILES: O=C(Nc1ccc([N+](=O)[O-])cc1Cl)c1cc([N+](=O)[O-])ccc1O]

2-Chloro-4-nitroaniline (200 mg, 1.2 mmol) and 5-nitrosalicylic acid (320 mg, 1.7 mmol) were reacted using general procedure A, yielding the desired compound as a yellow solid (240 mg, 0.72 mmol, 62%). $R_f$ 0.32 (17:3 DCM/MeOH); M.p. 270-273° C.; IR $(cm^{-1})$ 3184, 3077, 1696, 1586, 1559, 1515; $^1$H NMR (400 MHz, DMSO-$d_6$) 6.59 (1H, d, J=9.4 Hz, $H^6$), 8.00 (1H, dd, J=3.3 and 9.4 Hz, $H^5$), 8.26 (1H, dd, J=2.8 and 9.3 Hz, $H^{4'}$), 8.38 (1H, d, J=2.8 Hz, $H^{6'}$), 8.77 (1H, d, J=3.3 Hz, $H^3$), 8.93 (1H, d, J=9.3 Hz, $H^{3'}$), 11.62 (1H, s, NH); $^{13}$C NMR (100 MHz, DMSO-$d_6$) 118.8 (C—Ar), 119.1 (C—Ar), 121.4 (C—Ar), 123.1 (C—Ar), 124.3 (C—Ar), 125.2 (C—Ar), 127.9 (C—Ar), 129.7 (C—Ar), 139.9 (C—Ar), 141.5 (C—Ar), 143.1 (C—Ar); MS (ES–) m/z 336.2 $[M^{35}Cl-H]^-$, 338.2 $[M^{37}Cl-H]^-$.

*NOTE: unable to visualize all carbon environments by NMR.

5-Amino-N-(4-amino-2-chlorophenyl)-2-hydroxybenzamide (10)

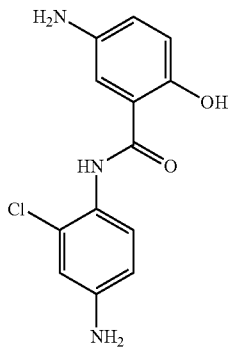

Compound 11 (50 mg, 0.15 mmol) was reacted with tin(II) chloride (110 mg, 0.60 mmol) using general procedure B, resulting in a yellow-orange solid (14 mg, 0.05 mmol, 34%). $R_f$ 0.39 (9:1 DCM/MeOH); M.p. 227-230° C.; IR $(cm^{-1})$ 3366, 2922, 2359, 1716, 1652, 1540; $^1$H NMR (400 MHz, DMSO-$d_6$) 4.75 (2H, s, Ar—$NH_2$), 5.28 (2H, s, Ar'—$NH_2$), 6.55 (1H, d, J=8.7 Hz, $H^{3'}$), 6.68-6.73 (3H, m, $H^5$, $H^6$, and $H^{4'}$), 7.24 (1H, m, $H^3$), 7.79 (1H, d, J=8.7 Hz, $H^{6'}$), 10.43 (1H, s, OH), 10.82 (1H, s, NH); $^{13}$C NMR (100 MHz, DMSO-$d_6$) 113.3 (C—Ar), 113.9 (C—Ar), 114.7 (C—Ar), 117.9 (C—Ar), 118.4 (C—Ar), 120.6 (C—Ar), 124.2 (C—Ar), 125.8 (C—Ar), 126.1 (C—Ar), 141.7 (C—Ar), 147.3 (C—Ar), 148.4 (C—Ar), 165.1 (C=O); MS (ES–) m/z 276.2 $[M^{35}Cl-H]^-$, 278.2 $[M^{37}Cl-H]^-$.

N-(4-Amino-2-chlorophenyl)-5-chloro-2-hydroxybenzamide (11)

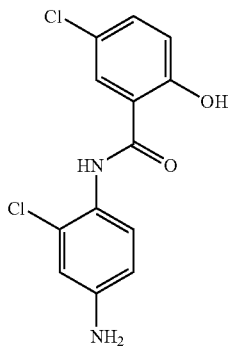 [SMILES: Nc1ccc(NC(=O)c2cc(Cl)ccc2O)c(Cl)c1]

Niclosamide (50 mg, 0.15 mmol) was reacted with tin(II) chloride (120 mg, 0.61 mmol) using general procedure B, resulting in a brown solid (56 mg, 0.15 mmol, 96%). $R_f$ 0.36

(3:2 Hexanes/EtOAc); M.p. 187-190° C. (lit. (12) 196-197° C.); IR (cm⁻¹) 3355, 3279, 2359, 1652, 1600, 1556; ¹H NMR (400 MHz, DMSO-d₆) 5.38 (2H, s, NH₂), 6.56 (1H, d, J=8.8 Hz, H⁵), 6.72 (1H, s, H³), 7.03 (1H, d, J=8.8 Hz, H⁶), 7.48 (1H, d, J=8.9 Hz, H⁴'), 7.66 (1H, d, J=8.8 Hz, H³') 8.02 (1H, s, H⁶') 10.39 (1H, s, OH) 12.24 (1H, s, NH); ¹³C NMR (100 MHz, DMSO-d₆) 113.3 (C—Ar), 113.9 (C—Ar), 119.2 (C—Ar), 119.6 (C—Ar), 123.1 (C—Ar), 123.5 (C—Ar), 126.7 (C—Ar), 127.2 (C—Ar), 129.3 (C—Ar), 133.6 (C—Ar), 148.1 (C—Ar), 157.0 (C—Ar), 164.3 (C=O); MS (ES+) m/z 297.0 [M³⁵Cl³⁵Cl+H]⁺, 299.0 [M³⁵Cl³⁷Cl+H]⁺, 301.2 [M³⁷Cl³⁷Cl+H]⁺.

2-Chloro-5-methoxy-[1,1'-biphenyl]-4-carboxylic acid (12)

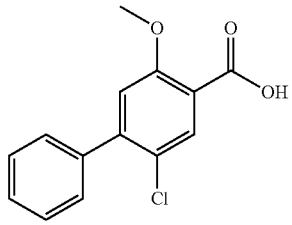 [SMILES: COc1cc(-c2ccccc2)c(Cl)cc1C(=O)O]

5-Chloro-4-iodo-2-methoxybenzoic acid (200 mg, 0.64 mmol) and benzene boronic acid (94 mg, 0.77 mmol) were reacted according to general procedure C, yielding the desired product as a pale yellow solid (130 mg, 0.49 mmol, 76%). R_f 0.24 (3:7 Hexanes/EtOAc); M.p. 143-146° C.; IR (cm⁻¹) 2925, 2847, 2357, 1698, 1674, 1653, 1541; ¹H NMR (400 MHz, DMSO-d₆) 3.87 (3H, s, OCH₃), 7.12 (1H, s, H⁶), 7.47-7.50 (5H, m, phenyl), 7.76 (1H, s, H³), 12.98 (1H, s, COOH); ¹³C NMR (100 MHz, DMSO-d₆) 56.7 (OCH₃), 116.1 (C—Ar), 122.2 (C—Ar), 122.4 (C—Ar), 128.7 (C—Ar), 129.6 (C—Ar), 131.9 (C—Ar), 138.6 (C—Ar), 144.3 (C—Ar), 157.4 (C—Ar), 166.3 (C=O); (ES+) m/z 296.2 [M³⁵Cl+H+CH₃OH]⁺, 298.2 [M³⁷Cl+H+CH₃OH]⁺.
*NOTE: unable to visualize all carbon environments by NMR.

2-Chloro-5-hydroxy-[1,1'-biphenyl]-4-carboxylic acid (13)

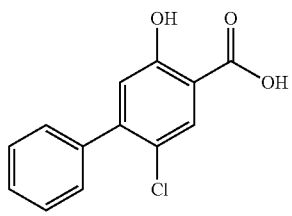 [SMILES: O=C(O)c1cc(Cl)c(-c2ccccc2)cc1O]

To a solution of compound 14 (88 mg, 0.34 mmol) in DCM (1 mL) at −78° C. was added BBr₃ (1.0 mL, 1.0 mmol of 1 M solution in DCM), and the reaction was allowed to warm to room temperature and stirred for 1.5 hrs. The reaction was brought to pH 2 using 2 M HCl and then partitioned between EtOAc (20 mL) and water (10 mL). The organic phase was dried over MgSO₄ and concentrated in vacuo resulting in a white solid (81 mg, 0.33 mmol, 97%). R_f 0.13 (9:1 DCM/MeOH); M.p. 167-170° C.; IR (cm⁻¹) 3292, 2852, 2548, 1667, 1616; ¹H NMR (400 MHz, DMSO-d₆) 7.00 (1H, s, H⁶), 7.46-7.49 (5H, m, phenyl), 7.87 (1H, s, H³), 11.30 (1H, s, COOH), 16.47 (1H, s, OH); ¹³C NMR (100 MHz, DMSO-d₆) 114.3 (C—Ar), 120.3 (C—Ar), 121.6 (C—Ar), 128.8 (C—Ar), 128.9 (C—Ar), 129.4 (C—Ar), 131.2 (C—Ar), 138.2 (C—Ar), 146.8 (C—Ar), 159.8 (C—Ar), 170.8 (C=O); MS (ES−) m/z 247.2 [M³⁵Cl−H]⁻, 249.0 [M³⁷Cl−H]⁻.
*NOTE: unable to visualize all carbon environments by NMR.

2-Chloro-N-(2-chloro-4-nitrophenyl)-5-hydroxy-[1,1'-biphenyl]-4-carboxamide (14)

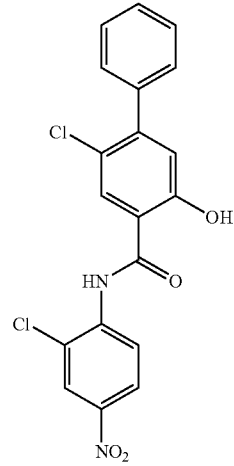 [SMILES: O=C(Nc1ccc([N+](=O)[O-])cc1Cl)c1cc(Cl)c(-c2ccccc2)cc1O]

Compound 15 (69 mg, 0.28 mmol) and 2-chloro-4-nitroaniline (37 mg, 0.21 mmol) were reacted according to general procedure A, resulting in the desired product, a yellow solid (16 mg, 0.04 mmol, 19%). R_f 0.28 (7:3 Hexanes/EtOAc); M.p. 230-232° C.; IR (cm⁻¹) 3281, 3079, 2924, 2852, 2358, 1631, 1541, 1508; ¹H NMR (400 MHz, DMSO-d₆) 7.05 (1H, s, H³'), 7.44-7.53 (5H, m, phenyl), 8.07 (1H, s, H⁶'), 8.29 (1H, dd, J=2.6 and 9.2 Hz, H⁵), 8.41 (1H, d, J=2.6 Hz, H⁶), 8.83 (1H, d, J=9.2 Hz, H³), 11.30 (1H, s, OH), 12.69 (1H, s, NH); ¹³C NMR (100 MHz, DMSO-d₆) 118.9 (C—Ar), 120.2 (C—Ar), 121.0 (C—Ar), 122.7 (C—Ar), 122.8 (C—Ar), 124.3 (C—Ar), 125.2 (C—Ar), 128.8 (C—Ar), 128.9 (C—Ar), 129.3 (C—Ar), 132.1 (C—Ar), 138.1 (C—Ar), 141.6 (C—Ar), 142.9 (C—Ar), 145.5 (C—Ar), 155.3 (C—Ar), 162.7 (C=O); MS (ES−) m/z 401.2 [M³⁵Cl³⁵Cl−H]⁻, 403.2 [M³⁵Cl³⁷Cl−H]⁻, 405.2 [M³⁷Cl³⁷Cl−H]⁻.
*NOTE: unable to visualize all carbon environments by NMR.

5-Chloro-4-(furan-2-yl)-2-methoxybenzoic acid (15)

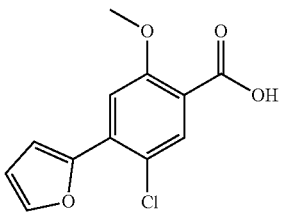 [SMILES: COc1cc(-c2ccco2)c(Cl)cc1C(=O)O]

5-Chloro-4-iodo-2-methoxybenzoic acid (250 mg, 0.80 mmol) and furan-2-boronic acid (270 mg, 2.4 mmol) were reacted per general procedure C, modified such that 3 equivalents of boronic acid were used, yielding the desired product, a tan solid (61 mg, 0.72 mmol, 30%). $R_f$ 0.29 (3:7 Hexanes/EtOAc); M.p. 148-152° C.; IR (cm$^{-1}$) 3079, 2924, 2848, 2344, 1699, 1600, 1541; $^1$H NMR (400 MHz, DMSO-$d_6$) 3.91 (3H, s, OCH$_3$), 6.73-6.74 (1H, m, furan-H$^4$), 7.32 (1H, m, furan-H$^5$), 7.48 (1H, s, H$^3$), 7.77 (1H, m, furan-H$^3$), 7.94 (1H, s, H$^6$), 12.96 (1H, s, COOH); $^{13}$C NMR (100 MHz, DMSO-$d_6$) 56.6 (OCH$_3$), 111.4 (C—Ar), 112.9 (C—Ar), 113.3 (C—Ar), 119.9 (C—Ar), 121.4 (C—Ar), 129.2 (C—Ar), 129.3 (C—Ar), 131.9 (C—Ar), 132.0 (C—Ar), 133.2 (C—Ar), 144.7 (C—Ar), 149.0 (C—Ar), 157.5 (C—Ar), 166.0 (C=O); MS (ES+) m/z 253.2 [M$^{35}$Cl+H]$^+$, 255.0 [M$^{37}$Cl+H]$^+$.

5-Chloro-4-(furan-2-yl)-2-hydroxybenzoic acid (16)

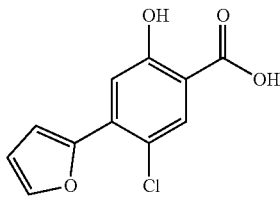 [SMILES: O=C(O)c1cc(Cl)c(-c2ccco2)cc1O]

To a solution of compound 17 (100 mg, 0.40 mmol) in DCM (1 mL) at −78° C. was added BBr$_3$ (1.2 mL, 1.2 mmol of 1 M solution in DCM), and the reaction was stirred at room temperature for 1.5 hrs. The reaction was brought to pH 2 using 2 M HCl and then partitioned between EtOAc (15 mL) and water (10 mL). The organic phase was dried over MgSO$_4$ and concentrated in vacuo resulting in a tan solid that was found to be a mixture of atropisomers by NMR (95 mg, 0.39 mmol, 99%). $R_f$ 0.11 (9:1 DCM/MeOH); M.p. 184-187° C.; IR (cm$^{-1}$) 2921, 2341, 1683, 1558; $^1$H NMR (400 MHz, DMSO-$d_6$) 6.69-6.70 (0.6H, m, furan-H$^4_{minor}$), 6.72-6.73 (1H, m, furan-H$^4_{major}$), 7.29-7.29 (1.2H, m, H$^3_{minor}$ and furan-H$^5_{minor}$), 7.34-7.35 (1H, m, furan-H$^5_{major}$), 7.38 (1H, s, H$^3_{major}$), 7.80 (0.6H, s, H$^6_{minor}$), 7.85 (1H, s, H$^6_{major}$), 7.90-7.90 (0.6H, m, furan-H$^3_{minor}$), 7.93-7.93 (1H, m, furan-H$^3_{major}$); $^{13}$C NMR (100 MHz, DMSO-$d_6$) 112.7 (C—Ar), 113.0 (C—Ar), 115.3 (C—Ar), 116.7 (C—Ar), 117.8 (C—Ar), 132.3 (C—Ar), 133.1 (C—Ar), 144.5 (C—Ar), 149.2 (C—Ar), 160.5 (C—Ar), 170.5 (C=O); MS (ES-) m/z 236.8 [M$^{35}$Cl-H]$^-$, 239.0 [M$^{37}$Cl-H]$^-$.

5-Chloro-N-(2-chloro-4-nitrophenyl)-4-(furan-2-yl)-2-hydroxybenzamide (17)

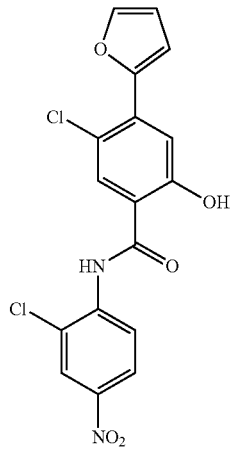 [SMILES: O=C(Nc1ccc([N+](=O)[O-])cc1Cl)c1cc(Cl)c(-c2ccco2)cc1O]

Compound 18 (72 mg, 0.30 mmol) and 2-chloro-4-nitroaniline (40 mg, 0.23 mmol) were reacted according to general procedure A to achieve the final compound, a yellow solid (38 mg, 0.097 mmol, 42%). $R_f$ 0.27 (7:3 Hexanes/EtOAc); M.p. 245-248° C.; IR (cm$^{-1}$) 3091, 2357, 1636, 1596, 1541; $^1$H NMR (400 MHz, DMSO-$d_6$) 6.72-6.73 (1H, m, furan-H$^4$), 7.34 (1H, m, furan-H$^5$), 7.55 (1H, s, H$^3$), 7.95 (1H, s, H$^6$), 8.06 (1H, m, furan-H$^3$), 8.28-8.30 (1H, m, H$^6$), 8.43-8.43 (1H, m, H$^5$), 8.82-8.84 (1H, m, H$^3$), 11.28 (1H, s, OH) 12.65 (1H, s, NH); $^{13}$C NMR (100 MHz, DMSO-$d_6$) 113.0 (C—Ar), 113.8 (C—Ar), 115.4 (C—Ar), 118.3 (C—Ar), 119.9 (C—Ar), 121.0 (C—Ar), 122.7 (C—Ar), 124.3 (C—Ar), 125.2 (C—Ar), 133.2 (C—Ar), 133.3 (C—Ar), 141.6 (C—Ar), 142.9 (C—Ar), 145.0 (C—Ar), 148.5 (C—Ar), 155.4 (C—Ar), 162.6 (C=O); MS (ES-) m/z 391.2 [M$^{35}$Cl$^{35}$Cl-H]$^-$, 393.2 [M$^{35}$Cl$^{37}$Cl-H]$^-$, 395.2 [M$^{37}$Cl$^{37}$Cl-H]$^-$.

2,5-Dichloro-N-(2-chloro-4-nitrophenyl)benzamide (18)

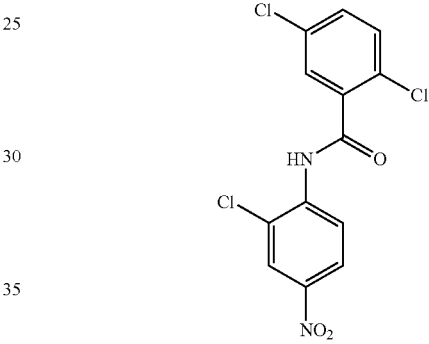

2-Chloro-4-nitroaniline (50 mg, 0.29 mmol) and 2,5-dichlorobenzoic acid (83 mg, 0.44 mmol) were reacted according to general procedure A, resulting in the desired compound as a pale yellow solid (63 mg, 0.18 mmol, 63%). $R_f$ 0.53 (4:1 Hexanes/EtOAc); M.p. 197-200° C.; IR (cm$^{-1}$) 3230, 3094, 2357, 1668, 1507; $^1$H NMR (400 MHz, DMSO-$d_6$) 7.63-7.63 (2H, m, H$^{3'}$ and H$^{4'}$), 7.80-7.80 (1H, m, H$^6$), 8.18-8.20 (1H, m, H$^{6'}$), 8.29-8.31 (1H, m, H$^5$), 8.41 (1H, m, H$^3$), 10.72 (1H, s, NH); $^{13}$C NMR (100 MHz, DMSO-$d_6$) 123.5 (C—Ar), 125.5 (C—Ar), 126.4 (C—Ar), 127.4 (C—Ar), 129.4 (C—Ar), 131.8 (C—Ar), 131.9 (C—Ar), 132.3 (C—Ar), 137.7 (C—Ar), 140.9 (C—Ar), 145.0 (C—Ar), 164.7 (C=O); MS (ES+) m/z 343.0 [M$^{35}$Cl$^{35}$Cl$^{35}$Cl+H]$^+$, 345.0 [M$^{35}$Cl$^{35}$Cl$^{37}$Cl+H]$^+$, 347.2 [M$^{35}$Cl$^{37}$Cl$^{37}$Cl+H]$^+$, 349.0 [M$^{37}$Cl$^{37}$Cl$^{37}$Cl+H]$^+$.

Example 2

Rational Design of Niclosamide Analogs Through in Silico Modelling

Using computational analysis of the crystal structure of STAT3, we identified two plausible binding sites within the DNA-binding domain (DBD) of STAT3. The SiteMap function in Maestro identified one of these as the previously reported DNA-binding site, and the other site identified was located within the linker domain of STAT3. Both sites have the potential for being targeted by niclosamide, and this ultimately leading to the abrogation of the activity of STAT3 as a transcription factor. However, as both sites contain amino acid residues that have been demonstrated to interact with the targeted DNA consensus sequence, it was necessary to design chemical probes to aid in elucidation of the likely site of action of DBD inhibitors.

Figure 1B:
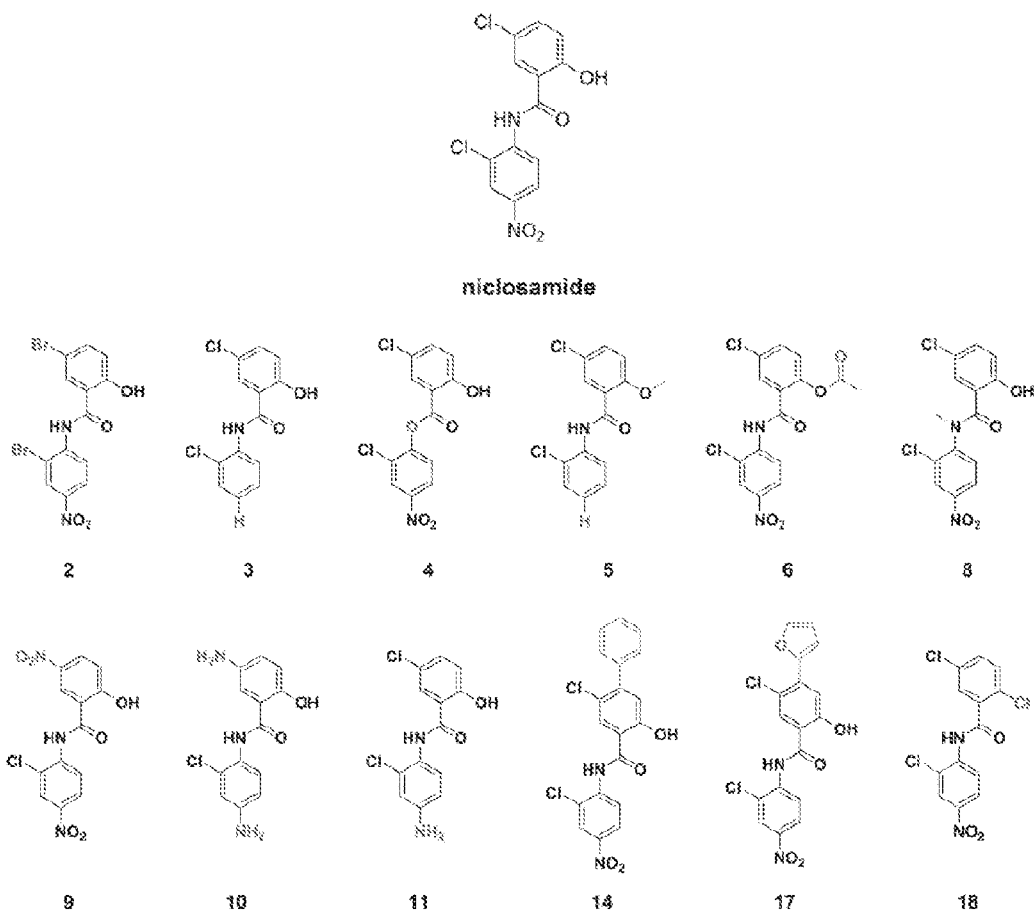
FIG. 1B shows the structure of niclosamide and synthesized analogs.

To maximize compound diversity, we examined a fragment library to identify structural analogs of niclosamide. Niclosamide and the OTAVA fragment library were docked into both sites and fragments were overlaid on niclosamide to identify potentially favorable modifications. Additional modifications were proposed that were expected to be unfavorable for binding based on disruption of interactions of niclosamide with surrounding amino acid residues. Both favorable and unfavorable compound structures were proposed for each site to suggest binding location of inhibitors. From the output of the fragment computational docking, we observed a preference for 5-, and 6-membered rings within the DBD region. The docked location of such fragments was adjacent to the phenolic aromatic ring of niclosamide, para- to the amide linker. This prompted the design of compounds 14 and 17 (FIG. 1B). Conversely, within the LD there appeared to be insufficient space to accommodate such modifications, and in support of this observation the docking scores for the relevant compounds ranked more poorly in this binding site, as shown in the following table:

| d Compound | DBD XP Gscore | LD XP Gscore |
| --- | --- | --- |
| 17 | −7.635 | −3.274 |
| 11 | −6.926 | −3.057 |
| 2 | −6.050 | −3.396 |
| niclosamide | −5.966 | −4.589 |
| 9 | −5.870 | −4.685 |
| 14 | −5.850 | −2.762 |
| 10 | −5.814 | −3.932 |
| 4 | −5.803 | −3.879 |
| 8 | −5.642 | −3.539 |
| 5 | −5.256 | −2.869 |
| 6 | −5.192 | −3.719 |
| 3 | −5.002 | −4.363 |
| 18 | −3.665 | −1.913 |

The initial structural modifications to niclosamide were minor, such as replacing the chlorine atoms with larger bromine atoms (compound 2) to increase Van de Waals radii, proposed to be tolerated in the LD but intended to introduce more steric constraints within the DBD. Compound 9 was designed to add a H-bond acceptor to the phenolic ring in place of the chloro atom to pick up potential interactions in the LD that were not seen in the DBD modeling. Within the DBD binding site, the nitro-group on niclosamide appeared to make a H-bond interaction, while in the LD site the nitro-group made no apparent interactions. To examine the necessity of this nitro-group, compounds 3 and 5 were proposed. Alternatively, compounds 10 and 11 replaced the nitro-group with an amine to replace this H-bond acceptor for a donor; a modification proposed to be beneficial in both binding sites. Compound 10 also replaced the chlorine group para to the phenol with an amine to attempt to establish another observed H-bond interaction within the LD. The necessity of H-bonding interactions from the phenol, seen in both binding sites, was assessed through the methylation or acetylation of the phenol, resulting in compounds 5 and 6, while compound 18 replaced the phenol with a chlorine atom to give a final compound with a similar Van de Waals radius as a methoxy group, whilst no longer acting as a H-bond acceptor. Methylation of the amide nitrogen (compound 8) and replacement of the amide with a phenol (compound 4) attempted to disrupt a proposed H-bond interaction in the DBD that was not observed in the LD.

A total of 12 analogs of niclosamide were designed and these compounds were docked into both identified binding sites and ranked by XP Gscore with the most negative scores being the most favorable. Compound 17 was the most favorable for the DBD and 9 was the most favorable for the LD with XP Gscores of −6.986 and −4.685, respectively (see table above). Docking the designed analogs in both sites revealed higher XP Gscores for the target site within the DBD compared to the site in the LD, possibly due to the tertiary structure of the DBD comprising largely of β-sheets allowing for greater flexibility for compound interactions. Once the computational modeling and in silico design was completed we synthesized the proposed analogs. Despite the apparent simplicity of the synthesis of such compounds, several amide coupling conditions were attempted without success before a reliable synthetic procedure was obtained. We determined that microwave irradiation was necessary to overcome the activation energy required for amide formation due to the largely electron poor and sterically hindered anilines in question (FIG. 1A). At completion, we successfully synthesized 12 analogs of niclosamide to test in vitro (FIG. 1B).

Example 3

Computational Screen Identified Small Molecules with High Structural Similarity to Niclosamide To identify commercially available compounds with potential inhibitory activity against STAT3 we utilized the computational modeling suite Cresset Forge. Using this program, small molecules bind to protein targets based primarily on 3D shape and electronic properties (charge, hydrophobicity, etc.), also referred to as the molecular force field. By comparing the fields among a series of compounds, we could identify structurally diverse compounds with potentially similar biological activities. Although not in this case, Forge is also capable of identifying similar compounds in the absence of a known protein target. The final output of the program gives a 4-point similarity plot and an overall percent similarity based on both structural and docking potentials.

Figure 2:
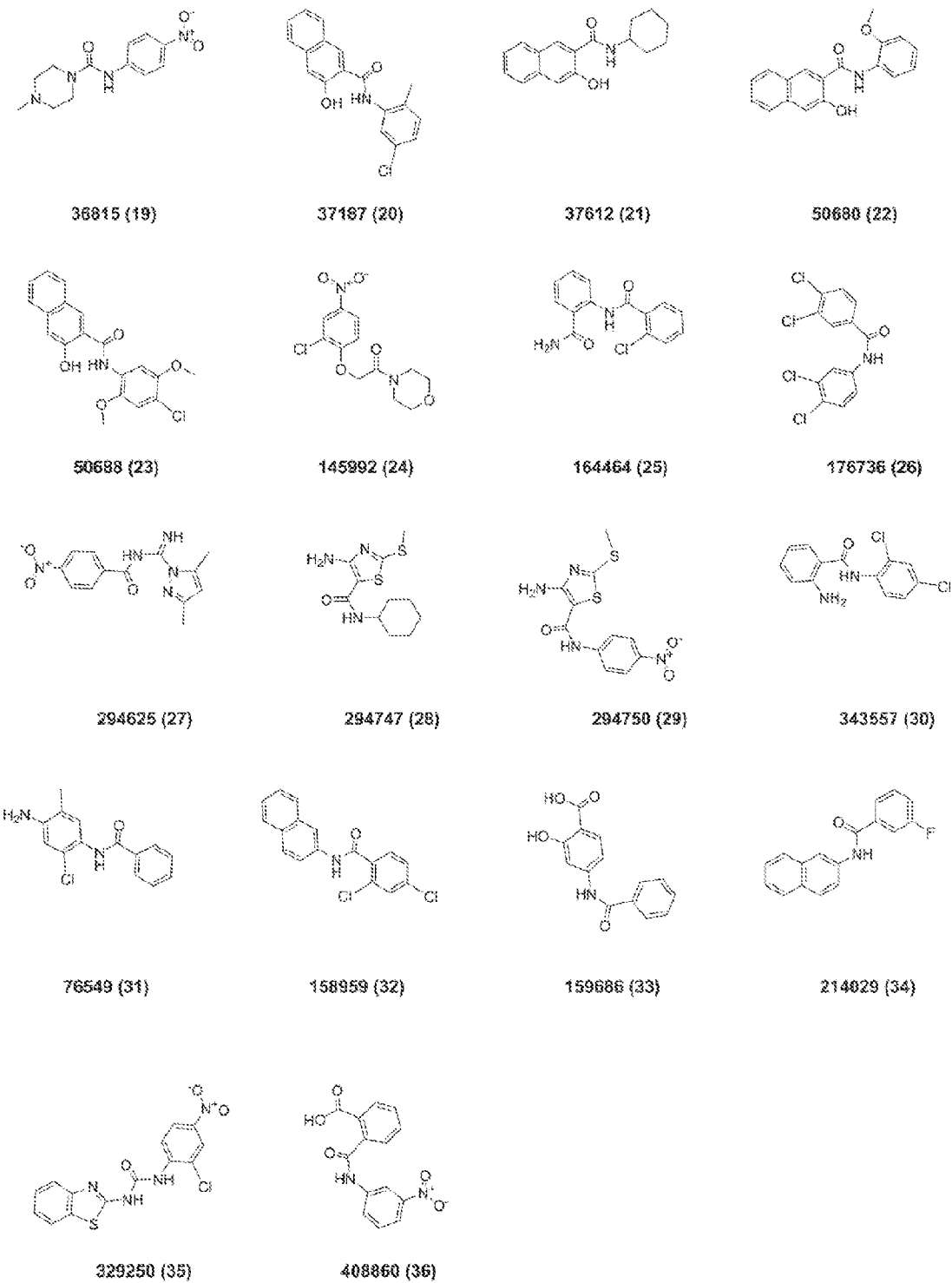
FIG. 2 shows the chemical structure of compounds identified from a computational screen against niclosamide using Cresset Forge. Compounds listed by NCI identifier and (corresponding index number).

Within Forge, we calculated, aligned, and compared the molecular force fields of each of the approx. 1600 compounds in the NCI Diversity III library using our niclosamide docking results in either the DBD or the LD as the reference. Interestingly, although there were some predicted differences in binding orientation of niclosamide between the two sites, the top scoring compound (30) was identical. Several compounds were identified as top hits in both sites. These include compounds 36815 (19), 164464 (25), and 176736 (26) (FIG. 2). A total of 18 compounds were identified as having greater than or equal to 85% similarity when compared to niclosamide in one or both binding sites. Unsurprisingly, due to the structural simplicity of niclosamide the majority of the compounds contained two aromatic rings linked by an amide, limiting the pharmacophore diversity that was achieved with this approach. All of the compounds were acquired from the chemical repository within the Developmental Therapeutics Program at NCI. Preparation of stock solutions in DMSO revealed insolubility issues with compound 294747 (28), and it was excluded from being tested in vitro. The remaining 17 compounds were evaluated for their affinity for recombinant STAT3.

Example 4

Figure 3A:
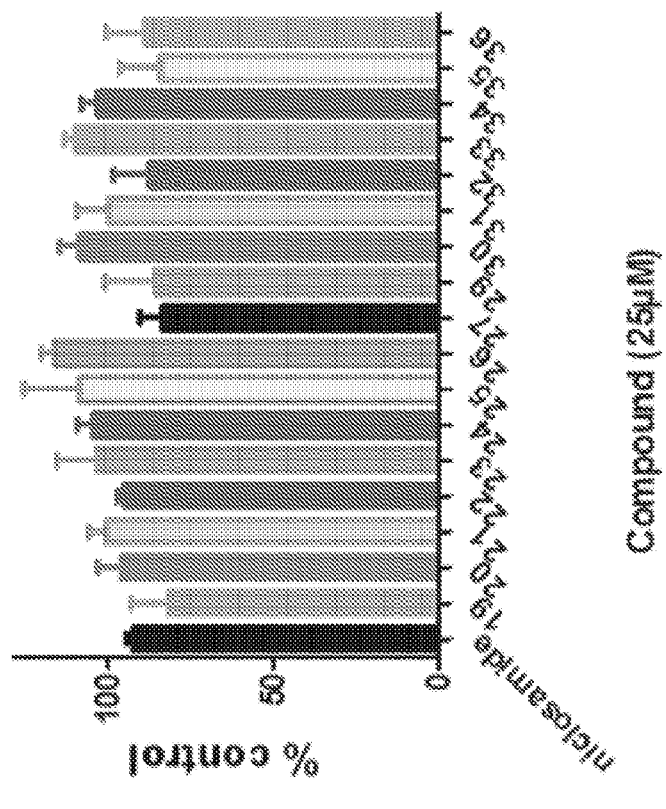
FIG. 3A shows results for fluorescence polarization (FP) assay that measures affinity for STAT3 SH2 domain. Synthesized analogs were evaluated for their ability to disrupt fluorescent peptide binding at 25 μM in the FP assay.
Figure 3B:
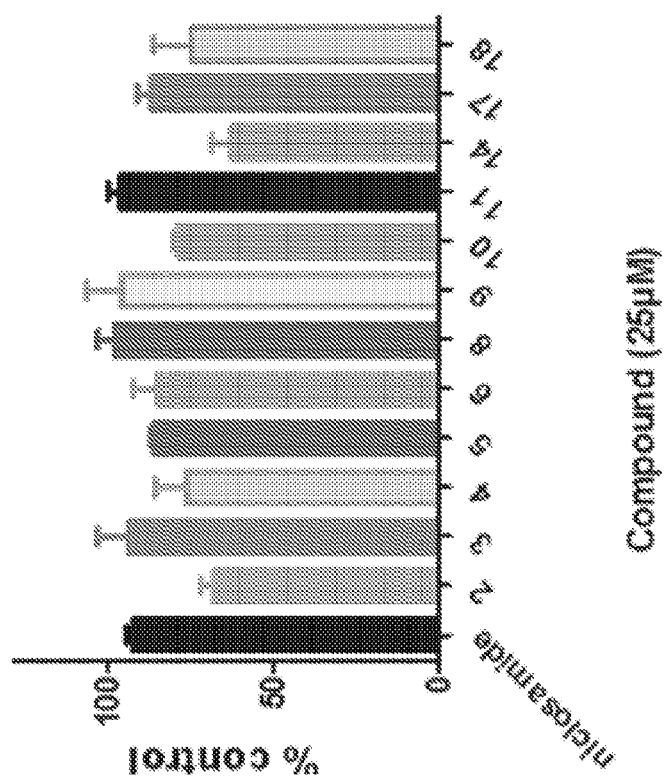
FIG. 3B shows results for fluorescence polarization (FP) assay that measures affinity for STAT3 SH2 domain. NCI compounds were evaluated for their ability to disrupt fluorescent peptide binding at 25 μM in the FP assay.

Niclosamide and Analogs do not Target the SH2 Domain of STAT3 to Varying Degrees With 30 compounds identified, we followed the tandem screening approach proposed in our previously published work (Furtek, et al., Oncotarget, 2016, supra) to evaluate their impact as STAT3 inhibitors in vitro. NCI compounds and synthesized niclosamide analogs were evaluated for their affinity for the SH2 domain of STAT3 using an FP assay. Niclosamide was included as a control as it has been previously evaluated in this assay (Id.). At a single concentration of 25 µM, no compounds reduced binding of the fluorescent peptide by 50% (FIGS. 3A and 3B). Compounds 27, 29, 35, and analogs 2, 10, and 14 demonstrated slight affinity for the SH2 domain. Analysis by one-way ANOVA determined there was no significant difference between niclosamide and its structurally similar counterparts. SH2 domain STAT3 inhibitors, such as S3I-1757, displayed complete inhibition of fluorescent peptide binding at concentrations above 10 µM, and so little to no activity at a concentration of 25 µM suggests that these compounds do not significantly inhibit STAT3 at its SH2 domain. Negative results in the FP assay excludes the SH2 domain as a site of action of these compounds, and they were next evaluated in a recombinant STAT3-DNA binding ELISA.

Example 5

A Recombinant STAT3 ELISA Identifies Compounds that Target the DNA-Binding Domain of STAT3

Figure 4B:
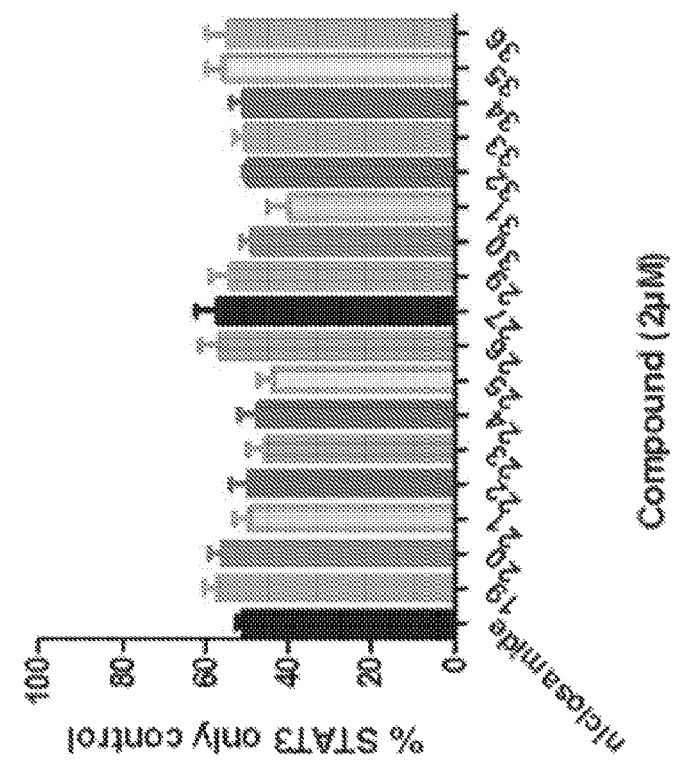
FIG. 4B shows the results of a recombinant ELISA that identifies compounds that target the DNA-binding domain of STAT3. Recombinant STAT3 protein was incubated for 1 hour with 2 μM of NCI compounds prior to evaluation by ELISA. P=0.001, *P<0.0001
Figure 4A:
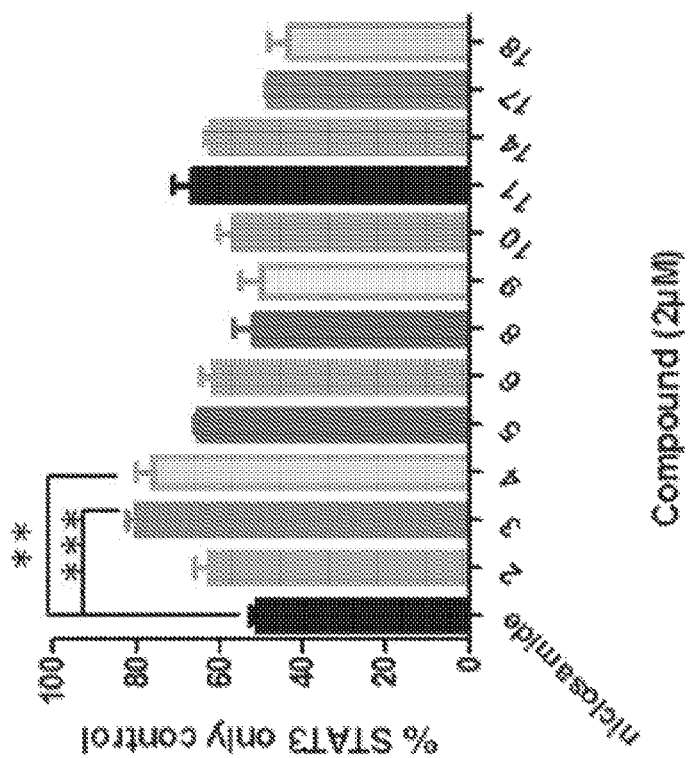
FIG. 4A shows the results of a recombinant ELISA that identifies compounds that target the DNA-binding domain of STAT3. Recombinant STAT3 protein was incubated for 1 hour with 2 μM of synthesized analogs prior to evaluation by ELISA. P=0.001, *P<0.0001

Using the workflow outlined above, compounds were next evaluated in a recombinant ELISA to determine their effects on STAT3/DNA binding. In prior studies we determined the $IC_{50}$ of niclosamide in the recombinant ELISA to be 1.93±0.70 µM (Id.). As the purpose of this study was to identify compounds that are structurally similar to niclosamide, but have equal or better potency for STAT3, compounds were tested at the recombinant $IC_{50}$ of niclosamide in this assay (2 µM). Niclosamide was also included for reference. At a concentration of 2 µM, all the evaluated compounds reduced recombinant STAT3/DNA-binding with inhibition at approximately ±15% of the activity recorded for niclosamide (FIGS. 4A and 4B). This is not a surprising result as we had chosen to test compounds with significant structural similarities to our lead molecule. Analysis by one-way ANOVA determined there was a statistically significant difference of the means ($F(31,143)=3.461$, $P<0.0001$), and a post hoc Tukey test revealed that compounds 3 and 4 were statistically different from niclosamide ($P<0.05$) (FIG. 4A). Both compounds performed worse than niclosamide in the recombinant ELISA with mean values of 80% and 76% of STAT3 only control, respectively. Taking this into account, compounds with means less than or equal to niclosamide were selected for further investigation in vitro, and were NCI compounds 21-25, 30-32, and synthesized analogs 8, 9, 17, and 18. It is worth noting that, from our computational modeling, the top hits from both sites (9, 17, and 20) were chosen for further investigation.

Example 6

Compounds 8 and 17 Inhibit STAT3-DNA Binding and Induce Apoptosis in Cells

Figure 5A:
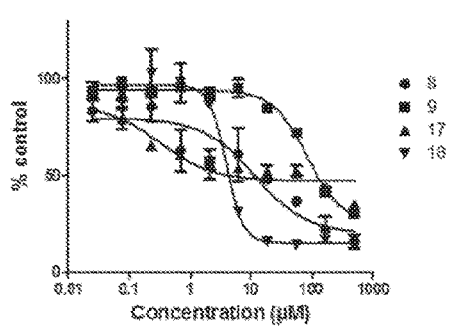
FIG. 5A shows the analysis of compounds in the inhibition of the DNA binding domain (DBD) of STAT3. HeLa cells were treated with synthesized analogs for 24 h and assessed for cell viability by MTT assay.
Figure 5B:
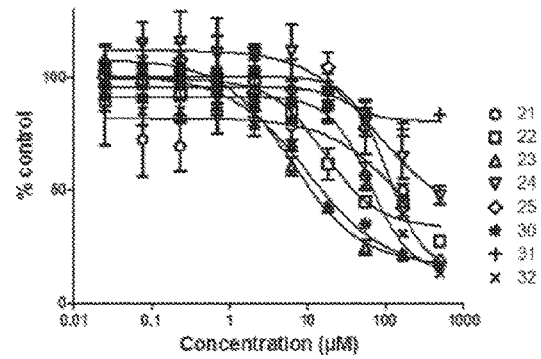
FIG. 5B shows the analysis of compounds in the inhibition of the DNA binding domain (DBD) of STAT3. HeLa cells were treated with NCI compounds for 24 h and assessed for cell viability by MTT assay.

Compounds selected for investigation in cells were first assessed for their impact on cell viability via MTT assay (FIGS. 5A and 5B). Unlike our previous methods, the purpose of the MTT in this study was to determine if any single compound had a greater impact on cell viability compared to niclosamide. As previously discussed, treatment of cells for evaluation in a cell-based ELISA is limited to inhibitor concentrations at or below their $EC_{50}$ in order to preserve cell quantity required to produce 20 µg of nuclear extract protein. Our intention was to assess these compounds in cells at the MTT $EC_{50}$ of niclosamide (1 µM); therefore, we first needed to determine if any compound had an $EC_{50}$ below this value. Compounds 8 and 17 were calculated to have an $EC_{50}$ of 1.15±0.38 µM and 0.315±0.070 µM, respectively (FIG. 5A). Although compound 17 had a calculated $EC_{50}$ below 1 µM, total cell viability did not drop below 50% until high concentrations. Thus, we concluded that we could examine STAT3/DNA-binding inhibition in cells following a single 24-hour treatment at 1 µM for all compounds.

Figure 5C:
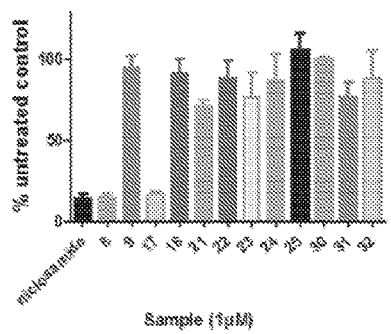
FIG. 5C shows the results of a cell-based ELISA of HeLa cells dosed for 24 h with 1 μM of compounds.
Figure 5D:
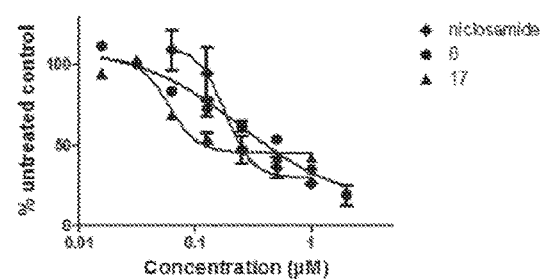
FIG. 5D shows the dose-response curve for HeLa cells treated with niclosamide, and compounds 8 and 17 for 24 h.

Confluent plates of HeLa cells were treated with compounds for 24 hours prior to preparation of nuclear extracts. In a cell-based ELISA, niclosamide, 8, and 17 reduced STAT3/DNA-binding by approx. 80% at concentrations of 1 µM (FIG. 5C), and so dose responses were determined for these three compounds: niclosamide $EC_{50}$=179±28 nM, 8 $EC_{50}$=239±39 nM and 17 $EC_{50}$=59±11 nM (FIG. 5D). Compared with niclosamide, compound 8 was slightly less potent, while 17 was more than twice as potent as our lead in this assay. Looking at the computational modeling, this potency may suggest the DBD site as the target site as opposed to the LD, based on binding orientations of compounds 8 and 17 compared to niclosamide. Compound 8 does not appear to have a favorable binding position within the DBD, while it appears to bind acceptably in the LD site. In contrast, compound 17 appears to have favorable binding positions in both sites. While it is optimistic to believe that 17 targets only one binding site within the DNA-binding region of STAT3, it is also possible that it binds in both sites and thus induces a greater conformational change of the protein to inhibit DNA interactions. Without X-ray crystallography and further structural biology experiments for confirmation, the only conclusion that can be made is that compound 17 potently inhibits STAT3/DNA-binding.

Figure 5E:
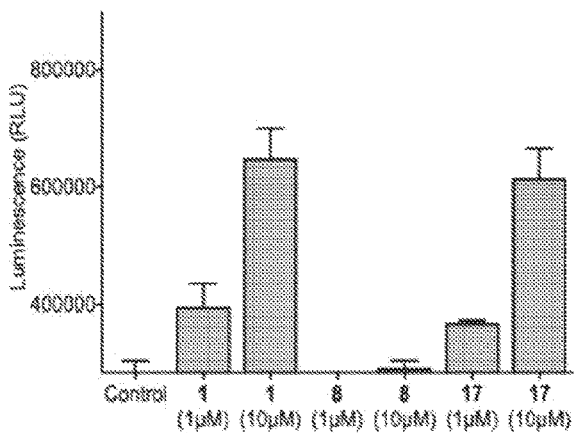
FIG. 5E shows the results of an experiment measuring the induction of apoptosis after 24 h treatment with niclosamide, compound 8, or compound 17, at 1 μM and 10 μM each.
Figure 5F:
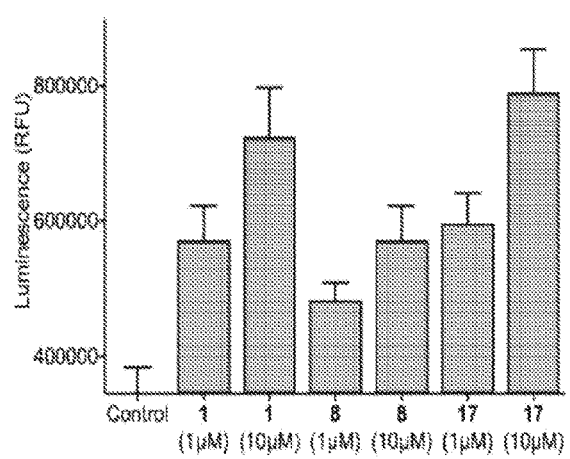
FIG. 5F shows the results of an experiment measuring the induction of apoptosis after 48 h treatment with niclosamide, compound 8, or compound 17, at 1 μM and 10 μM each.

Once it had been determined that compounds 8 and 17 potently inhibit STAT3/DNA-binding, we examined the potential of these compounds to induce apoptosis in cells. Constitutively active STAT3 can drive anti-apoptosis, and induction of apoptosis is a downstream marker of STAT3 inhibition. HeLa cells were treated with 8, 17, or niclosamide as single agents at concentrations of 1 and 10 µM for 24 and 48 hours. As single agent treatments, 10 µM of 8 and 1 µM of 17 displayed a time-dependent increase in apoptosis (FIGS. 5E and 5F). Niclosamide at 1 µM demonstrated only a slight increase in apoptosis compared to untreated control at both 24 and 48 hours. At 10 µM, niclosamide induced twice as much apoptosis compared to untreated control and this response was the same for both time points (FIGS. 5E and 5F).

These data demonstrate the identification of 30 potential analogs of niclosamide using both computational screening and in silico compound design. Using our previously established tandem screening approach, we validated the computational models and identified the site of action to be the DBD of STAT3. We have demonstrated that niclosamide, 8, and 17 inhibit STAT3/DNA-binding in vitro, and that 17 is a more potent DNA-binding inhibitor in cells than our lead.

Example 7

STAT3 Inhibition Regulates Mitochondrial Energy Function Through Mitochondrial Gene Regulation Acute myeloid leukemia (AML) is an aggressive disease with a dismal prognosis. This is largely due to high relapse rates, which stem from the inability to eliminate leukemia stem cells (LSCs) with conventional chemotherapy.

One key vulnerability of LSCs is their dependence on oxidative phosphorylation (OXPHOS). Although STAT3 has been classically studied as a transcription factor that regulates self-renewal and proliferation, it has also been shown to play an essential role in OXPHOS via regulation of the electron transport chain (ETC). Given this protein is overexpressed in AML, and LSCs are dependent on OXPHOS, it is an appealing target for this disease. We therefore tested the mechanism by which STAT3 inhibition regulates mitochondrial energy production, which may be twofold: via direct regulation of the ETC, as well as through regulation of multiple genes involved in proper mitochondrial function.

We used STAT3 inhibitors of this disclosure, as well as genetic knockdown of STAT3, in primary AML samples to test the effects of targeting this protein. Flow cytometry, colony forming potential, and engraftment of primary samples on PDX mouse models were performed to assess therapeutic efficacy upon treatment with SF25. RNAseq, seahorse assays, and metabolomics experiments were also performed to determine downstream effects of targeting STAT3.

Figure 6:
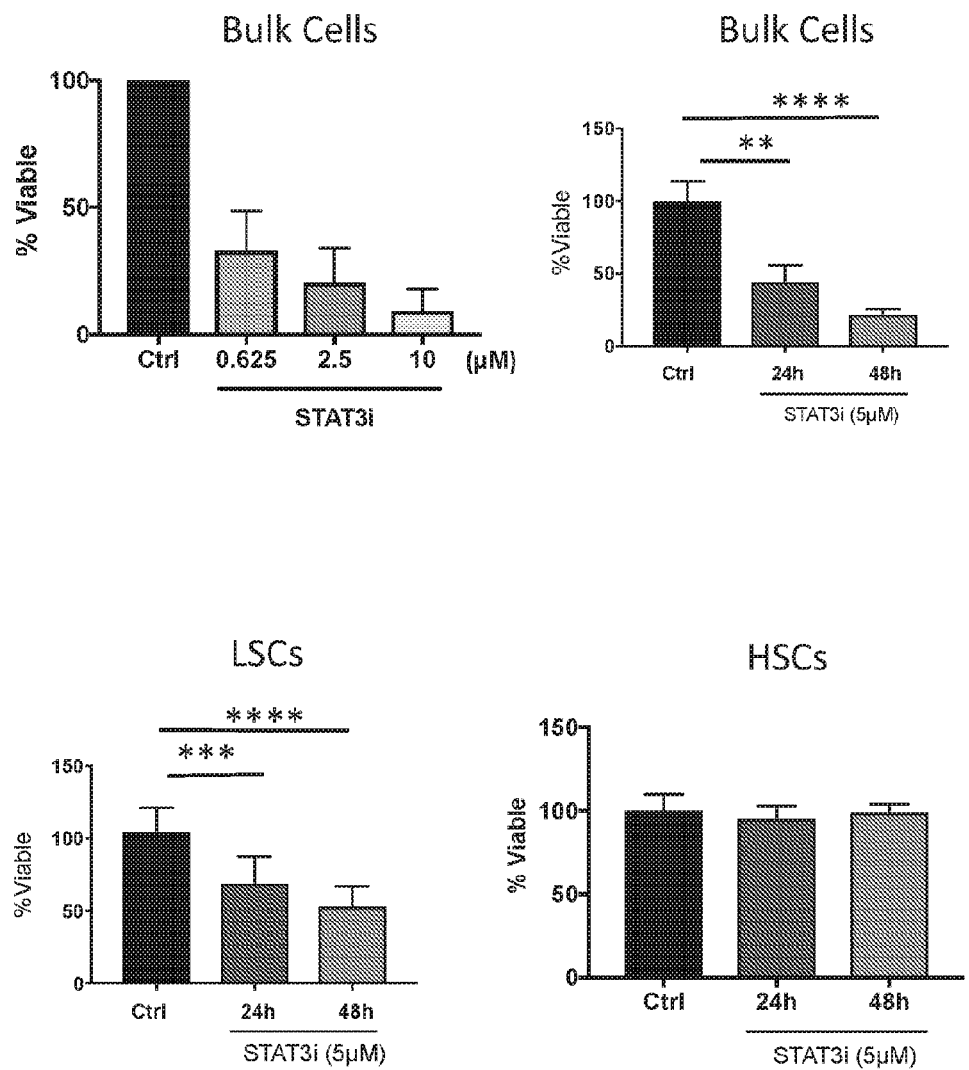
FIG. 6 shows the results of viability testing of LSCs with STAT3 inhibitors of this disclosure compared to HSCs.
Figure 7:
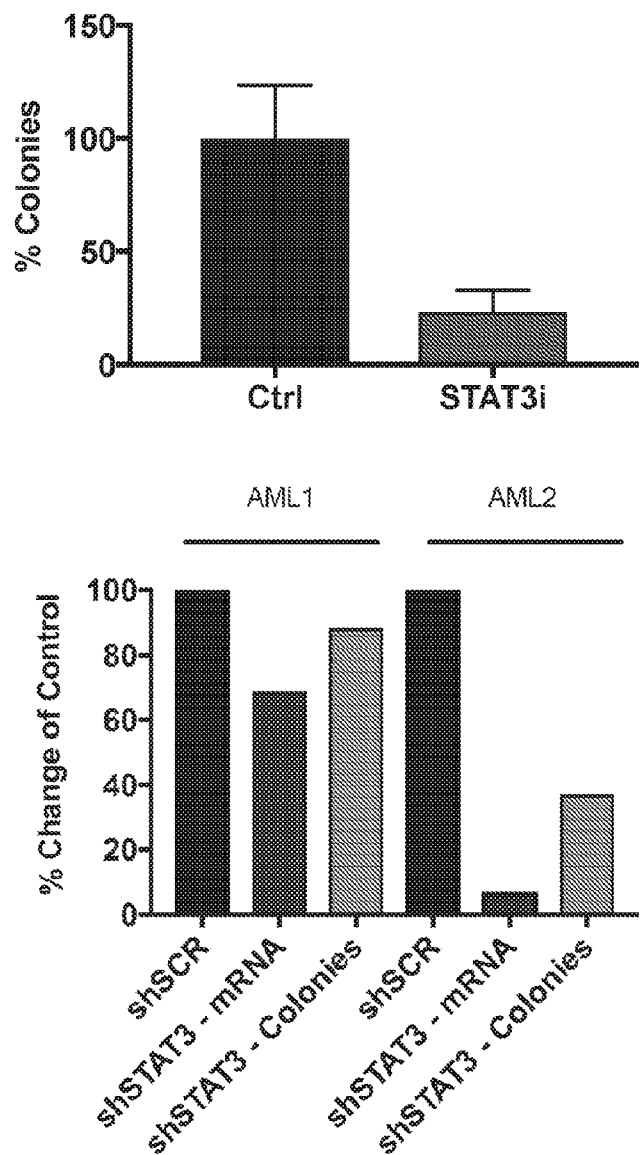
FIG. 7 shows the results of colony formation testing with STAT3 inhibitors of this disclosure and RNA inhibition by shSTAT3.
Figure 8:
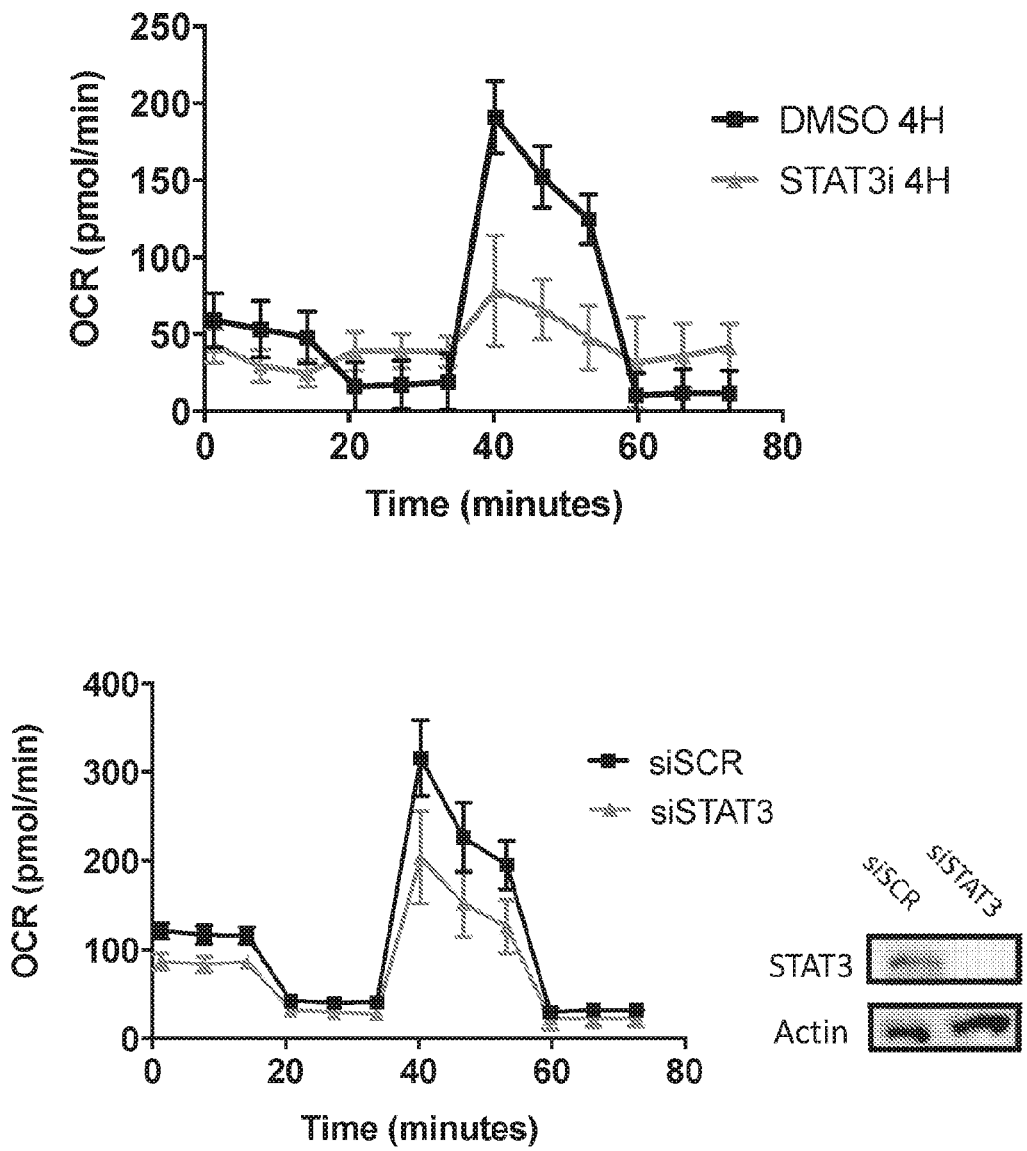
FIG. 8 shows that STAT3 inhibitors of this disclosure and RNA inhibition by siSTAT3 compromise mitochondrial function.
Figure 9A:
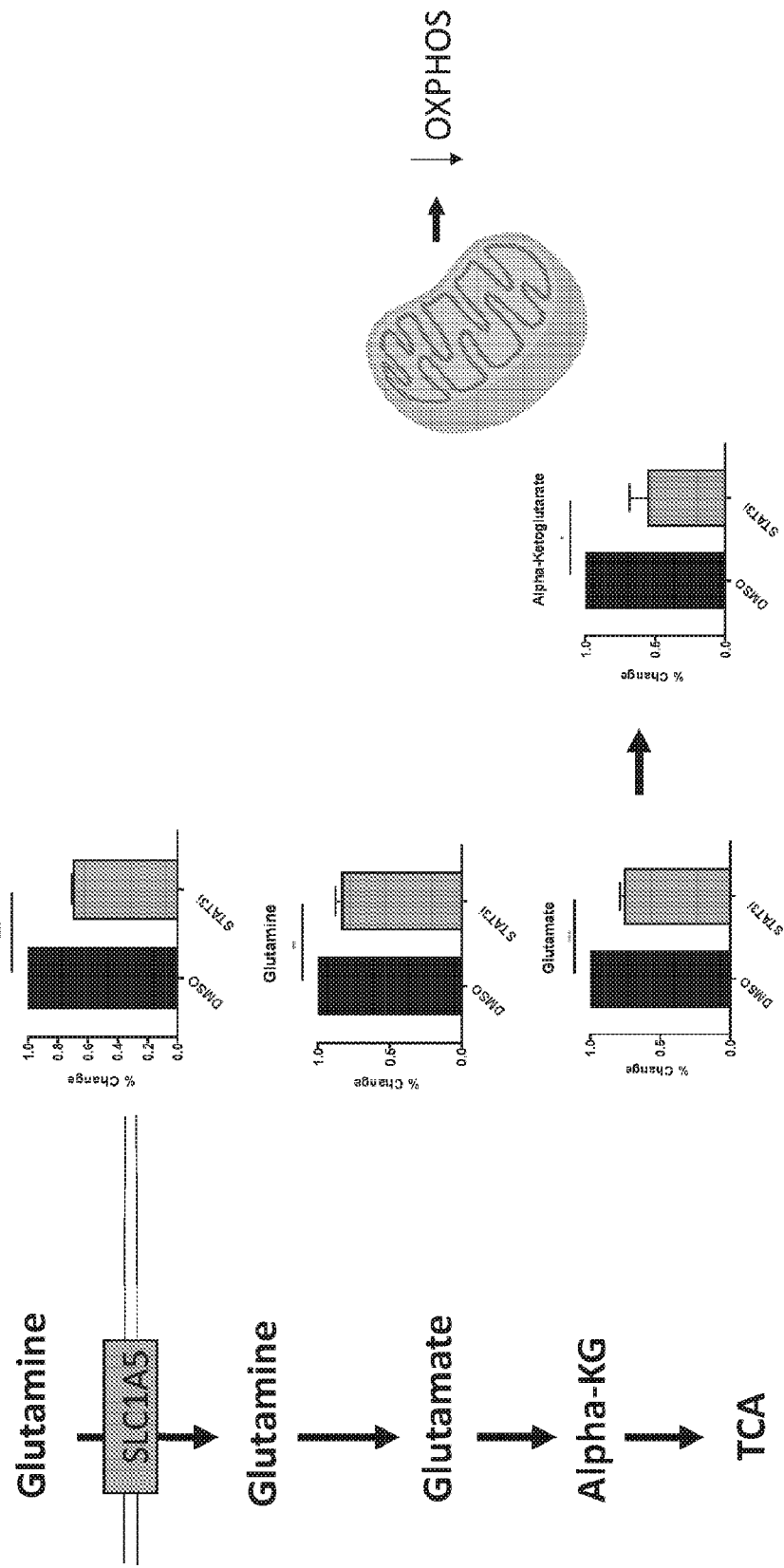
FIGS. 9A, 9B and 9C show the effects of STAT3 inhibitors of this disclosure on the metabolomics of mitochondria.
Figure 9B:
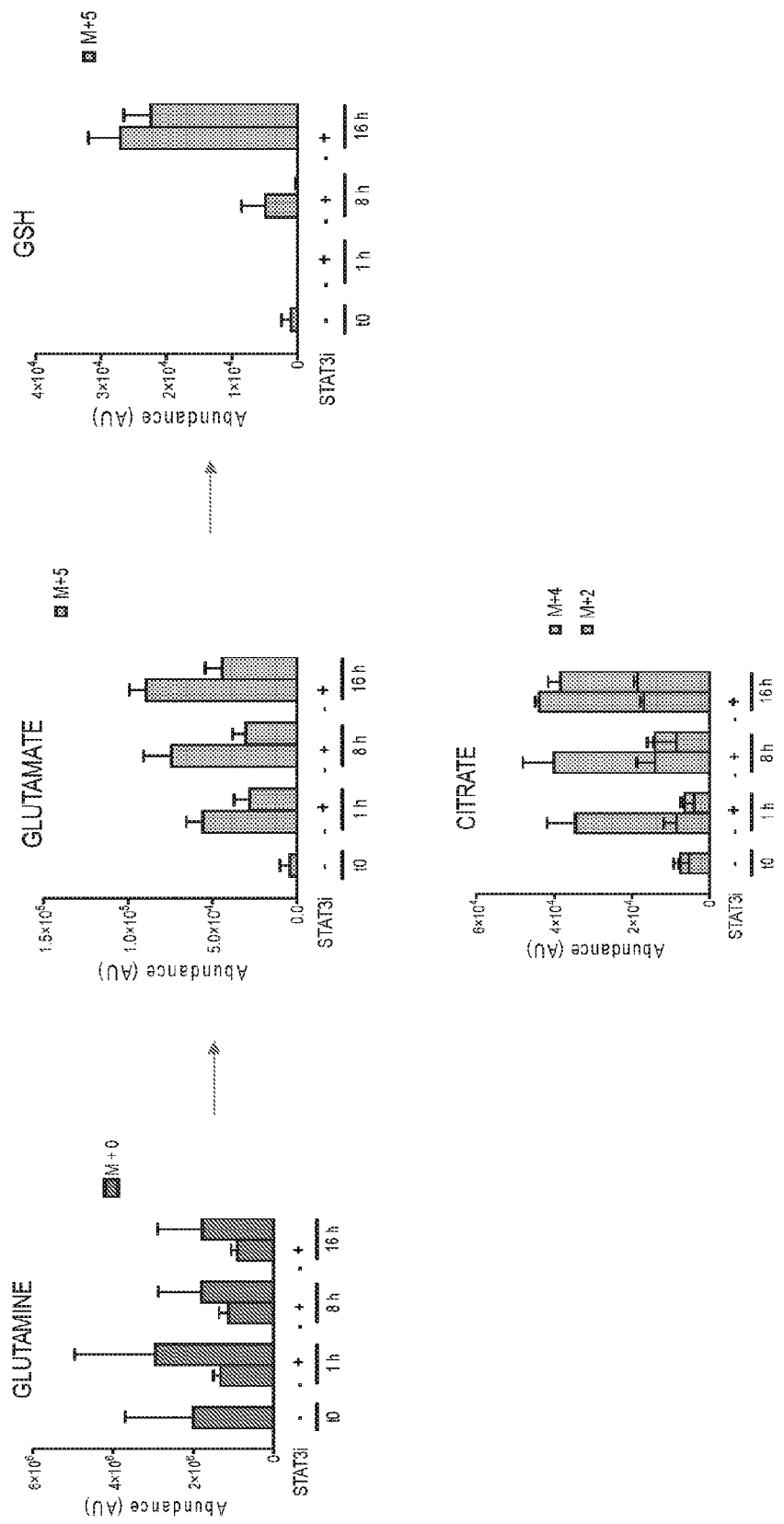
Figure 9C:
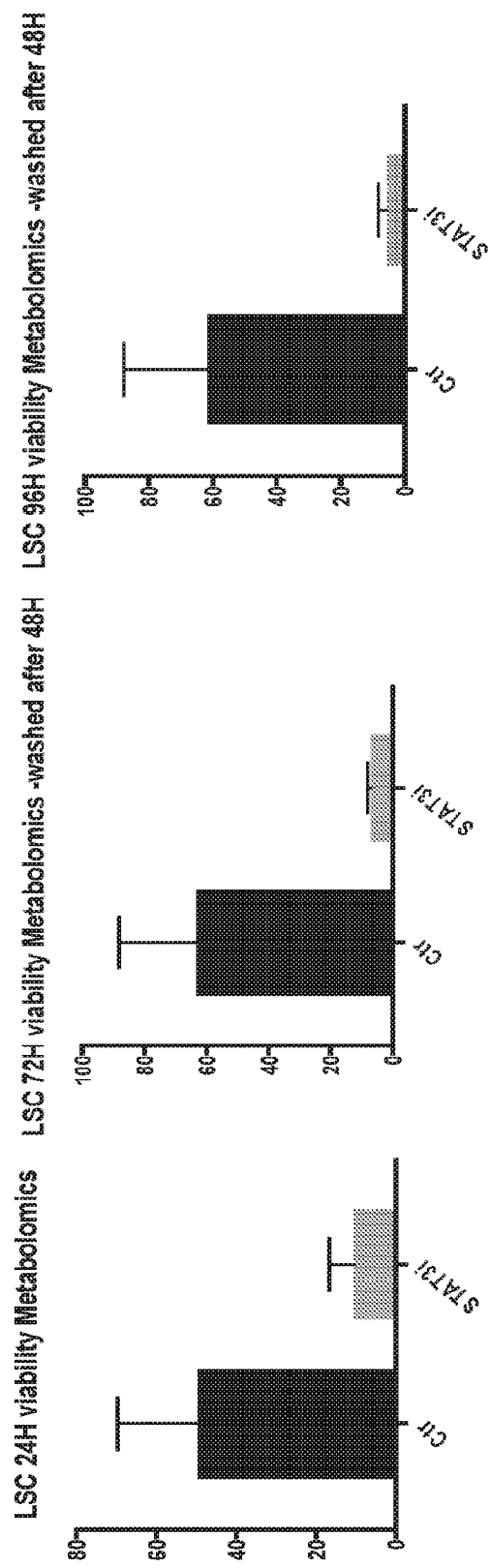

Inhibition of STAT3 in primary AML samples led to decreased cell viability (FIG. 6) and colony forming potential (FIG. 7), while not affecting normal hematopoietic stem cells (HSCs). This effect appears to be a result of mitochondrial dysfunction in LSCs, as seen by a significant decrease in oxygen consumption rate (OCR) of STAT3 depleted cells (FIG. 8). The mitochondrial dysfunction and reduction in OXPHOS were mediated by the downregulation of several mitochondrial and nuclear encoded genes that are important for oxidative phosphorylation, including the glutamine transporter SCL1A5, which ultimately leads to a decrease in TCA cycle intermediates (FIGS. 9A-9C).

Acute myeloid leukemia is an aggressive disease, largely due to the presence of a chemo-resistant population of leukemia stem cells, and these data demonstrate that LSCs highly depend on proper mitochondrial function and OXPHOS, a process that is partly regulated by STAT3. Inhibition of STAT3 is therefore an effective way of eliminating this population, making this a promising new target in the treatment of AML.

Example 8

Inhibition of STAT3 Leads to Apoptosis of LSCs while not Affecting HSCs

Figure 10:
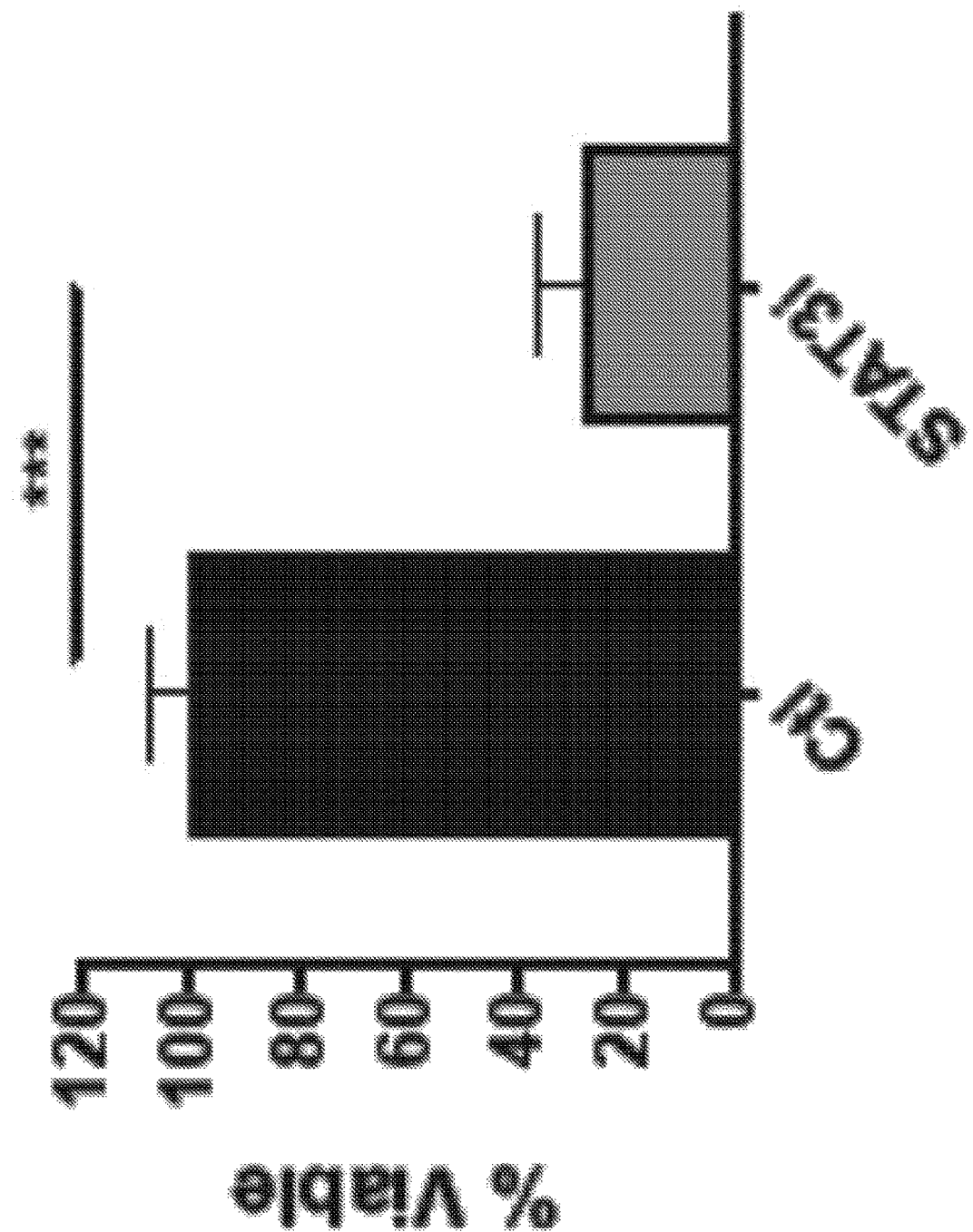
FIG. 10 is a graph showing cell viability of leukemia stem cells (LSCs) following treatment with compound 17 of the present disclosure.
Figure 11:
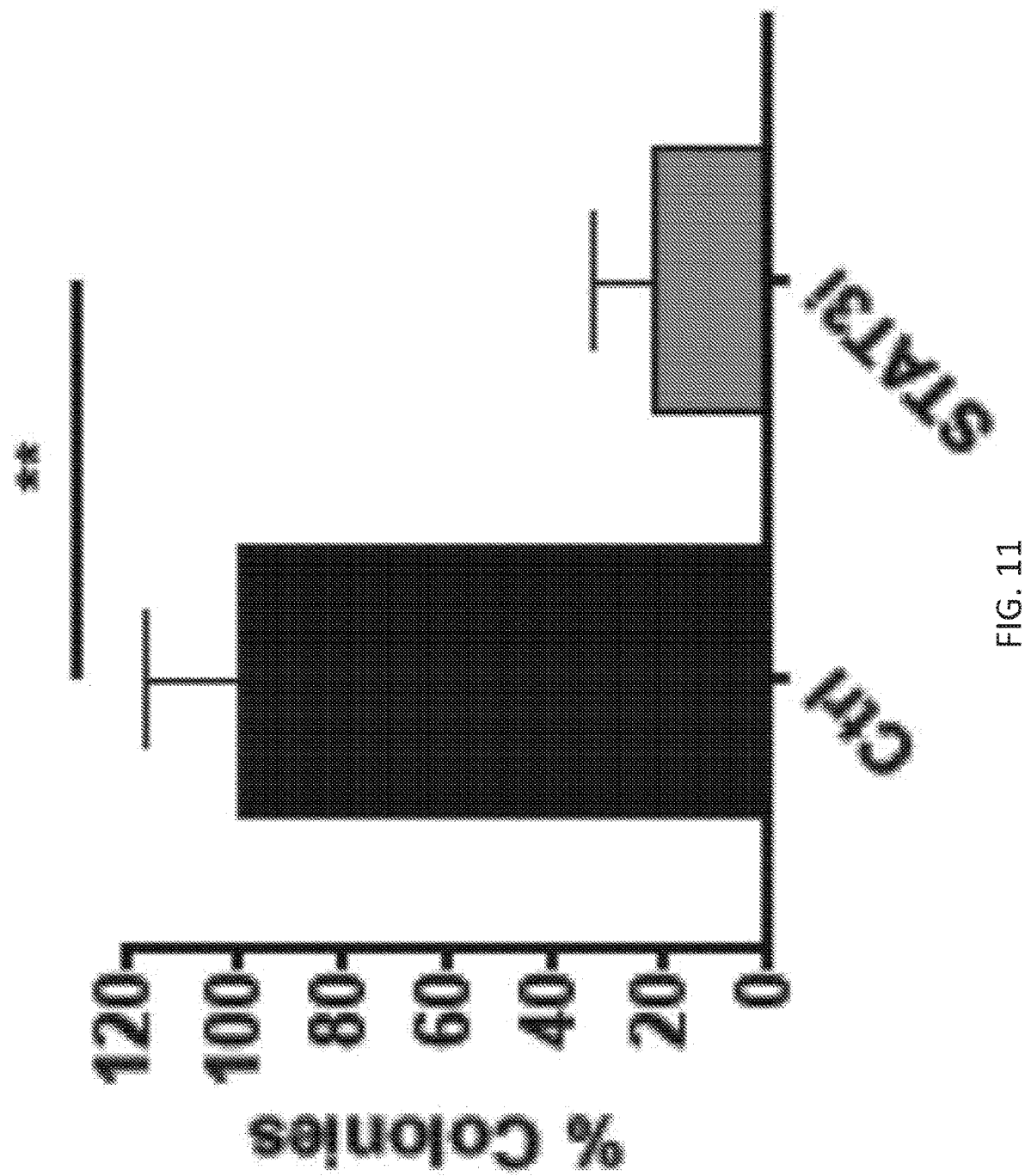
FIG. 11 is a graph showing colony formation of primary human AML cells treated with compound 17 of the present disclosure.
Figure 12:
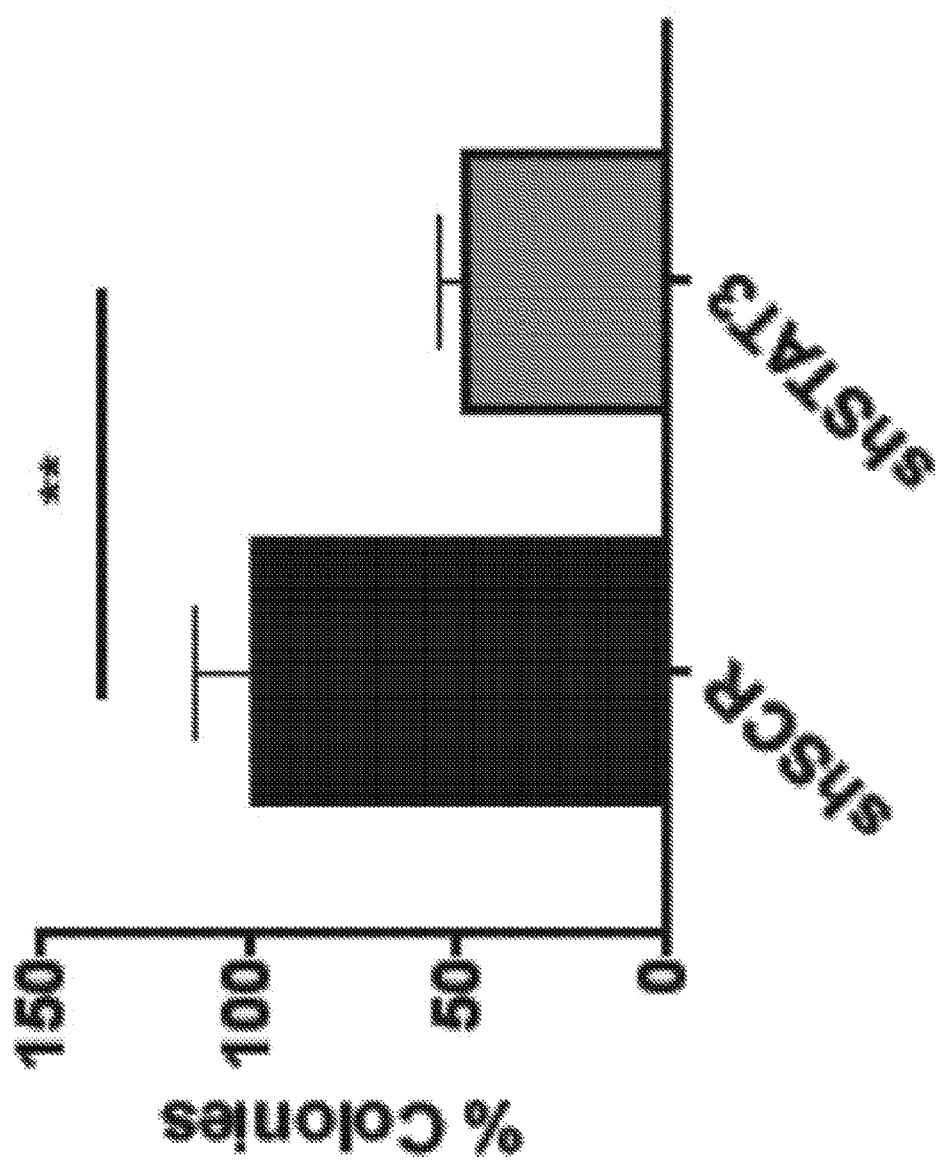
FIG. 12 is a graph showing colony formation of primary human AML cells following shRNA-mediated knockdown of STAT3.
Figure 13:
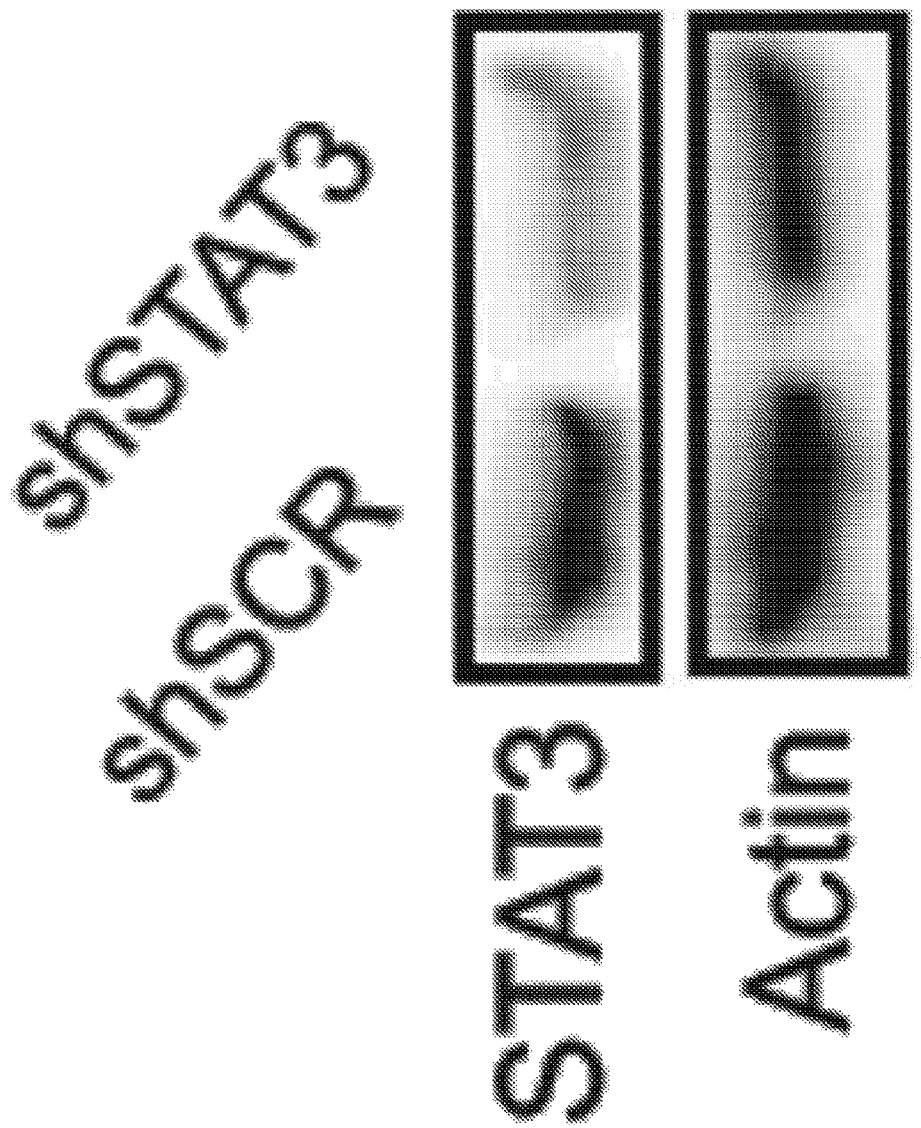
FIG. 13 is an image of western blot analysis of shRNA-mediated knockdown of STAT3 in primary human AML cells.

Leukemia Stem cells (LSCs) were incubated with compound 17 (STAT3i) for 24 hours and cell viability was measured. As shown in FIG. 10, STAT3i treatment leads to significant cell death based on apoptosis markers measured using flow cytometry. Primary human AML cells were treated with compound 17 (STAT3i). The cells were then cultured on methylcellulose and colony formation was measured. As shown in FIG. 11, STAT3i treatment leads to a significant decrease in colony formation. STAT3 was knocked down in primary human AML samples using shRNA methods (shSTAT3). As shown in FIG. 12, the knockdown of STAT3 leads to decreased colony formation. The knockdown of STAT3 was verified using western blot analysis, as shown in FIG. 13.

Figure 14:
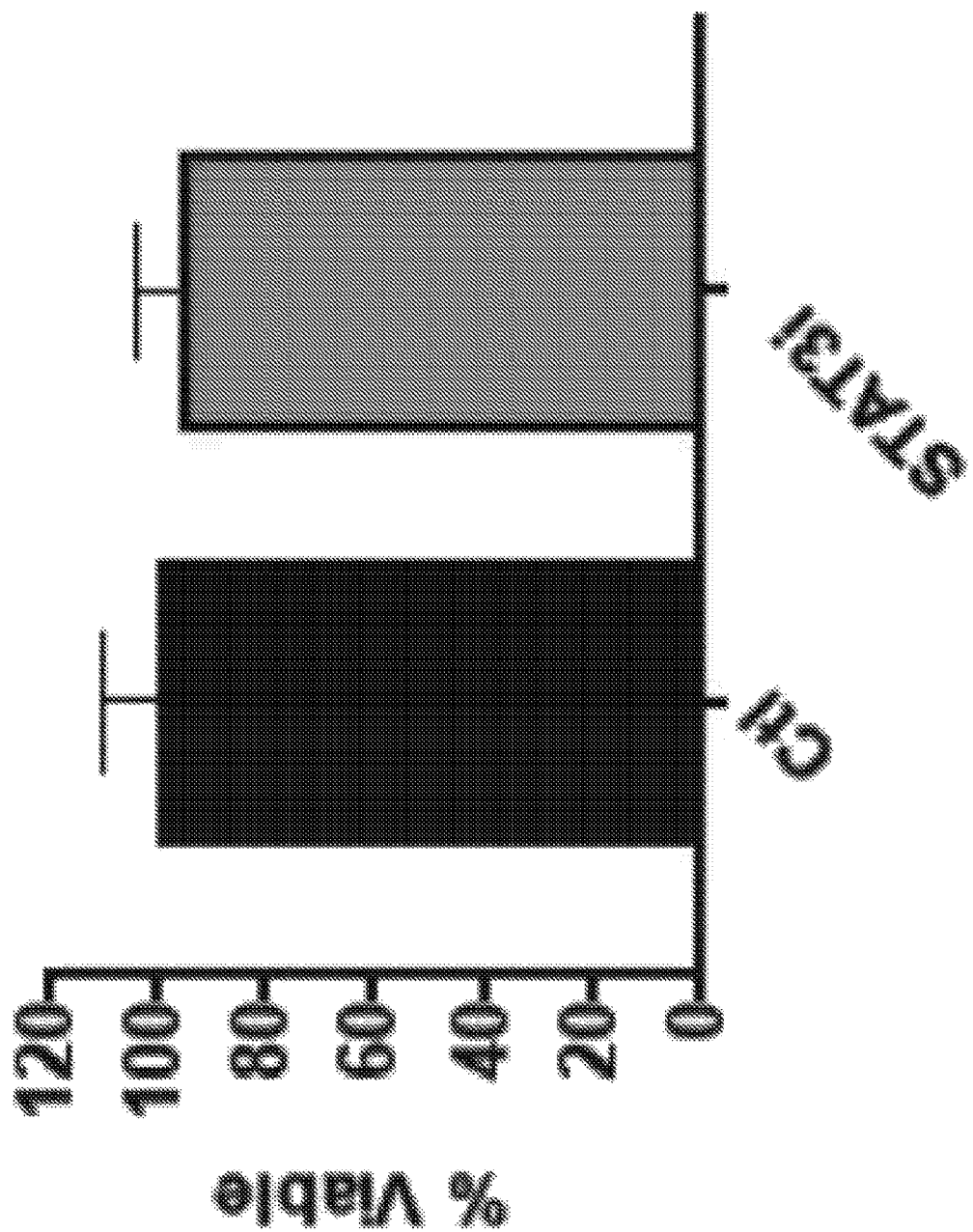
FIG. 14 is a graph showing cell viability of Cord-blood derived CD34+ normal hematopoietic stem cells treated with compound 17 of the present disclosure.
Figure 15:
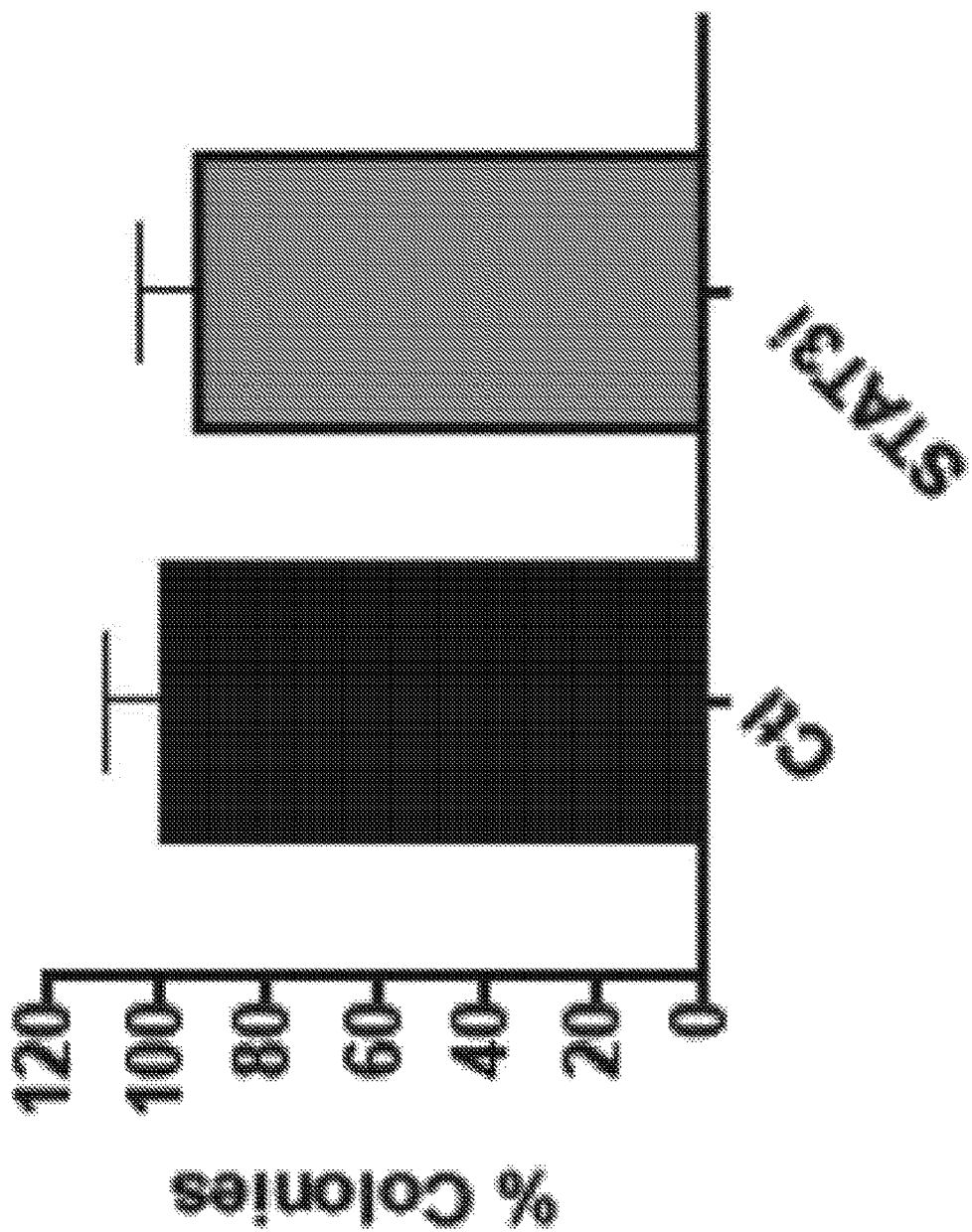
FIG. 15 is a graph showing colony formation of Cord-blood derived CD34+ normal hematopoietic stem cells treated with compound 17 of the present disclosure.

Cord-blood derived CD34+ normal hematopoietic stem cells were treated with compound 17 (STAT3i). FIG. 14 shows that the viability of the CD34+ normal hematopoietic stem cells was not affected by treatment with compound 17. FIG. 15 shows that the colony formation of the CD34+ normal hematopoietic stem cells was not affected by treatment with compound 17.

Figure 16:
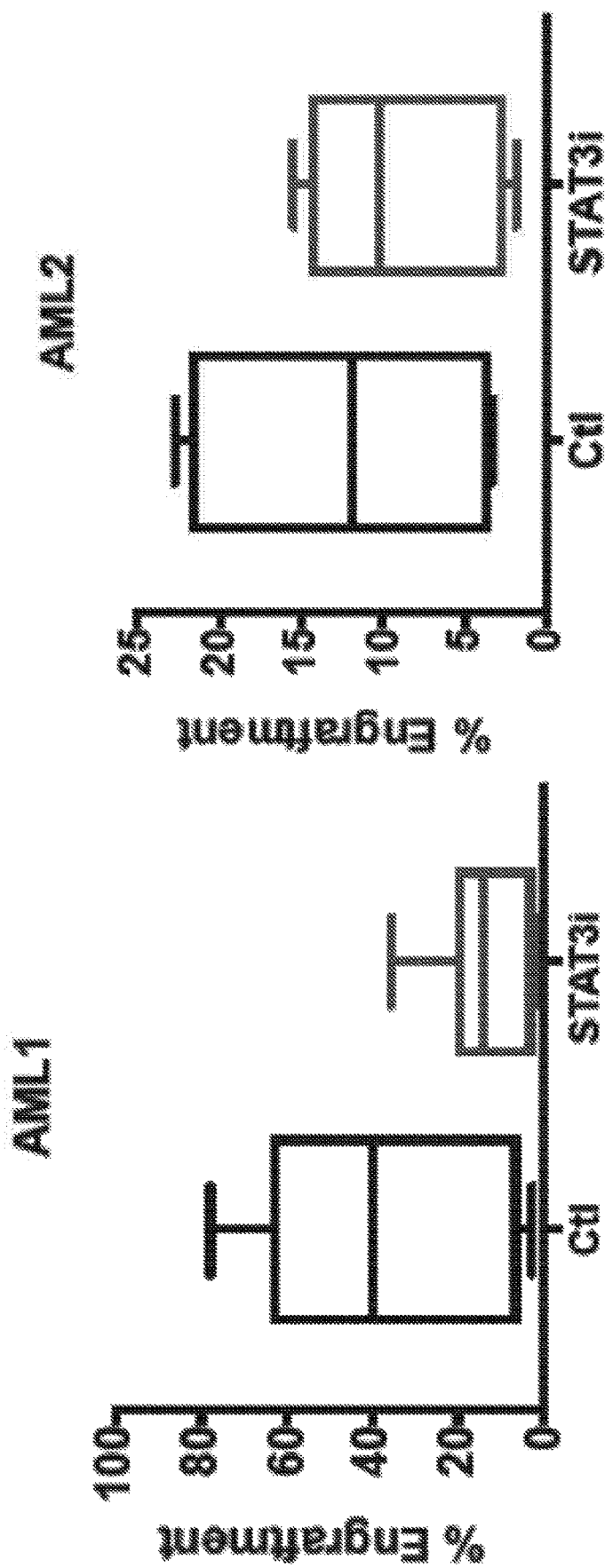
FIG. 16 is a series of graphs showing the engraftment of primary AML cells treated with compound 17 of the present disclosure.

Primary AML cells were treated with compound 17 (STAT3i) and transplanted into immunodeficient mice. FIG. 16 shows that treatment with compound 17 results in decreased engraftment of the primary AML cells.

These results indicate that compound 17, and other compounds of the present disclosure, can be effectively used as an anti-cancer treatment, including an anti-AML treatment.

Example 9

Figure 17:
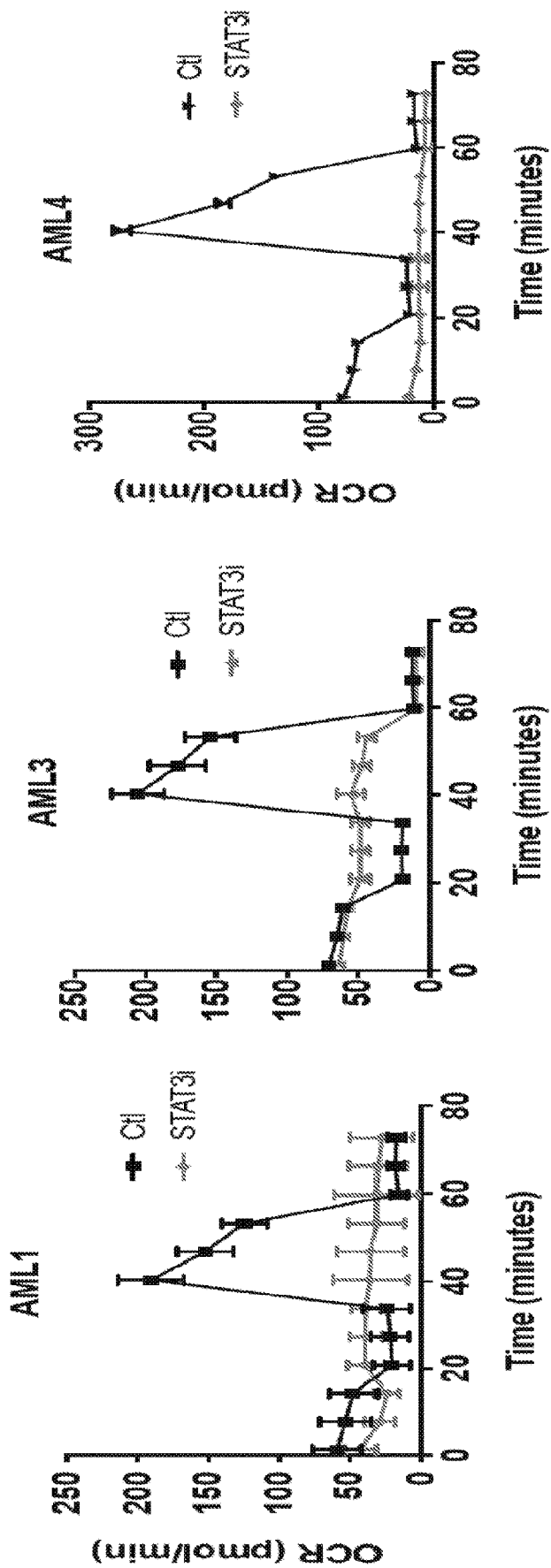
FIG. 17 is a series of graphs showing oxygen consumption rates in leukemia stem cells treated with compound 17 of the present disclosure.
Figure 18:
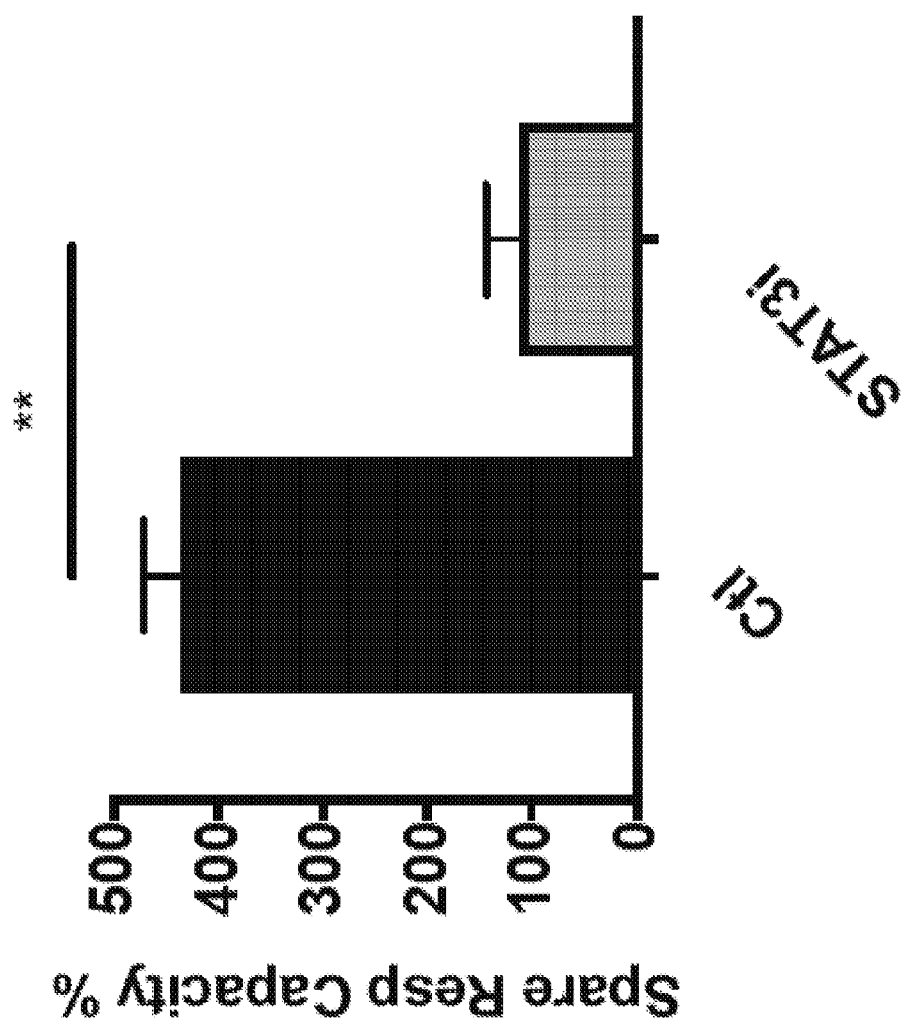
FIG. 18 is a chart showing the average change in respiratory capacity of the three samples shown in FIG. 17.
Figure 19:
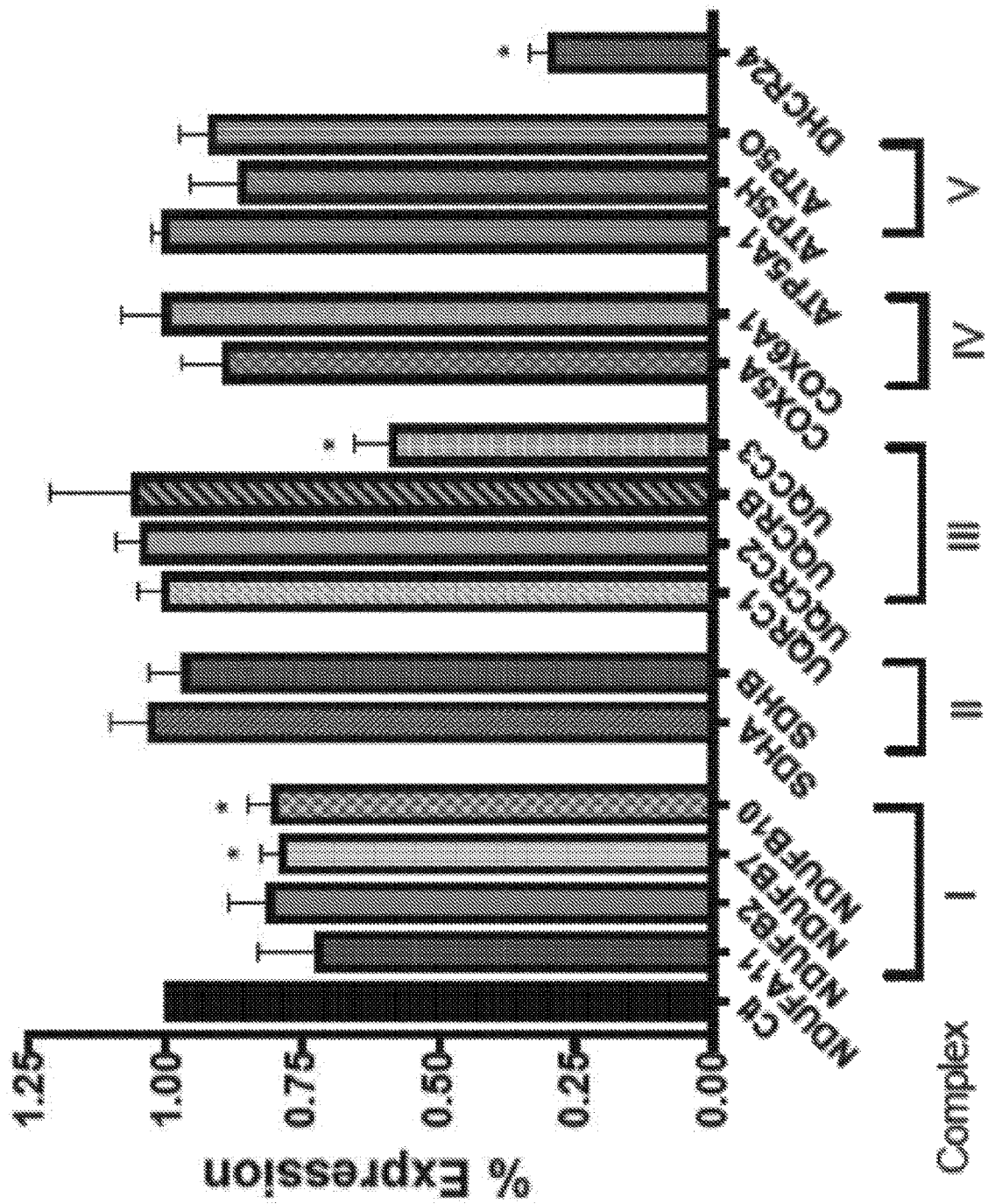
FIG. 19 is a chart showing the expression changes of various genes involved in OXPHOS after incubation with compound 17.
Figure 20:
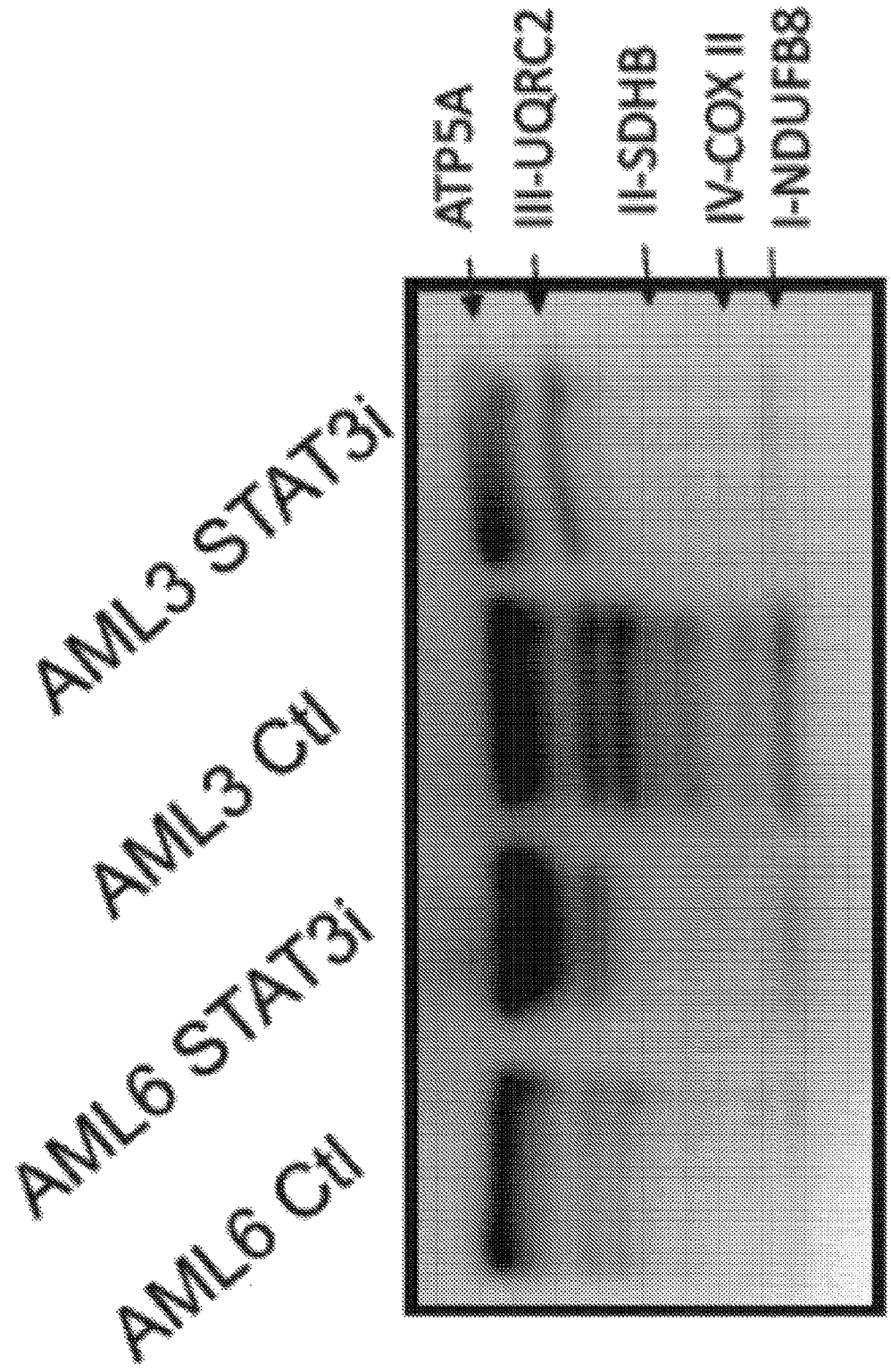
FIG. 20 is an image of western blot analysis of the expression of electron transport chain genes after incubating cells with compound 17.

STAT3 Modulates Mitochondrial Function of LSCs by Affecting Critical Mitochondrial Genes Leukemia stem cells (LSCs) were incubated with compound 17 (STAT3i) for four hours. Seahorse assays were then used to measure oxygen consumption. As shown in FIG. 17, STAT3i treatment leads to a decrease in oxygen consumption in LSCs. The average change in respiratory capacity of the samples of FIG. 17 is shown in FIG. 18. RNAseq analysis also showed a decrease in the expression of OXPHOS and mitochondrial matrix genes after treatment with compound 17. Flow cytometry analysis verified that there was no cell death at the time of RNAseq analysis. FIG. 19 is a chart showing the expression changes of various genes involved in OXPHOS after incubation with compound 17. FIG. 20 is an image of western blot analysis of the expression of electron transport chain genes after incubating cells with compound 17. These results indicate that the compounds of the present disclosure, including compound 17, modulate mitochondrial function of LSCs by affecting critical mitochondrial genes.

Example 10

Inhibition of STAT3 Affects Glutaminolysis

Figure 21:
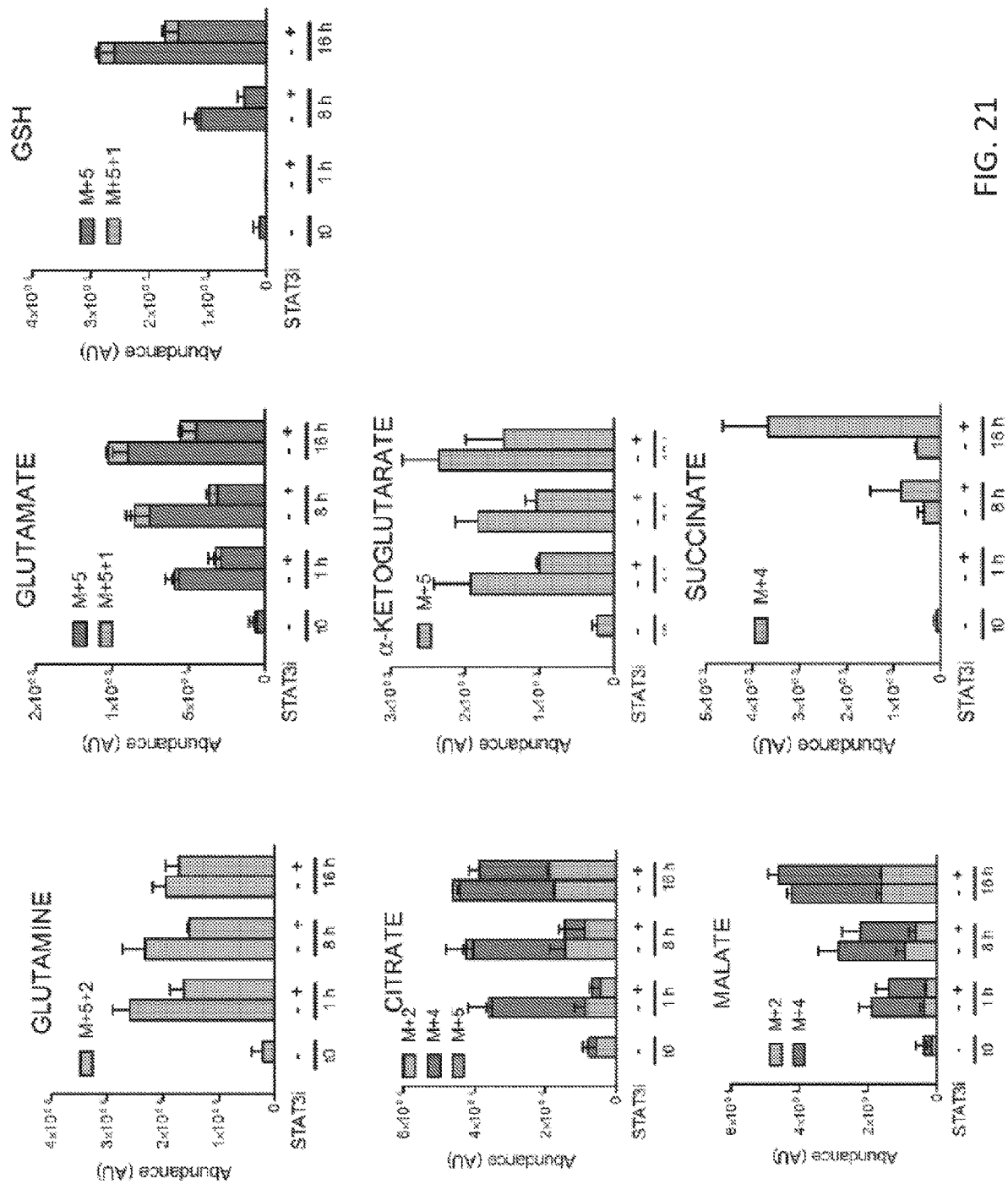
FIG. 21 is a series of graphs showing TCA cycle metabolites in primary AML samples treated with compound 17 of the present disclosure.
Figure 22:
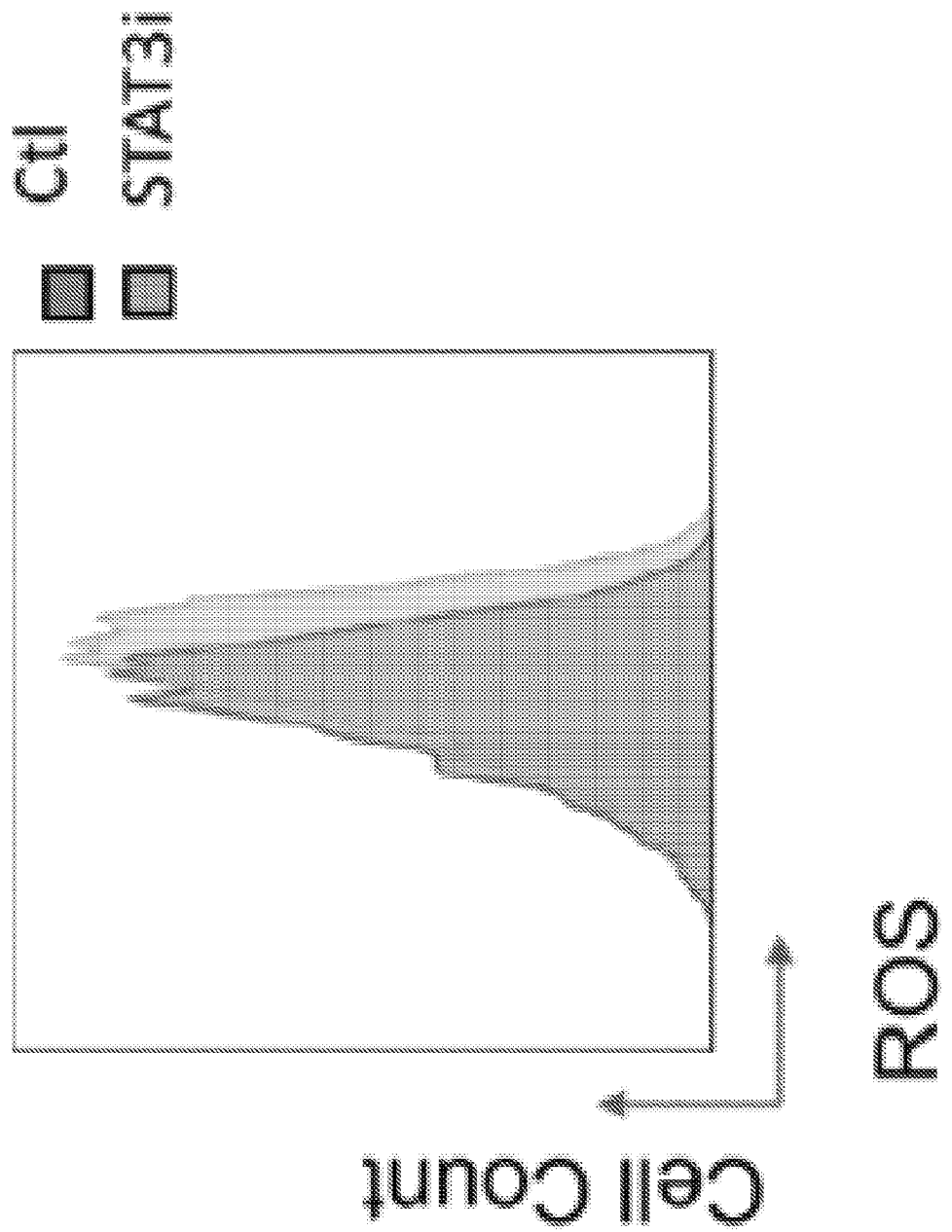
FIG. 22 is a graph showing the level of reactive oxygen species (ROS) in primary AML samples treated with compound 17 of the present disclosure.
Figure 23:
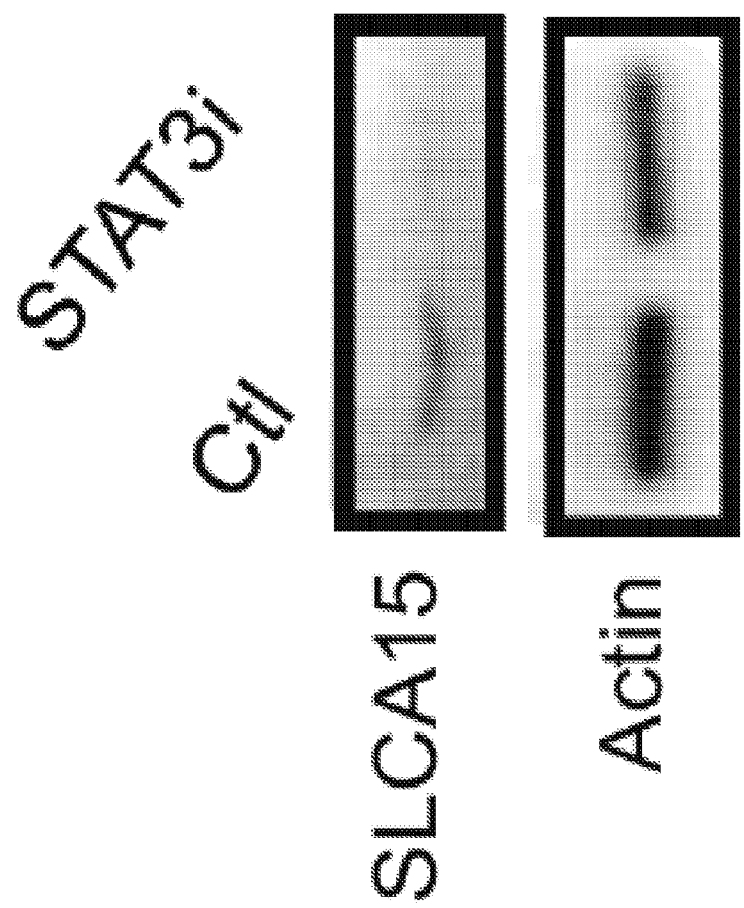
FIG. 23 is a western blot image showing SLCA15 expression in primary AML samples treated with compound 17 of the present disclosure.

Primary AML samples were incubated with heavy labeled glutamine in flux experiments aimed at measuring TCA cycle metabolites. As shown in FIG. 21, treatment of the primary AML samples with compound 17 (STAT3i) resulted in a decrease in TCA cycle metabolites, suggesting that glutaminolysis is affected by the inhibition of STAT3i by compound 17. FIG. 22 is a graph showing that reactive oxygen species (ROS) is increased in AML cells that were treated with compound 17 (STAT3i). FIG. 23 is a western blot image showing that SLCA15 is downregulated in primary AML samples upon treatment with compound 17.

Example 11

STAT3 Affects Glutaminolysis Likely Through Regulation of Myc

Figure 24:
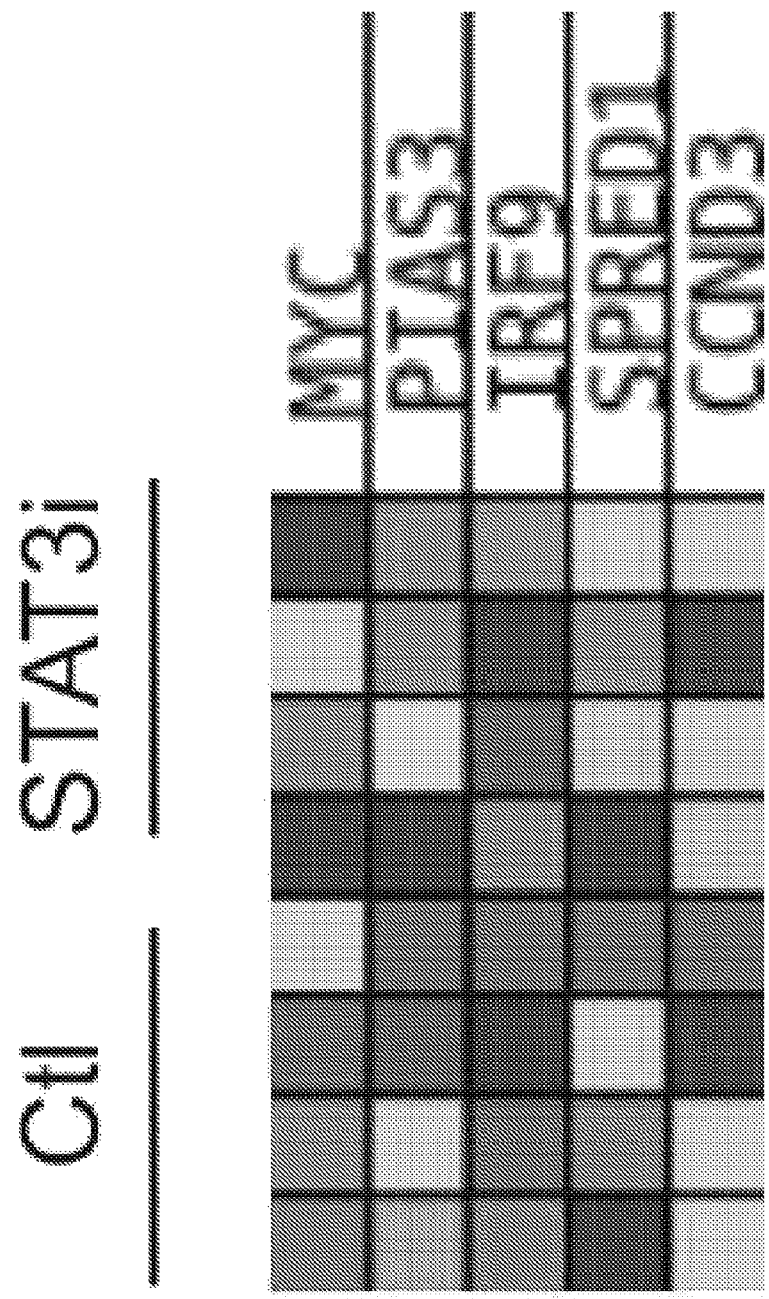
FIG. 24 is a heatmap showing the results of RNAseq analysis of leukemia stem cells (LSCs) treated with compound 17 of the present disclosure.
Figure 25:
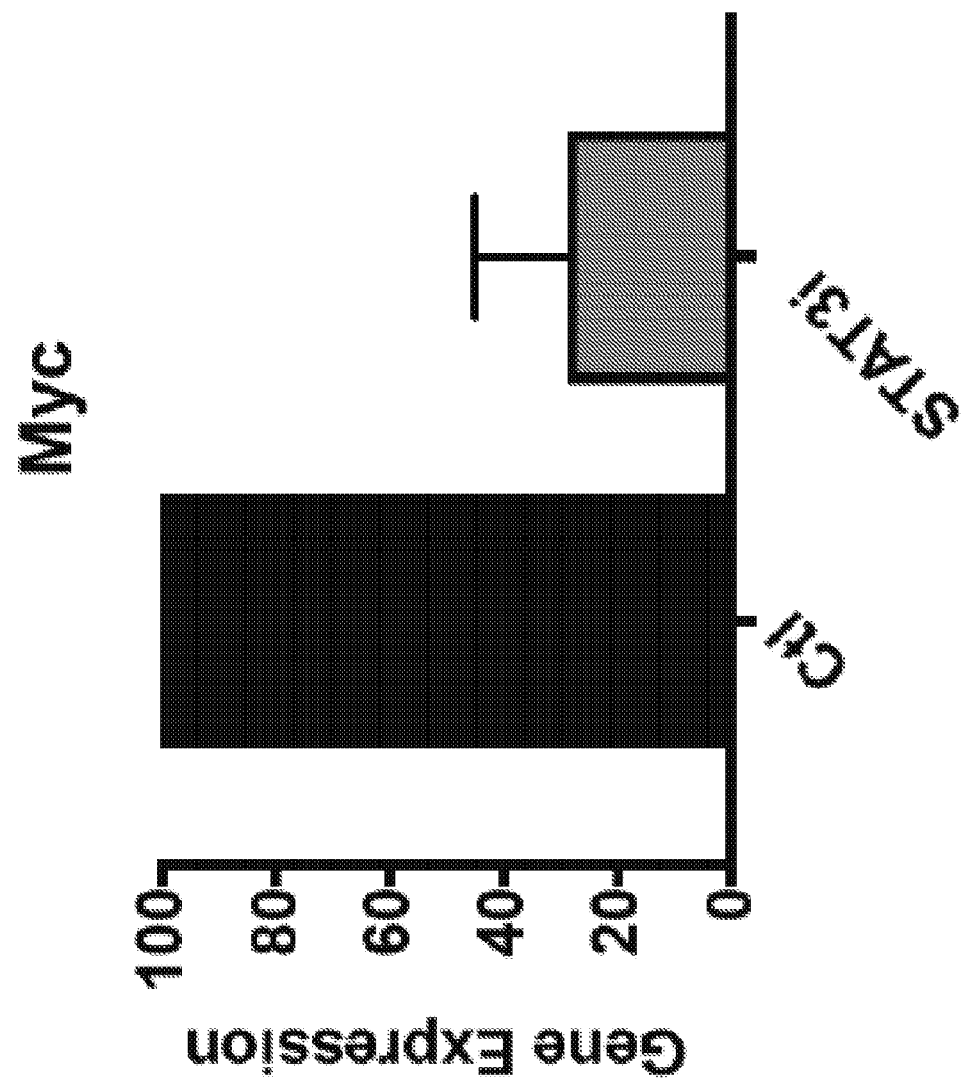
FIG. 25 is a graph showing the expression of Myc in LSCs treated with compound 17 of the present disclosure using qPCR.
Figure 26:
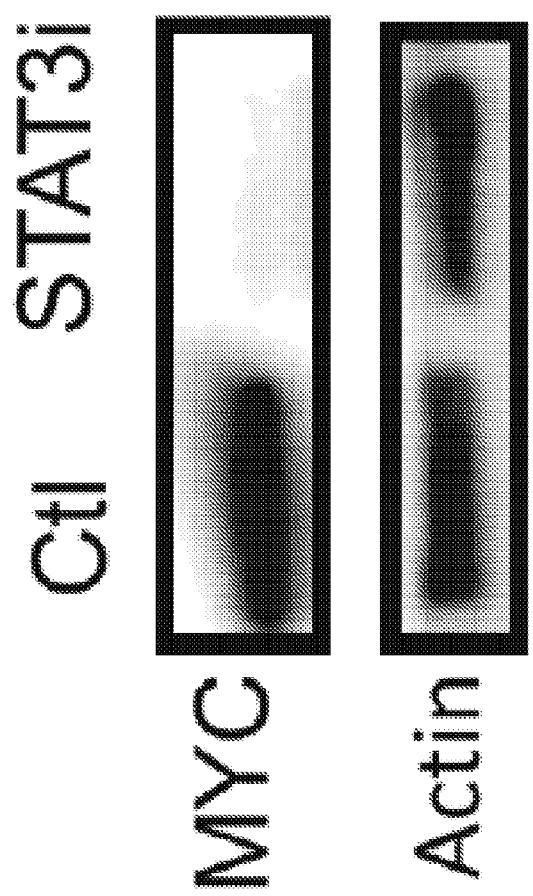
FIG. 26 is a western blot image showing Myc expression in LSCs treated with compound 17 of the present disclosure.

Leukemia stem cells (LSCs) were incubated with compound 17 (STAT3i) and RNAseq analysis was subsequently performed. As shown in FIG. 24, Myc expression is decreased following treatment with compound 17. This result was verified by qPCR, as shown in FIG. 25, and western blot analysis, as shown in FIG. 26. Knockdown of Myc in LSCs using siRNA leads to a subsequent downregulation of the glutamine receptor SLC1A5 and a decrease in OXPHOS. Thus, without wishing to be bound by theory, the results of these experiments demonstrate that STAT3 affects glutaminolysis likely through regulation of Myc.

The foregoing examples of the present invention have been presented for purposes of illustration and description. Furthermore, these examples are not intended to limit the invention to the form disclosed herein. Consequently, variations and modifications commensurate with the teachings of the description of the invention, and the skill or knowledge of the relevant art, are within the scope of the present invention. The specific embodiments described in the examples provided herein are intended to further explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

EQUIVALENTS

The details of one or more embodiments of the disclosure are set forth in the accompanying description above. Although any methods and materials similar or equivalent to those described herein can be used in the practice or testing of the present disclosure, the preferred methods and materials are now described. Other features, objects, and advantages of the disclosure will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this disclosure belongs. All patents and publications cited in this specification are incorporated by reference.

The foregoing description has been presented only for the purposes of illustration and is not intended to limit the disclosure to the precise form disclosed, but by the claims appended hereto.

What is claimed is:
1. A compound of Formula (I):

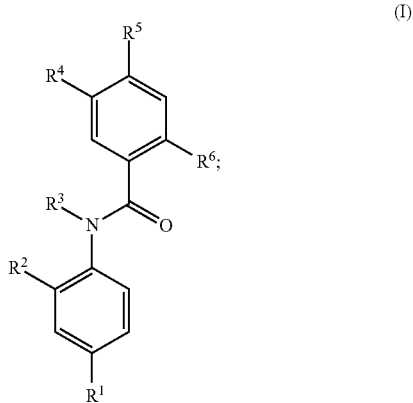

a prodrug thereof, or a pharmaceutically acceptable salt thereof, wherein:
$R^1$ is nitro, CN, $SO_3H$, —C(=O)—$OR^{1S}$, —(C=O)—$N(R^{1S})_2$, or $N(R^{1S})_2$;
each $R^{1S}$ independently is H or $C_{1-6}$ alkyl;
$R^2$ is halogen;
$R^3$ is H or $C_{1-6}$ alkyl;
$R^4$ is halogen;
$R^5$ is 5- to 12-membered heteroaryl optionally substituted with one or more $R^{5S}$;
each $R^{5S}$ independently is halogen, $C_{1-6}$ alkyl, —$OR^{5SS}$, —$N(R^{5SS})_2$, —($C_{1-6}$ alkyl)-$OR^{5SS}$, —($C_{1-6}$ alkyl)-$N(R^{5SS})_2$, —C(=O)—$R^{5SS}$, or —C(=O)—$OR^{5SS}$;
each $R^{5SS}$ independently is H or $C_{1-6}$ alkyl;
$R^6$ is $OR^{6S}$ or —C(=O)—$OR^{6S}$; and
$R^{6S}$ is H or —C(=O)—$C_{1-6}$ alkyl.

2. The compound of claim 1, being of Formula (I-a):

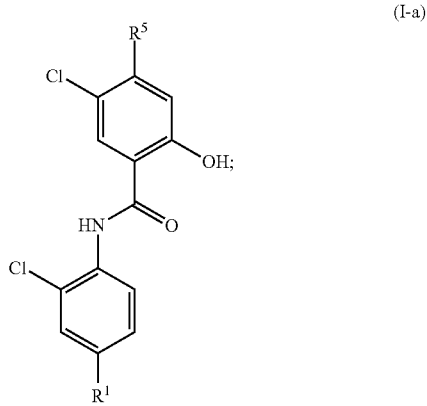

or a pharmaceutically acceptable salt thereof, wherein:
$R^1$ is nitro, CN, $SO_3H$, —C(=O)—$OR^{1S}$, —(C=O)—$N(R^{1S})_2$, or $N(R^{1S})_2$;
each $R^{1S}$ independently is H or $C_{1-6}$ alkyl;
$R^5$ is 5- to 12-membered heteroaryl optionally substituted with one or more $R^{5S}$;
each $R^{5S}$ independently is halogen, $C_{1-6}$ alkyl, —$OR^{5SS}$, —$N(R^{5SS})_2$, —($C_{1-6}$ alkyl)-$OR^{5SS}$, —($C_{1-6}$ alkyl)-$N(R^{5SS})_2$, —C(=O)—$R^{5SS}$, or —C(=O)—$OR^{5SS}$; and
each $R^{5SS}$ independently is H or $C_{1-6}$ alkyl.

3. A compound being selected from:
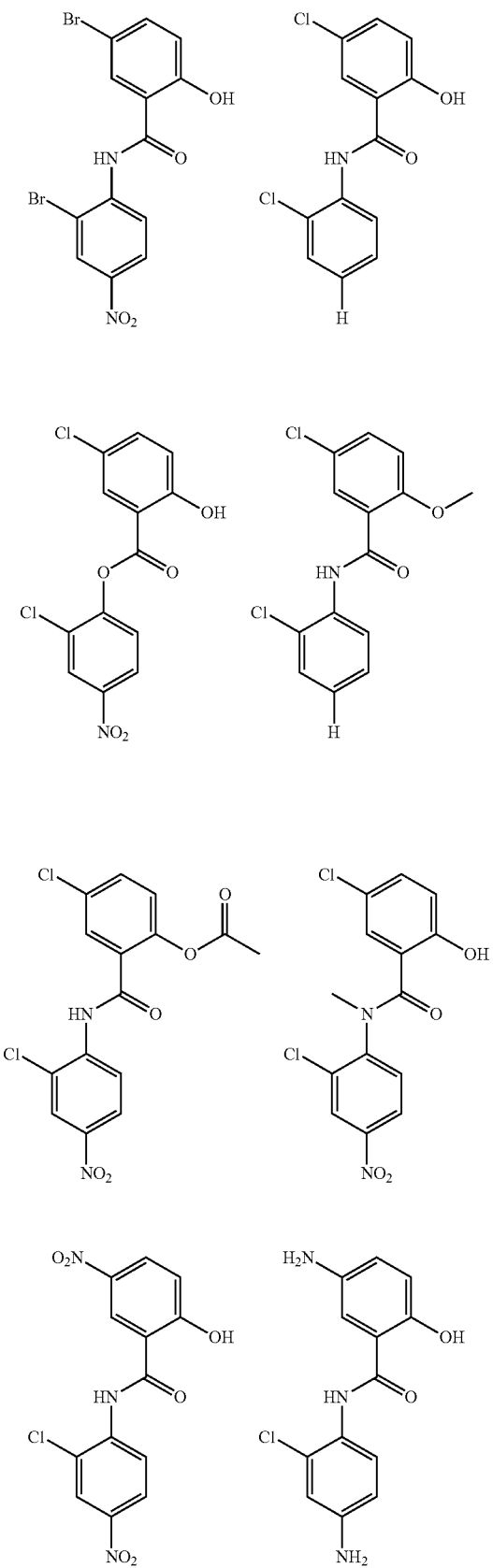
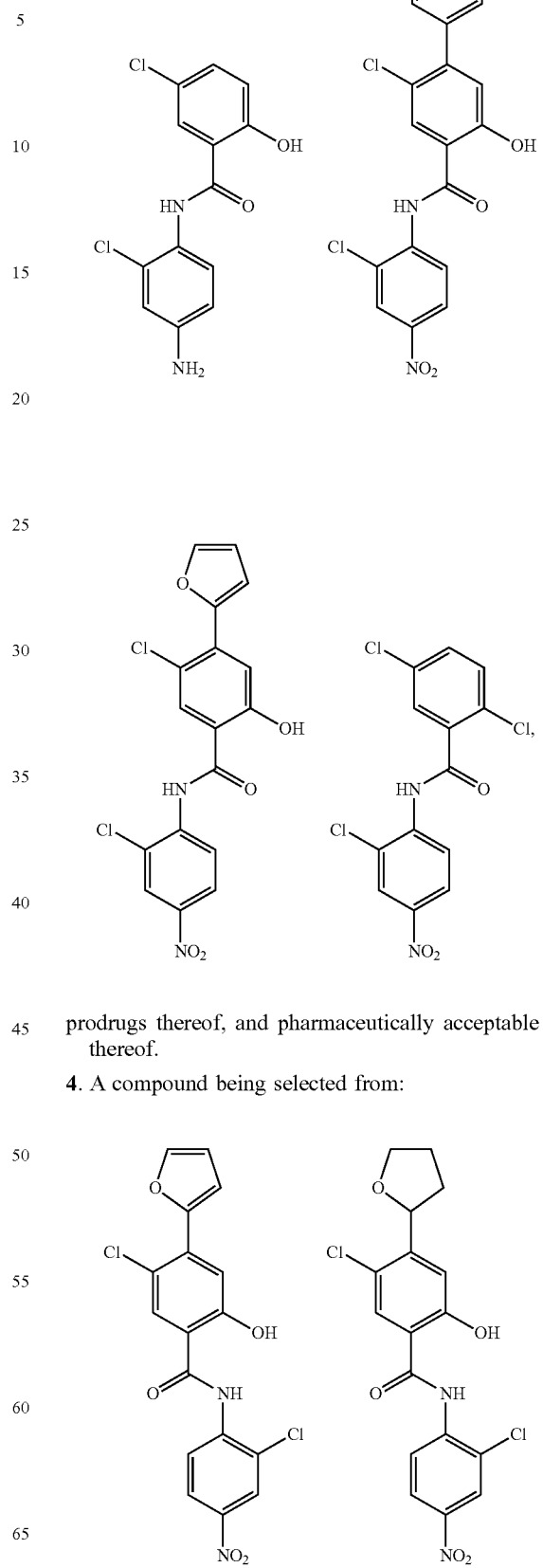
prodrugs thereof, and pharmaceutically acceptable salts thereof.
4. A compound being selected from:

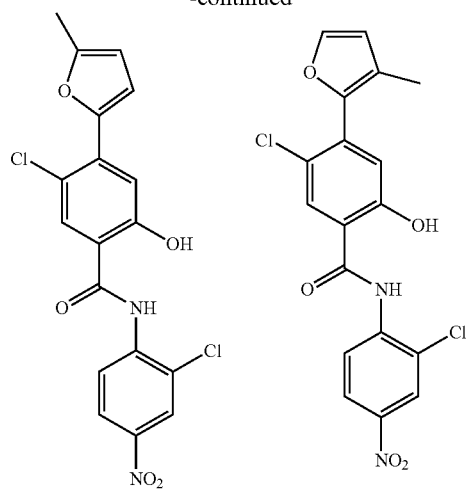
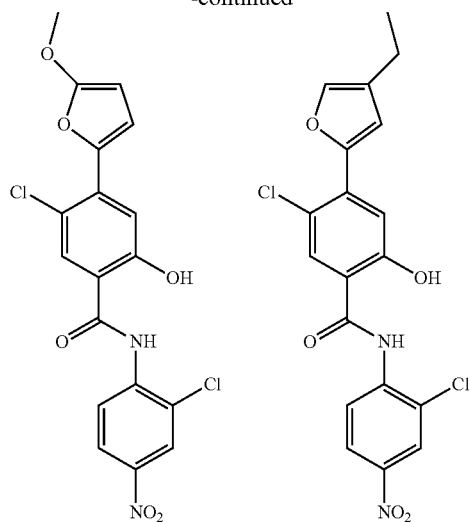
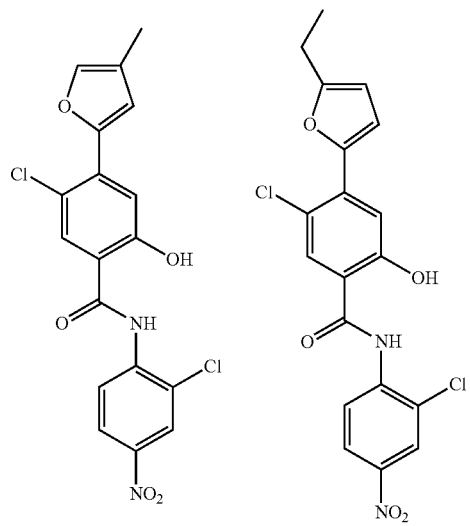
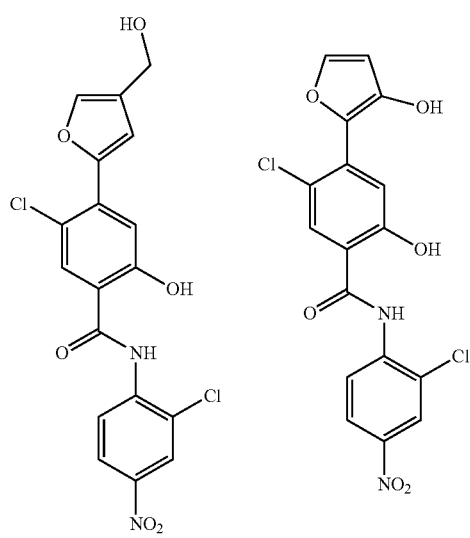
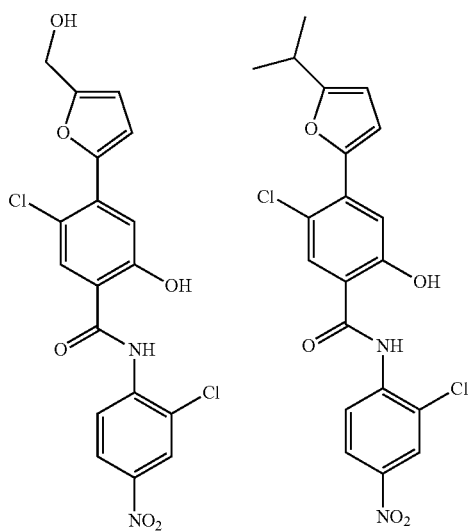
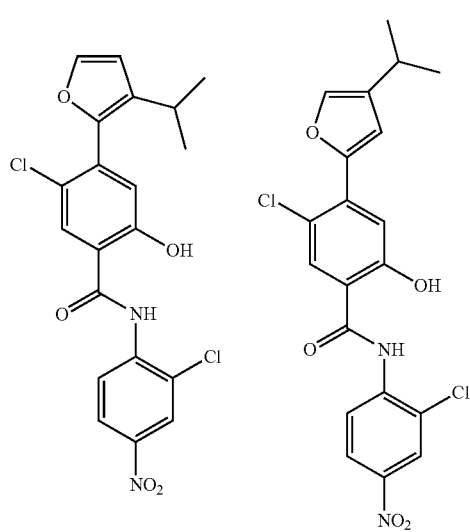

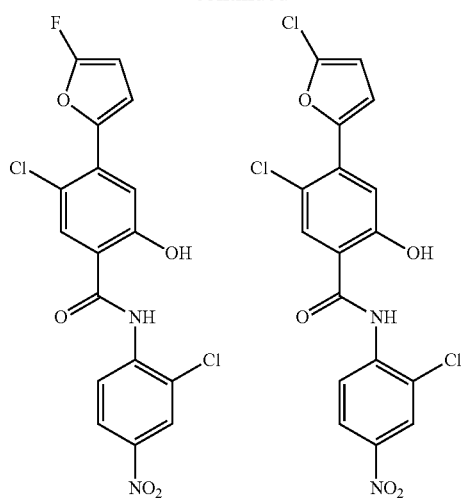
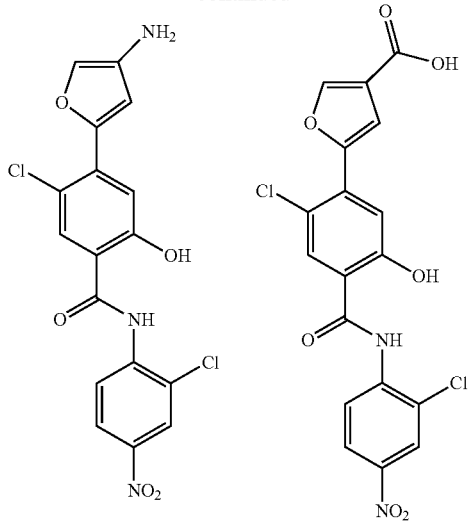
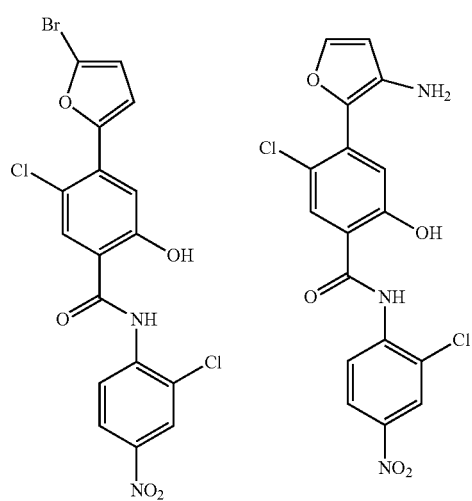
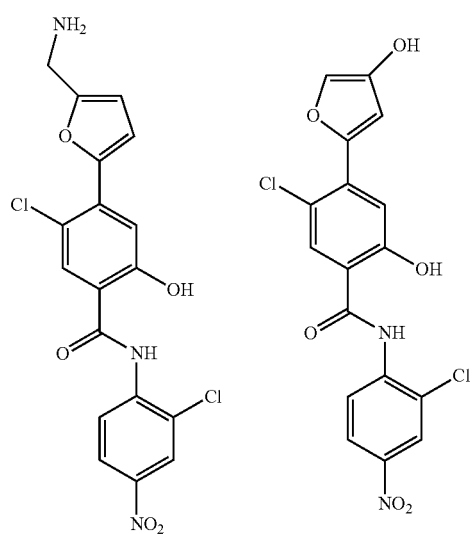

-continued
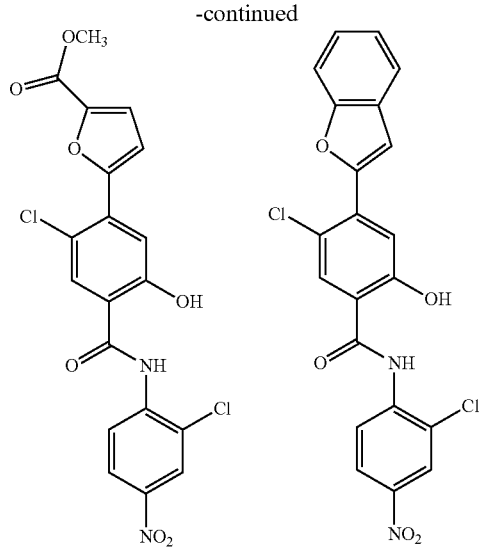
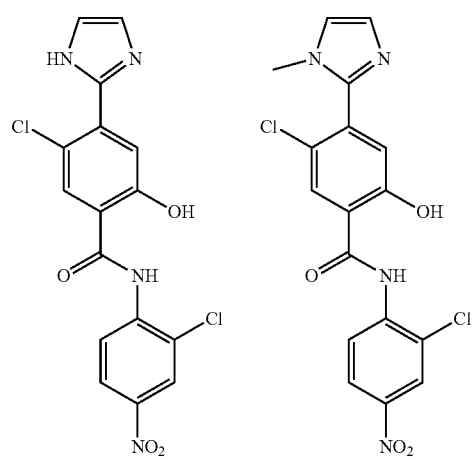
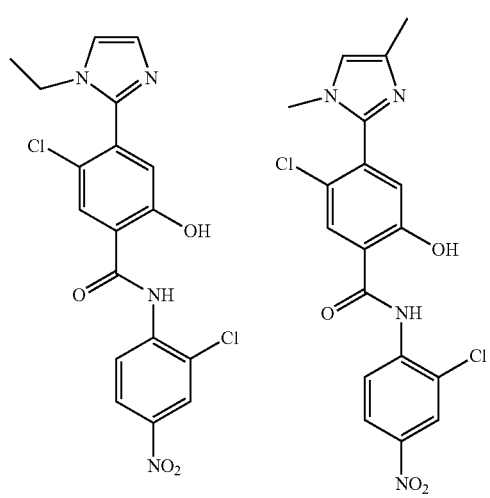
-continued
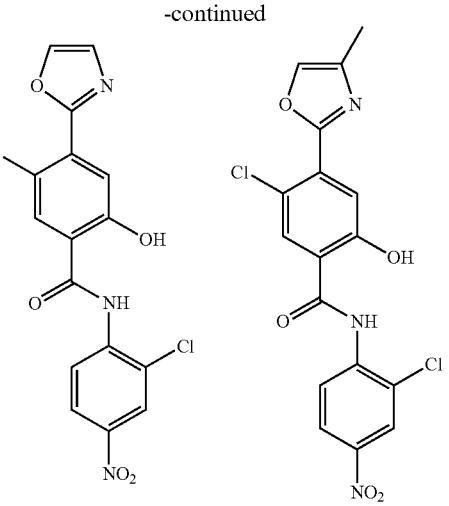
prodrugs thereof, and pharmaceutically acceptable salts thereof.
5. The compound of claim 4, being
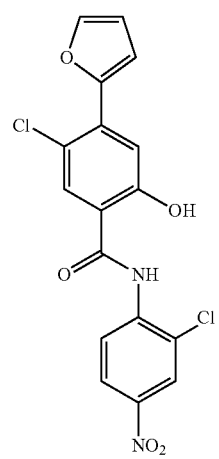 [SMILES: O=C(Nc1ccc([N+](=O)[O-])cc1Cl)c1cc(Cl)c(-c2ccco2)cc1O]
or a pharmaceutically acceptable salt thereof.

6. The compound of claim 4, being

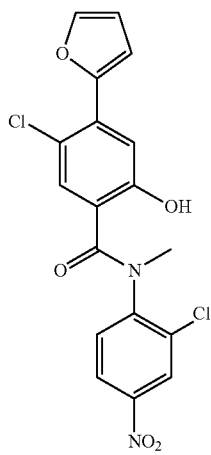 [SMILES: CN(C(=O)c1cc(Cl)c(-c2ccco2)cc1O)c1ccc([N+](=O)[O-])cc1Cl]

or a pharmaceutically acceptable salt thereof.

7. The compound of claim 3, being

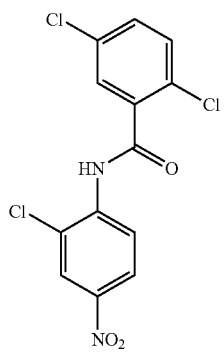 [SMILES: O=C(Nc1ccc([N+](=O)[O-])cc1Cl)c1cc(Cl)ccc1Cl]

or a pharmaceutically acceptable salt thereof.

8. A pharmaceutical composition comprising the compound of claim 1 or a prodrug thereof, and at least one pharmaceutically-acceptable additive.

9. A pharmaceutical kit containing the pharmaceutical composition of claim 8, prescribing information for the composition, and a container.

10. A method for modulating STAT3 transcription factor activity in a subject, comprising administering to the subject a therapeutically effective amount of the compound of claim 1.

11. A method of treatment, amelioration of cancer or prevention of metastasis of a cancer in a subject, comprising administering to the subject a therapeutically effective amount of the compound of claim 1.

12. The method of claim 11, wherein the cancer is a solid tumor or a blood cancer.

13. The method of claim 11, wherein the cancer is colorectal cancer, hepatocellular carcinoma, non-small cell lung cancer, ovarian cancer, prostate cancer, breast cancer, triple negative breast cancer, T-cell lymphoma, Hodgkin's lymphoma, gastric cancer, skin cancer, melanoma, leukemia, squamous cell carcinoma, nasopharyngeal carcinoma, glioblastoma, pancreatic ductal adenocarcinoma, acute myeloid leukemia or obesity-induced hepatocellular carcinoma.

14. The method of claim 11, wherein the cancer is acute myeloid leukemia.

15. The method of claim 11, wherein the treatment, amelioration of cancer or prevention of metastasis of a cancer further comprises administering to the subject one or more anti-cancer agents, chemotherapeutic agents, immunotherapy agents, DNA alkylating agents, DNA damage response (DDR) inhibitors, cell-cycle checkpoint inhibitors, PARP inhibitors, HDAC inhibitors, kinase inhibitors, Bcl-2 inhibitors, Mcl-1 inhibitors, PD-L1 targeted agents, or bioenergetics modulators.

16. The method of claim 11, wherein the treatment, amelioration of cancer or prevention of metastasis of a cancer further comprises administering to the subject cytarabine, doxorubicin, paclitaxel, temozolomide, dasatinib, nilotinib, fluvestrant, venetoclax, metformin, 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abemaciclib, Abiraterone acetate, Abraxane, Accutane, Actinomycin-D, Adcetris, Ado-Trastuzumab Emtansine, Adriamycin, Adrucil, Afatinib, Afinitor, Agrylin, Ala-Cort, Aldesleukin, Alemtuzumab, Alecensa, Alectinib, Alimta, Alitretinoin, Alkaban-AQ, Alkeran, All-trans-retinoic Acid, Alpha Interferon, Altretamine, Alunbrig, Amethopterin, Amifostine, Aminoglutethimide, Anagrelide, Anandron, Anastrozole, Apalutamide, Arabinosylcytosine, Ara-C, Aranesp, Aredia, Arimidex, Aromasin, Arranon, Arsenic Trioxide, Arzerra, Asparaginase, Atezolizumab, Atra, Avastin, Avelumab, Axicabtagene Ciloleucel, Axitinib, Azacitidine, Bavencio, Bcg, Beleodaq, Belinostat, Bendamustine, Bendeka, Besponsa, Bevacizumab, Bexarotene, Bexxar, Bicalutamide, Bicnu, Blenoxane, Bleomycin, Blinatumomab, Blincyto, Bortezomib, Bosulif, Bosutinib, Brentuximab Vedotin, Brigatinib, Busulfan, Busulfex, C225, Cabazitaxel, Cabozantinib, Calcium Leucovorin, Campath, Camptosar, Camptothecin-11, Capecitabine, Caprelsa, Carac, Carboplatin, Carfilzomib, Carmustine, Carmustine Wafer, Casodex, CCI-779, Ccnu, Cddp, Ceenu, Ceritinib, Cerubidine, Cetuximab, Chlorambucil, Cisplatin, Citrovorum Factor, Cladribine, Clofarabine, Clolar, Cobimetinib, Cometriq, Cortisone, Cosmegen, Cotellic, Cpt-11, Crizotinib, Cyclophosphamide, Cyramza, Cytadren, Cytarabine, Cytarabine Liposomal, Cytosar-U, Cytoxan, Dabrafenib, Dacarbazine, Dacogen, Dactinomycin, Daratumumab, Darbepoetin Alfa, Darzalex, Dasatinib, Daunomycin, Daunorubicin, Daunorubicin Cytarabine (Liposomal), daunorubicin-hydrochloride, Daunorubicin Liposomal, DaunoXome, Decadron, Decitabine, Degarelix, Delta-Cortef, Deltasone, Denileukin Diftitox, Denosumab, DepoCyt, Dexamethasone, Dexamethasone Acetate, Dexamethasone Sodium Phosphate, Dexasone, Dexrazoxane, Dhad, Dic, Diodex, Docetaxel, Doxil, Doxorubicin, Doxorubicin Liposomal, Droxia, DTIC, Dtic-Dome, Duralone, Durvalumab, Eculizumab, Efudex, Ellence, Elotuzumab, Eloxatin, Elspar, Eltrombopag, Emcyt, Empliciti, Enasidenib, Enzalutamide, Epirubicin, Epoetin Alfa, Erbitux, Eribulin, Erivedge, Erleada, Erlotinib, Erwinia L-asparaginase, Estramustine, Ethyol, Etopophos, Etoposide, Etoposide Phosphate, Eulexin, Everolimus, Evista, Exemestane, Fareston, Farydak, Faslodex, Femara, Filgrastim, Firmagon, Floxuridine, Fludara, Fludarabine, Fluoroplex, Fluorouracil, Fluorouracil (cream), Fluoxymesterone, Flutamide, Folinic Acid, Folotyn, Fudr, Fulvestrant, G-Csf, Gazyva, Gefitinib, Gemcitabine, Gemtuzumab ozogamicin, Gemzar, Gilotrif, Gleevec, Gleostine, Gliadel Wafer, Gm-Csf, Goserelin, Granix, Granulocyte —Colony Stimulating Factor, Granulocyte Macrophage Colony Stimulating Factor, Halaven, Halotestin, Herceptin, Hexadrol, Hexalen, Hexamethylmelamine, Hmm, Hycamtin, Hydrea, Hydrocort Acetate, Hydrocortisone, Hydrocortisone Sodium Phosphate, Hydrocortisone Sodium Succinate, Hydrocortone Phosphate, Hydroxyurea, Ibrance, Ibritumomab, Ibritumomab Tiuxetan, Ibrutinib, Iclusig, Idamycin, Idarubicin, Idelalisib, Idhifa, Ifex, IFN-alpha, Ifosfamide, IL-11, IL-2, Imbruvica, Imatinib Mesylate, Imfinzi, Imidazole Carboxamide, Imlygic, Inlyta, Inotuzumab Ozogamicin, Interferon-Alfa, Interferon Alfa-2b (PEG Conjugate), Interleukin-2, Interleukin-11, Intron A (interferon alfa-2b), Ipilimumab, Iressa, Irinotecan, Irinotecan (Liposomal), Isotretinoin, Istodax, Ixabepilone, Ixazomib, Ixempra, Jakafi, Jevtana, Kadcyla, Keytruda, Kidrolase, Kisqali, Kymriah, Kyprolis, Lanacort, Lanreotide, Lapatinib, Lartruvo, L-Asparaginase, Lbrance, Lcr, Lenalidomide, Lenvatinib, Lenvima, Letrozole, Leucovorin, Leukeran, Leukine, Leuprolide, Leurocristine, Leustatin, Liposomal Ara-C, Liquid Pred, Lomustine, Lonsurf, L-PAM, L-Sarcolysin, Lupron, Lupron Depot, Lynparza, Marqibo, Matulane, Maxidex, Mechlorethamine, Mechlorethamine Hydrochloride, Medralone, Medrol, Megace, Megestrol, Megestrol Acetate, Mekinist, Mercaptopurine, Mesna, Mesnex, Methotrexate, Methotrexate Sodium, Methylprednisolone, Meticorten, Midostaurin, Mitomycin, Mitomycin-C, Mitoxantrone, M-Prednisol, MTC, MTX, Mustargen, Mustine, Mutamycin, Myleran, Mylocel, Mylotarg, Navelbine, Necitumumab, Nelarabine, Neosar, Neratinib, Nerlynx, Neulasta, Neumega, Neupogen, Nexavar, Nilandron, Nilotinib, Nilutamide, Ninlaro, Nipent, Niraparib, Nitrogen Mustard, Nivolumab, Nolvadex, Novantrone, Nplate, Obinutuzumab, Octreotide, Octreotide Acetate, Odomzo, Ofatumumab, Olaparib, Olaratumab, Omacetaxine, Oncospar, Oncovin, Onivyde, Ontak, Onxal, Opdivo, Oprelvekin, Orapred, Orasone, Osimertinib, Otrexup, Oxaliplatin, Paclitaxel, Paclitaxel Protein-bound, Palbociclib, Pamidronate, Panitumumab, Panobinostat, Panretin, Paraplatin, Pazopanib, Pediapred, Peg Interferon, Pegaspargase, Pegfilgrastim, Peg-Intron, PEG-L-asparaginase, Pembrolizumab, Pemetrexed, Pentostatin, Perjeta, Pertuzumab, Phenylalanine Mustard, Platinol, Platinol-AQ, Pomalidomide, Pomalyst, Ponatinib, Portrazza, Pralatrexate, Prednisolone, Prednisone, Prelone, Procarbazine, Procrit, Proleukin, Prolia, Prolifeprospan 20 with Carmustine Implant, Promacta, Provenge, Purinethol, Radium 223 Dichloride, Raloxifene, Ramucirumab, Rasuvo, Regorafenib, Revlimid, Rheumatrex, Ribociclib, Rituxan, Rituxan Hycela, Rituximab, Rituximab Hyalurodinase, Roferon-A (Interferon Alfa-2a), Romidepsin, Romiplostim, Rubex, Rubidomycin Hydrochloride, Rubraca, Rucaparib, Ruxolitinib, Rydapt, Sandostatin, Sandostatin LAR, Sargramostim, Siltuximab, Sipuleucel-T, Soliris, Solu-Cortef, Solu-Medrol, Somatuline, Sonidegib, Sorafenib, Sprycel, Sti-571, Stivarga, Streptozocin, SU11248, Sunitinib, Sutent, Sylvant, Synribo, Tafinlar, Tagrisso, Talimogene Laherparepvec, Tamoxifen, Tarceva, Targretin, Tasigna, Taxol, Taxotere, Tecentriq, Temodar, Temozolomide, Temsirolimus, Teniposide, Tespa, Thalidomide, Thalomid, TheraCys, Thioguanine, Thioguanine Tabloid, Thiophosphoamide, Thioplex, Thiotepa, Tice, Tisagenlecleucel, Toposar, Topotecan, Toremifene, Torisel, Tositumomab, Trabectedin, Trametinib, Trastuzumab, Treanda, Trelstar, Tretinoin, Trexall, Trifluridine/Tipiricil, Triptorelin pamoate, Trisenox, Tspa, T-VEC, Tykerb, Valrubicin, Valstar, Vandetanib, VCR, Vectibix, Velban, Velcade, Vemurafenib, Venclexta, Venetoclax, VePesid, Verzenio, Vesanoid, Viadur, Vidaza, Vinblastine, Vinblastine Sulfate, Vincasar Pfs, Vincristine, Vincristine Liposomal, Vinorelbine, Vinorelbine Tartrate, Vismodegib, Vlb, VM-26, Vorinostat, Votrient, VP-16, Vumon, Vyxeos, Xalkori Capsules, Xeloda, Xgeva, Xofigo, Xtandi, Yervoy, Yescarta, Yondelis, Zaltrap, Zanosar, Zarxio, Zejula, Zelboraf, Zevalin, Zinecard, Ziv-aflibercept, Zoladex, Zoledronic Acid, Zolinza, Zometa, Zydelig, Zykadia, Zytiga, or any combination thereof.

* * * * *